(12) United States Patent
Laing et al.

(10) Patent No.: US 10,357,448 B2
(45) Date of Patent: *Jul. 23, 2019

(54) ECHOGENIC VEHICLE FOR CLINICAL DELIVERY OF PLASMINOGEN ACTIVATOR AND OTHER FIBRIN-BINDING THERAPEUTICS TO THROMBI

(71) Applicants: Board of Regents, The University of Texas System, Austin, TX (US); University of Cincinnati, Cincinnati, OH (US)

(72) Inventors: Susan T. Laing, Houston, TX (US); Shaoling Huang, Houston, TX (US); David D. McPherson, Houston, TX (US); Christy K. Holland, Cincinnati, OH (US); Melvin E. Klegerman, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/729,631

(22) Filed: Oct. 10, 2017

(65) Prior Publication Data

US 2018/0042841 A1 Feb. 15, 2018

Related U.S. Application Data

(63) Continuation of application No. 12/044,189, filed on Mar. 7, 2008, now Pat. No. 9,814,672.

(60) Provisional application No. 60/893,964, filed on Mar. 9, 2007.

(51) Int. Cl.
*A61K 9/00* (2006.01)
*A61K 47/69* (2017.01)
*A61K 49/22* (2006.01)
*A61K 9/127* (2006.01)

(52) U.S. Cl.
CPC ............ *A61K 9/0009* (2013.01); *A61K 9/127* (2013.01); *A61K 47/6911* (2017.08); *A61K 47/6913* (2017.08); *A61K 49/227* (2013.01)

(58) Field of Classification Search
CPC .................................................. A61K 9/127
See application file for complete search history.

(56) References Cited

U.S. PATENT DOCUMENTS 9,814,672 B2 * 11/2017 Laing ................. A61K 47/6911

OTHER PUBLICATIONS

Gurewich, Blood Coagul. Fibrinolysis 11(5)401-408 (2000).
Gurewich, Blood Coagul. Thrombolysis 11:401-408 (2000).
Hamilton et al., Circulation 105(23):2772-2778 (2002).

(Continued)

*Primary Examiner* — Gollamudi S Kishore
(74) *Attorney, Agent, or Firm* — Williams Morgan, P.C.

(57) ABSTRACT

We disclose a composition comprising an echogenic liposome (ELIP) having an exterior surface, an interior surface, and at least one bilayer comprising at least one lipid selected from the group consisting of saturated phospholipids, unsaturated phospholipids, mixed phospholipids, and cholesterol, and a thrombolytic compound trapped by the ELIP. We also disclose a method of treating a medical condition in a patient characterized by a thrombus in the patient's vasculature, comprising administering to the patient the composition in an amount effective to reduce the size of the thrombus.

19 Claims, 17 Drawing Sheets

Results

(56) References Cited

OTHER PUBLICATIONS

Hamilton et al., Circulation 105:2772-2778 (Jun. 11, 2002).
Hamilton et al., Invest. Radiol. 37(4):215-221 (2002).
Hamilton et al., Invest. Radiol. 37:215-221 (2002).
Hamilton et al., J. Am, Coll. Cardiol. 43(3):453-460 (Feb. 4, 2004).
Hamilton et al., J. Am. Coll. Cardiol. 43:453-460 (2004).
Hamm et al., Arn. J. Cardiol. 80:200-204 (Jul. 15, 1997).
Hamm et al., Circulation 80:200-204 (1997).
Heath et al., Biochim. Biophys. Acta 599:42 (1981).
Heath et al., Blochim. Biophys. Acta 599:42-62 (1980).
Heeremans et al., J. Drug Target 3:301-310 (1995).
Holland et al., J. Acoust. Soc. Am. 112(5):2370 (Nov. 2002) (Abstract 4pBB5).
Holland et al., J. Acoust. Soc. Am. 112:2370 (2002).
Huang et al., J. Am. Coll. Cardiol. 39(5):228A (Mar. 6, 2002) (Abstract 807-5).
Huang et al., J. Am. Coll, Cardiol. 39:228A (2002).
Huang et al., J. Pharm. Sci. 90(12):1917-1926 (2001).
Huang et al., J. Pharm. Sci. 90(12):1917-1926 (Dec. 2001).
Huang et al., Molecular Ther. 5:S9 (2002).
Huang et al., Molecular Ther. 5:S9-S10 (May 2002).
Huang et al., Ultrasound Med. Biol. 28(3):339-348 (2002).
Huang et al., Ultrasound Med. Biol. 28:339-348 (2002).
Huber et al., Gene Ther. 7:1516-1525 (2000).
Jeon et al., Thromb. Res. 110:149-158 (2003).
Jones et al., Ultrasonic Imaging 11(2):137-138 (Apr. 1989) (Abstract).
Jones et al., Ultrasonic Imaging 11:137-138 (1989).
Kim et al., Biochim. Biophys. Acta 728:339 (1983).
Kim et al., Biochim. Biophys. Acta 728:339-348 (1983).
Kim et al., Hum. Gene Ther. 7:1339-1346 (1996).
Kim et al., Hum. Gene Ther. 7:1339-1346 (Jul. 10, 1996).
Kimura et al., Biol. Pharm. Bull. 17(1):126-130 (1994).
Kirby et al., Biotechnology 2(11):979-984 (Nov. 1984).
Kirby et al., Biotechnology 2:979 (1984).
Klegerman et al., AAPS J, 8:S2, Abstract T2111 (2006).
Klegerman et al., AAPS J. 8:S2, T2111 (2006) (Abstract).
Klegerman et al., Anal. Biochem. 300:46-52 (2002).
Klegerman et al., Arterioscl. Thromb. Vasc. Biol. 27:e-108 (2007).
Klegerman et al., Arterioscler, Thromb. Vasc. Biol, 22(5), P214 (2002) (Abstract).
Klegerman et al., Arterioscler. Thromb. Vasc. Biol. 27:e-108, P407 (2007) (Abstract).
Klegerman et al., Biochim. Biophys. Acta 1768:1703-1716 (2007).
Klegerman et al., Thromb. Vasc. Bin. 22(5):214 (2002).
Koch et al., Ultrasound Med. Biol. 26(5):897-903 (2000).
Koch et al., Ultrasound Med. Biol. 26:897-903 (2000).
Kolodgie et al., N. Eng. J. Med. 349:2316-2325 (2003).
Kudo et al., Circulation 80(1):1-345 (1989).
Kudo et al., Circulation 80(4), 1375 (Oct. 1989) (Abstract).
Landini et al., Ultrasound Med. Biol. 12(5):397-401 (1986).
Landini et al., Ultrasound Med. Biol. 12:397-401 (1986).
Tachibana et al., Circulation 92:1148-1150 (1995).
Tachibana et al., Echocardiography 18(4):323-328 (May 2001).
Tachibana et al., Echocardiography 18:323-328 (2001).
Tachibana, J. Vasc. Interv. Radiol. 3:299-303 (1992).
Taillefer, Semin. Nucl. Med. 31(2):102-123 (Apr. 2001).
Taillefer, Semin. Nucl. Med. 31:102-123 (2001).
Tiukinhoy et al., Invest, Radio. 12:732-738 (2000).
Tiukinhoy et al., Invest. Radio. 35(12):732-738 (2000).
Tiukinhoy et al., Invest. Radio. 39(2):104-110 (Feb. 2004).
Tiukinhoy et al., Invest. Radio. 39:104-110 (2004).
Tiukinhoy-Laing et al., "Ultrasound-Facilitated Thrombolysis Using Tissue-Plasminogen Activator-Loaded Echogenic Liposomes," Thromb. Res., In Press (2007).
Tiukinhoy-Laing et al., J. Drug Target 15:109-114 (2007).
Tiukinhoy-Laing et al., J. Drug Target, 15(2):109-114 (Feb. 2007).
Tiukinhoy-Laing et al., Thromb. Res. 119:777-784 (2007).
Tiukinhoy-Laing et al., Thromb. Res., In Press (2006).
Torchilin et al., "Surface Modification of Liposomes," In Torchilin, V.P., Weissig, V. eds., Liposomes, 2nd edition New York: Oxford University Press, pp. 193-229 (2003).
Torchilin et al., "Surface Modification of Liposomes," Liposomes, second edition, New York: Oxford University Press, pp. 193-229 (2003).
Tsurupa et al., Ann, NY Acad. Sci. 936:328-330 (2001).
Van de Weef, Eur. Heart J. 20:1452-1458 (1999).
Van de Werf, Eur. Heart J. 20:1452-1458 (1999).
Verheijen et al., EMBO J. 5(13):3525-3530 (1986).
Verheijen et al., EMBO J. 5:3525-3530 (1986).
Ward et al., J. Acoust. Soc. Am. 105(5):2951-2957 (May 1999).
Ward et al., J. Acoust. Soc. Am. 105:2951-2957 (1999).
Lasch et al., "Preparation of Liposomes," In Torchilin, V.P., Weissig, V. eds., Liposomes, 2nd edition, New York: Oxford University Press, pp. 24-25 (2003).
Lauer et al., Circulation 86:1257-1264 (1992).
Lefroy et al., Circulation 88(1):43-54 (Jul. 1993).
Leonetti et al., Proc. Natl. Acad. Sci. USA 87:2448-2451 (1990).
Leonetti et al., Proc. Natl. Acad. Sci. USA 87:2448-2451 (Apr. 1990).
Luo et al., Am. Heart J. 125(6):1564-1569 (1993).
Luo et al., Am. Heart J. 125(6):1564-1569 (Jun. 1993).
Luo et al., Circulation 94;775-778 (1996).
Madjid et al., Circulation 108:2730-2736 (2003).
Mahon et al., Am. J. Neuroradiol. 24(3):534-538 (Mar. 2003).
Mahon et al., Am. J. Neuroradiol. 24:534-538 (2003).
Martin et al., "Covalent Attachment of Proteins to Liposomes," In New RRC (Ed): Liposomes: A Practical Approach, IRL Press, New York (1990).
Martin et al., "Liposomes: A Practical Approach," Oxford University Press, New York, pp. 163-182 (1990).
Miller et al., Ultrasound Med. Biol. 22(9):1131-1154 (1996).
Miller et al., Ultrasound Med. Biol. 22:1131-1154 (1996).
Naghavi et al., Circulation 108:1664-1672 (2003).
Nesheim et al., J. Biol. Chem. 265(35):21541-21548 (Dec. 15, 1990).
Nesheim et al., J. Biol. Chem. 265:21541-21548 (1990).
New, "Liposomes: A Practical Approach," Oxford University Press, New York, pp. 19-21 (1990).
Ng et al., Circulation 88:1-502 (1993).
Nishioka et al., J. Am. Coll. Cardiol. 30(2):561-568 (1997).
Nordt et al., Heart 89:1358-1362 (2003).
Olsson et al., Ultrasound Med. Biol. 20(4):375-382 (1994).
Olsson et al., Ultrasound Med. Biol. 20:375-382 (1994).
Ord et al., Circulation 85:288-297 (1992).
Picano et al., Circulation 77:654-659 (1988).
Pick, Arch. Biochem. Biophys. 212(1):186-194 (Nov. 1981).
Pick, Arch. Biochem. Biophys. 212:186 (1981).
Pislaru et al., Eur. Heart J. 24:1690-1698 (2003).
Porter et al., Am. Heart J. 132(5):964-968 (Nov. 1996).
Porter et al., Am. Heart J. 132:964-968 (1996).
Ranby et al., Prog. Fibrinol. 5:233-235 (1981).
Rånby et al., Prog. Fibrinol. 5:233-235 (1981).
Raut et al., Thromb, Haemost. 76(1):56-64 (1996).
Raut et al., Thromb. Haemost. 76:56-64 (1996).
Rhoden et al., Biochemistry 18(19):4173-4176 (1979).
Rhoden et al., Biochemistry 18:4173 (1979).
Rosenthall et al., Clin. Nucl. Med. 20(5):398-402 (1995).
Rosenthall et al., Clin. Nucl. Med. 20:398-402 (1995).
Saad et al., Ultrasond Med. Biol. 18(8):715-723 (1992).
Saad et al., Ultrasound Med. Biol. 18:715-723 (1992).
Scopes, "Protein Purification: Principles and Practice," New York: Springer, pp. 265-266 (1982).
Siegel et al., Circulation 101(17):2026-2029 (2000).
Siegel et al., Circulation 101:2026-2029 (2000).
Sirol et al., Circulation 112:1594-1600 (2005).
Stracke et al., Stroke 38:1476-1481 (2007).

* cited by examiner

Results

A

B

A

B

ECHOGENIC VEHICLE FOR CLINICAL DELIVERY OF PLASMINOGEN ACTIVATOR AND OTHER FIBRIN-BINDING THERAPEUTICS TO THROMBI

BACKGROUND OF RELATED APPLICATIONS

This application is a divisional of co-pending U.S. patent application Ser. No. 12/044,189, filed Mar. 7, 2008, which claims priority to U.S. Provisional Application Ser. No. 60/893,964, filed on Mar. 9, 2017.

This invention was made with government support under Grant No. 74002 from the National Heart, Lung, and Blood Institute (NHLBI) and Grant No. NS47603 from the National Institute for Neurological Disorders and Stroke (NINDS). The government has certain rights in the invention.

1. FIELD OF THIS INVENTION

This invention relates to acoustically reflective oligolamellar liposomes containing internally separated bilayers and methods to make same for ultrasonic image enhancement.

2. DESCRIPTION OF THE PRIOR WORK IN THE FIELD

Ultrasonic assessment of internal body organs or tissue is a well known technique. This assessment can be made by sending a signal with a waveform in the high frequency sound spectrum ($10^6$ cycles/second) and detecting the reflected ultrasound properties. In current ultrasound procedures, the inherent reflective properties of the tissue are studied. In one recent patent, U.S. Pat. No. 4,900,540 a method for producing liposomes having an encapsulated gas is described. Liposomes are phospholipid bilayers discretely encapsulating an aqueous compartment. The composition and form of these lipid vesicles are analogous to that of cell membranes with hydrophilic polar groups directed inward and outward toward the aqueous media and hydrophobic fatty acids intercalated within the bilayer. Liposomes form spontaneously from a dry lipid film exposed to an aqueous medium and may be unilamellar and/or multilamellar. Unilamellar vesicles are typically classified as small (20 to 200 nm diameter) or large (approximately 1 micron). Multilamellar liposomes are classically described as having concentric bilayers, an "onion morphology". A type of multilamellar liposome termed oligolamellar liposomes are typically described as multilamellar liposomes with increased aqueous space between bilayers or have liposomes nested within bilayers in a nonconcentric fashion. Liposomes have many uses but are considered to be highly desirable for drug delivery and diagnostic applications.

As previously discussed, the '540 patent discloses a method for producing liposomes having an encapsulated gas. It is said that these liposomes can be injected for in vivo enhancement of organ imaging with ultrasound. A gas charged particle in vivo, however, may not be stable. Thus, it is desirable to develop a stable acoustically reflective liposome by controlling composition, structure and size alone.

SUMMARY OF THE INVENTION

In one embodiment, the present invention relates to a composition comprising an echogenic liposome (ELIP) having an exterior surface, an interior surface, and at least one bilayer comprising at least one lipid selected from the group consisting of saturated phospholipids, unsaturated phospholipids, mixed phospholipids, and cholesterol, and a thrombolytic compound trapped by the ELIP.

In one embodiment, the present invention relates to a method of treating a medical condition in a patient characterized by a thrombus in the patient's vasculature, comprising administering to the patient an amount effective to reduce the size of the thrombus of a composition comprising an echogenic liposome (ELIP) having an exterior surface, an interior surface, and at least one bilayer comprising at least one lipid selected from the group consisting of saturated phospholipids, unsaturated phospholipids, mixed phospholipids, and cholesterol, and a thrombolytic compound trapped by the ELIP.

DETAILED DESCRIPTION OF THE INVENTION

Figure 1:
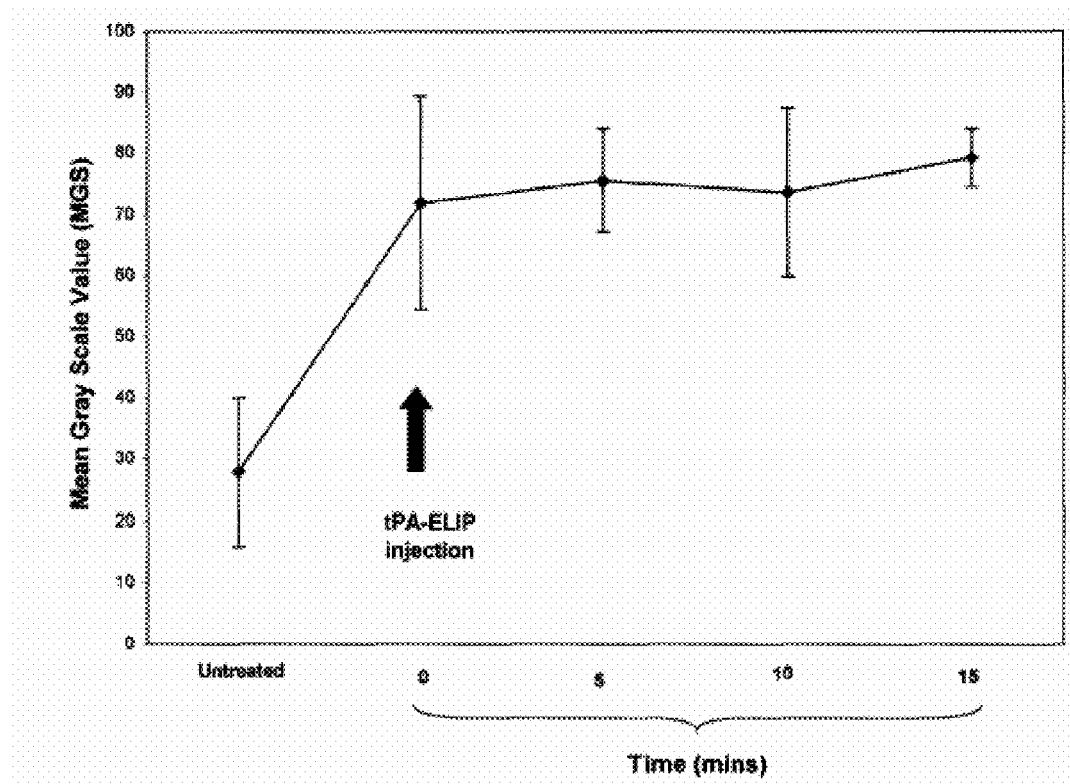
FIG. 1 shows a result from Example 11, that clot highlighting by tPA-ELIP was stable for at least 15 minutes in vivo

In one embodiment, the present invention relates to a composition comprising an echogenic liposome (ELIP) having an exterior surface, an interior surface, and at least one bilayer comprising at least one lipid selected from the group consisting of saturated phospholipids, unsaturated phospholipids, mixed phospholipids, and cholesterol, and a thrombolytic compound trapped by the ELIP.

The at least one bilayer can comprise one or more lipid selected from the group consisting of saturated phospholipids, unsaturated phospholipids, mixed phospholipids, and cholesterol. In one embodiment, the at least one bilayer of the echogenic liposome comprises at least one lipid selected from the group consisting of dipalmitoylphosphatidylcholine (DPPC), dioleoylphosphatidylcholine (DOPC), dipalmitoylphosphatidylglycerol (DPPG), dipalmitoylphosphatidylethanolamine (DPPE), egg phosphatidylcholine (PC), and cholesterol. In a further embodiment, the ELIP comprises from about 0 mole parts to about 90 mole parts DPPC, from about 0 mole parts to about 50 mole parts DOPC, from about 10 mole parts to about 50 mole parts DPPG, from about 0 mole parts to about 20 mole parts DPPE, from about 0 mole parts to about 90 mole parts egg PC, and from about 2 mole parts to about 15 mole parts cholesterol, wherein the total amount of DPPC, DOPC, DPPG, DPPE, egg PC, and cholesterol is 100 mole parts. In an even further embodiment, the ELIP comprises about 46 mole parts DPPC, about 24 mole parts DOPC, about 24 mole parts DPPG, and about 6 mole parts cholesterol. In another even further embodiment, the ELIP comprises about 38 mole parts DPPC, about 24 mole parts DOPC, about 24 mole parts DPPG, about 8 mole parts DPPE, and about 6 mole parts cholesterol.

In one embodiment, the ELIP is intrinsically echogenic.

The thrombolytic compound can be trapped by the ELIP internally, externally, in a transbilayer fashion, or some combination thereof. In one embodiment, at least some of the thrombolytic compound is exposed on the exterior surface of the ELIP. Any technique of conjugating the thrombolytic compound to the ELIP can be used. In one embodiment, the thrombolytic compound is conjugated to the ELIP by a thioether linkage.

Any thrombolytic compound can be used. The thrombolytic compound can be identical to its native form or can be modified away from its native form to enhance its entrapment in the ELIP or to modify its interaction with its substrate. In one embodiment, the thrombolytic compound is human tissue plasminogen activator (tPA). In a further embodiment, the tPA is inhibited. An exemplary route of tPA inhibition is with D-phe-L-pro-L-arg-chloromethyl ketone (PPACK).

In one embodiment, the composition comprises from about 1 µg to about 50 µg entrapped tPA per 1 mg ELIP.

To target the composition to a particular location in a mammalian body, the composition can further comprise an active targeting molecule. In one embodiment, the active targeting molecule is selected from the group consisting of antibodies against components of thrombus or ligands specific for thrombus, wherein the active targeting molecule is exposed on the exterior surface of the ELIP. Alternatively or in addition, the thrombolytic compound can function as a targeting molecule.

In one embodiment, the composition further comprises a glycoprotein (GP) IIb/IIIa inhibitor. In a further embodiment, the GP IIb/IIIa inhibitor is selected from the group consisting of abciximab, eptifibatide, and tirofiban.

In another embodiment, the present invention relates to a method of treating a medical condition in a patient characterized by a thrombus in the patient's vasculature, comprising administering to the patient an amount effective to reduce the size of the thrombus of a composition comprising an echogenic liposome (ELIP) having an exterior surface, an interior surface, and at least one bilayer comprising at least one lipid selected from the group consisting of saturated phospholipids, unsaturated phospholipids, mixed phospholipids, and cholesterol, and a thrombolytic compound trapped by the ELIP.

The composition can be as described above.

Administering can deliver any pharmaceutically-effective amount of the thrombolytic compound to the patient. In one embodiment, administering delivers to the patient from about 1 µg of the thrombolytic compound per kg body weight to about 1 mg of the thrombolytic compound per kg body weight.

To enhance administration of the thrombolytic compound, in one embodiment, the method further comprises applying ultrasonic energy to the ELIP and thrombus to enhance thrombolysis. Though not to be bound by theory, applying ultrasonic energy to the ELIP and thrombus may enhance release of the thrombolytic compound from the ELIP, absorption of the thrombolytic compound by the thrombus, or both. Applying ultrasonic energy to the ELIP and thrombus to enhance thrombolysis can be performed according to the teachings of C. K. Holland, D. S. Kanter, L. J. Busse, K. R. Wagner, "Transcranial ultrasound thrombolysis system and method of treating a stroke," U.S. Pat. No. 7,300,414.

In addition to administering the thrombolytic compound, in light of the observation that the ELIP is echogenic, the method can further comprise ultrasonic imaging of the thrombus. This may allow a medical practitioner to monitor the size of the thrombus or the rate or extent of thrombolysis.

In accordance with this invention, acoustically reflective liposomes are provided which may be used alone as an ultrasonic contrast agent or which are conducive to site specific ligand conjugation to enhance ultrasonic imaging of specific tissues types or receptors in the body.

The inventors have discovered that the echogenicity of liposomes is a function of composition, morphology and size. With respect to morphology, the inventors have found that liposomes may be simply produced by mechanical dispersion of a dried phospholipid film (e.g. phosphatidylcholine) into an aqueous medium. This procedure typically produces classical multilamellar and fewer oligolamellar vesicles. The addition of phosphatidylethanolamine imparts morphological changes to the arrangement of the bilayers. Though not to be bound by theory, the head groups of the phosphatidylethanolamine may result in this acoustically reflective arrangement, presumably an oligolamellar type of liposome. Furthermore, liposomes with similar acoustic properties may be produced by the inclusion of charged lipids, (e.g. phosphatidylglycerol) which could lead to a more oligolamellar distribution secondary to internal repulsion of the lipid bilayers.

More specifically, the above described oligolamellar liposomes possess a series of membrane-fluid interfaces that in the aggregate are ultrasonically reflective. Liposomes produced by the same method, but without the incorporation of phosphatidylethanolamine or charged lipids (e.g. pure phosphatidylcholine vesicles) are not echogenic, despite their multilamellar morphology, because the bilayers are typically closely opposed and act as a single acoustic interface.

Although both classic multilamellar and oligolamellar liposomes may be created directly from a dried lipid film without lyophilization, and though not to be bound by theory, the inventors currently understand that the classical multilamellar form predominates this approach and that such vesicles are less echogenic than the oligolamellar form which may predominate after rehydration of freeze-dried liposomes.

Ultrasonically reflective liposomes may be created by any procedure which creates oligolamellar vesicles with internally separated bilayers. The inventors have demonstrated the use of liposome composition (i.e. phosphatidylethanolamine incorporation) to create this effect, but one can easily envision mechanical means to the same end. One example is the conjugation of ligands (i.e. antibodies, peptides, lectins, etc,) to lipid components of the membrane then incorporation of these components between layers of the multilamellar vesicles by a suitable process. In this scenario, the relatively large size of the ligands bound to the inner and outer bilayer surfaces could either primarily spread or secondarily enhance the separation of multilamellar bilayers.

Oligolamellar liposomes may be prepared by but are not limited to the following processes: lyophilization, repeated freeze-thaw, a modified double emulsion technique. Production through lyophilization is the current standard operating procedure. The acoustically reflective liposome particle is made by combining phosphatidylethanolamine with other lipids (e.g. phosphatidylcholine) into a dried film, resuspending the film with deionized water with or without cryoprotectant, to form a liposome, reducing the size of the particles to less than about 400 nm, lyophilizing the particles, and resuspending the particles in buffer. Particles may then be extruded to a size between about 0.8 and 10 microns. This method is the most conducive to conjugating protein ligands since it avoids exposure of the protein to organic solvents, evaporation or mechanical destruction. The antibody is conjugated in an aqueous buffer to unilamellar liposomes less than 400 nm in diameter for maximum efficiency and the conjugate may be freeze-dryed with mannitol to help protect the peptide while allowing the vesicles to structurally degrade.

Alternatively, in the modified double emulsion method, an organic solution containing triolein, phospholipids and cholesterol is combined on a volume to volume basis with an aqueous solution typically containing materials to be entrapped. This solution is vigorously agitated to form a water-in-oil emulsion. This emulsion is then combined with a sucrose solution and agitated again, creating a water-in-oil-in-water emulsion, or a double emulsion. Evaporation of the organic solvent leaves multicompartmental liposomes. This method is compatible with liposome encapsulation of but is less conducive for conjugate with proteins or other biological macromolecules (Kim, S., Turker, M. S., Chi, E. Y., Sela, S. and Martin, G. M., 1983 Biochim. Biophys. Acta 728,339; Gao, K. and Huang, L., 1987 Biochim. Biophys. Acta 897, 377).

Another method for producing oligolamellar liposomes is a variant of the lyophilization method and involves freezing and thawing of small unilamellar liposomes (Pick, U. 1981 Arch. Biochem. Biophys., 212, 186). The repeated freeze-thawing of liposomes leads to membrane rupture and reannealing into larger multicompartmental vesicles. These membranes typically incorporate charged phospholipids into the bilayers to provide a nidus for ice crystal formation. Although the protein ligands could easily be conjugated to the smaller unilamellar liposomes, repeated freeze-thawing of biologically active proteins may destroy their bioactivity and reduce their efficacy as targeting ligands.

The liposomes which have been found to be useful in this invention incorporate phosphatidylethanolamine into the bilayer liposomes that can be formed into a vesicular structure. The liposome can be formed from lipids such as phosphatidylcholine (PC) and phosphatidylethanolamine (PE). Preferably the phosphatidylcholine ranges from about 50 to 95 mol % of the lipid content of the liposome, but can generally range from 60 to 90 mol % of the liposome, while phosphatidylethanolamine preferably ranges from 2 to 20 mol %, but generally from about 5 to 10 mol percent of the lipid content of the liposome.

Incorporation of cholesterol, another neutral lipid, has been found to contribute an echogenic component to liposomes which was lost after polycarbonate extrusion, suggesting that large liposome size increases echogenicity. Work by Rhoden and Golden (Rhoden, V and Goldin, S 1979 Biochemistry 18, 4173) has indicated that incorporating cholesterol into the lipid bilayer will increase particle size while, the addition of charged phospholipids decrease vesicle size. Cholesterol intercalates within the phosphatidylcholine bilayer with very little change in area by occupying the regions created by the bulky phosphatidylcholine headgroups. This increases the packing density and structural stability of the bilayer and may contribute to acoustic character (New, R. R. C., 1990 In New, R. R. C. (ed): Liposomes: a practical approach, (ed), Oxford University Press, New York, pp 19-21).

With respect to size, it was found that liposomes of approximately one to four microns in size were lyophilized without excipients and were echogenic upon resuspension with Tris buffer, pH 7.5. Additionally, it was found that decrease of prelyophilization particle size to less than one micron with probe sonication and a sugar excipient resulted in echogenic liposomes. During lyophilization, the smaller vesicles may break down more completely and enhance the lipid interactions upon rehydration. The addition of sugar (mannitol) was selected to provide bulk to the lyophilized powder without cryoprotecting the vesicle size. Other sugars, such as trehalose or maltose can be used to provide bulk, but also tend to preserve liposome integrity during freeze-drying and may be contraindicated in the production of echogenic liposomes from small unilamellar liposomes.

The smaller the liposomes the higher the ultrasonic frequency required to resolve the vesicle. In practice, a single liposome (1-2 microns) is not resolvable with commercially available diagnostic ultrasonic transducers. However, discrete liposomes and the coalescence of liposomes either randomly in solution or secondary to specific targeting ligands contribute to ultrasonic scattering, and can create an acoustic interface which may be visualized and quantified. Moreover, in vivo, targeted echogenic liposomes will benefit from enhanced echogenicity secondary to creation of multiple liposome-tissue interfaces and a transient increase in target tissue size and density.

An acoustically reflective liposome particle generally ranges from 0.8 to 10 microns, but preferably 0.8 to 2.0 microns.

In summary, the lyophilization method (refered to as dehydration-rehydration procedure) appears to provide the preferred method for creating echogenic, protein-targeted liposomes. The small unilamellar vesicles are optimum for protein conjugation and can be ruptured and enlarged into multivesicular liposomes without destroying the biological activity of the ligand. This method was first suggested by Kirby and Gregoriadis (Kirby, C. and Gregoriadis, G., 1984 Biotechnology 2, 979 (hereby incorporated by reference) for the purpose of increasing liposome entrapment efficiency. The inventors have discovered that liposomes produced by this method with the appropriate chemical composition are echogenic and suitable for targeting.

The acoustically reflective liposomes can be conjugated to a site specific ligand such as an antibody, lectin, peptide or nucleic acid. A variety of methods have been reported to attach proteins to liposomes covalently. (Martin, F. J., Heath, T. D. and New, R. R. C., 1990 In Liposomes: a practical approach. Oxford University Press, New York, pp 163-182; hereby incorporated by reference). The most popular methods involve synthesis of thiol-reactive lipids using either N-succinimidyl-pyridyl-dithiopropionate (SPDP) or N-succinimidyl-(4-[p-maleimidophenyl])-butyrate (SMPB). SPDP produces a reversible disulfide bond and SMPB produces an irreversible thioether. The conjugation process is essentially the same for both reagents and the inventors used SPDP for in vitro experiments reported herein.

S-acetylmercaptosuccinic anhydride can be used instead of SPDP with a substitution of hydroxylamine for dithiothreitol in the process to reduce the number of purification steps required (Martin, F. J., et al. Supra. 163-182).

Another method described by Heath et al. (Heath, T. D., Maher, B. A. and Paphadjopoulos, D., 1981: Biochim. Biophys. Acta 599, 42) involves the use of periodate to create a Schiff base between glycolipids incorporated into the lipid membrane and primary or secondary amino groups on proteins. This method provides 20% binding of the initial protein with a theoretical maximum of 40%. Conjugation to larger liposomes appears better than smaller unilamellar liposomes, a factor which may be less desirable for producing echogenic liposomes by lyophilization.

Phosphatidylethanolamine can also be derivatized by attaching a bifunctional straight-chain (6-8 carbons) dicarboxylic acid which can bridge between the lipid and protein. The phosphatidylethanolamine may be derivatized by either a di-N-hydroxysuccinimide derivative or by reaction with carbodiimide. The former route must be used with a process which prepares liposomes rapidly without significant subsequent processing. The carbodiimide method is prone to extensive cross-linking and often requires citraconylate blocking of endogenous amino groups. This blocking reagent is removed at pH 4.4 which may precipitate peptides or begin to hydrolyze the liposome membranes (Martin, F. J., et al. Supra. at 163-182).

Liposomes can be conjugated with Protein A or Protein G, which have inherent affinity for immunoglobulins. Liposomes can be conjugated with avidin, which strongly binds to biotin that can be attached to immunoglobulins or other ligands thereby effecting of the coupling a ligand to liposomes. Finally, sugars and other oligosaccharides may be conjugated to liposomes containing a pure or SPDP-derivatized phosphatidylethanolamine via endogenous aldehyde groups of the saccharide by introducing a thiol residue onto the sugar or by carboxylating free hydroxyl groups with succinic anhydride followed by a carbodiimide coupling reaction (Martin, F. J., et al. Supra at 163-182).

An acoustically reflective liposome particle may be used alone as an ultrasonic contrast agent or with a ligand conjugation for specifically targeted ultrasonic image enhancement. More specifically, ligand-targeted, acoustically reflective liposomes may be used to enhance ultrasonic imaging of intravascular structures as well as extravascular structures accessible due to increased permeability of the vasculature or by direct administration into a nonvascular space. The potential cardiovascular targets include myocardial tissue (antimyosin antibody), vascular clot (anti-fibrin antibody), vegetations (anti-bacterial determinant antibody), endothelial surface (anti-receptor or surface determinant antibody) and tumors (anti-tumor antibody). Additionally, other tissue structures in the penetrable spaces of joints, (lymphatic system; urogenital or pulmonary bronchial alveolar tree) may be ultrasonically enhanced with specific acoustically reflective liposomes administered directly into these spaces.

The routes of administration include intravascular, intralymphatical, intrathecal, intraurological, intracapsular, and bronchial lavage. The acoustically reflective liposome made be administered as a bolus of liposomes or as an infusion in a pharmaceutically acceptable carrier such as saline or glucose in water.

As with other injected pharmaceutical agents, the acoustically reflective liposome, is administered as a sterile compound. To prepare a sterile composition of matter the acoustically reflective liposome is prepared under aseptic conditions using sterilized buffers and reagents. In one embodiment, the ELIP is sterilized by UV light or by sterile filtration followed by lyophilization.

Visualization of the in situ liposomes is possible with virtually all ultrasonic imaging modalities, including intravascular (catheter-based), transcutaneous transvascular/epicardial (conventional echocardiography, vascular or high frequency) and transesophageal echocardiography. The precise imaging technique appropriate for a given application must take into account the clinical objective of the procedure, anatomic site of interest and medical condition of the patient.

Two important uses for liposome enhancement to tissue would be the following. First, the standard transcutaneous or transesophageal ultrasound would be used to identify cardiac structure. Liposomes would subsequently be used to enhance structure definition, either through their perfusion into a vascular bed to identify regions of perfusion (i.e. myocardial) or to identify pathologic structures by directly or indirectly "highlighting" of the target. The transducers that are used utilize probes from 2 to 15 MHz and are placed transcutaneously/transvascular/epicardially/or transesophageally to image cardiovascular structures.

In the second instance, liposomes would be utilized in conjunction with intravascular ultrasound imaging devices. These devices generate images of vascular structure and operate at a frequency of 10-100 MHz. These catheters do not generally impede blood flow and they would be directed to the region of interest with the liposomes highlighting structures such as plaque, thrombus or endothelial receptors/determinants.

Using either the intravascular or the transcutaneous/transvascular/epicardial/transesophageal method, the 2-dimensional B-mode ultrasound images generated are amenable to more sophisticated image processing and/or analysis. Gray-scale texture analysis, radiofrequency signature analysis and a variety of additional complementary ultrasonic material characterization techniques may find use in enhancing the interpretation of these data.

Intrinsically echogenic liposomes (ELIP), consisting of dipalmitoylphosphatidylcholine (DPPC), dioleoylphosphatidylcholine (DOPC), dipalmitoylphosphatidylglycerol (DPPG) and cholesterol (Chol), can be loaded with tissue plasminogen activator (tPA) at the time of initial rehydration. The resultant tPA-ELIP will preferentially bind to fibrin-containing structures, such as clots (thrombi), once injected into the circulation, and are more effective in reversing clot formation in the presence of ultrasound energy applied over the site of the thrombus than injection of free tPA alone. The efficient and safe delivery of drugs to target sites is the goal of any clinically useful pharmacotherapeutic strategy. This is particularly relevant when dealing with drugs with small therapeutic windows or those with severe adverse effects. Systemic delivery of tPA for acute thrombo-occlusive diseases, although life-saving, is limited by potential for significant bleeding. There is also the concern of effective concentrations reaching the desired site for plasminogen activation. Targeted delivery of a thrombolytic agent to the site of occlusion is a desirable clinical strategy, with implications for the treatment of many thrombo-occlusive diseases. Hence, development of a fibrin-targeted, ultrasound-releasable lytic complex represents a novel therapeutic strategy for the local delivery of a thrombolytic agent.

It has been known since the 1970s that plasminogen activators found in certain tissues are strongly bound to fibrin, which logically explains the fibrin specificity of physiologic thrombolysis (Gurewich, 2000). Recombinant tPA was engineered to potentiate this fibrin specificity by a positive feedback mechanism whereby binding of the tPA to fibrin results in an increased uncovering of the tPA binding site (the aC domain). Tsurupa and Medved (Tsurupa and Medved, 2001) demonstrated that tPA binds to the fibrinogen aC domains with high affinity, with a $K_d$ value reported as 33±5 nM. Though not to be bound by theory, we currently understand that tPA even when associated with our ELIP will maintain its fibrin binding properties. This will render the tPA-loaded ELIP fibrin-specific, providing a self-targeted agent without requirement for further manipulation of the ELIP. Since tPA is a naturally occurring human protein, it will not provoke an immune response that causes adverse effects and loss of treatment efficacy.

Diagnostic ultrasound techniques have been developed to evaluate the presence and progression of atherosclerosis, by identifying the extent, components and morphology of atheroma and thrombus. Calcium, fibrous tissue, and fatty tissue can be separated and identified (Ng et al. 1993; Landini et al. 1986; Barzilai et al. 1987; Picano et al. 1988; Jones et al. 1989) using ultrasound imaging techniques developed for plaque component characterization. These diagnostic techniques are difficult to perform in vivo and they are not robust enough to provide consistent and reproducible differentiation of thrombus or plaque components. One alternative method is to use targeted ultrasonic contrast agents to highlight thrombus/atheroma components. Echogenic immunoliposomes (ELIP) can help provide this information. Liposomes, or phospholipid bilayer vesicles enclosing gas and fluid, are novel agents that may permit evaluation of vasoactive and pathologic endothelium. Since first examined by Bangham et al. (1965), liposomes have been developed for a wide range of technical and medical applications. Echogenic liposomal dispersions can be prepared by dispersing a lipid in water, adding manitol, freezing and drying, or lyophilizing (Alkan-Onyuksel et al. 1996; Huang et al. 2001). The echogenicity of these preparations is due to the presence of gas, which is entrapped and stabilized by the lipid during the rehydration process following lyophilization (Huang et al. 2002a).

Echogenic immunoliposomes can be targeted to certain tissues by attaching specific ligands and antibodies to the surface of liposomes (Martin et al. 1990; Leonetti et al. 1990). For example, ELIP coupled to anti-VCAM-1 or anti-ICAM-1 antibodies could be used to identify pathologic endothelium at early stages of atherosclerosis development. Similarly, the linkage of a liposome with antifibrin or D-dimer antibody may identify and highlight thrombus/plaque rupture. Initial studies in the laboratory of Dr. David McPherson demonstrated conjugation of anti-fibrinogen antibodies (which fully cross-react with fibrin). These conjugated liposomes retained their acoustic properties and associated specifically with fibrinogen-coated slides and fibrin thrombus, which was demonstrated by direct microscopic observation and enhanced ultrasound imaging of targeted surfaces (Murer et al. 1995; Hamilton et al. 2002). Lanza et al. (1996) have also demonstrated with a different lipid formulation that a multi-step acoustic biotinylated, lipid-coated, perfluorocarbon nanoemulsion could be successfully targeted to thrombi in vivo while maintaining ultrasound contrast. They have additionally demonstrated that this ultrasound agent can infiltrate arterial walls and localize tissue factor expression (Lanza et al. 2000). Unger et al. (1992, 1998) created targeted microbubbles containing perfluorobutane (aerosomes) that were approximately 2 μm and were able to bind to thrombus in vitro. A further benefit of echogenic immunoliposomes is that they have the potential for drug encapsulation for targeted therapeutic delivery.

Providing efficient and safe methods for the delivery of drugs to target cells is the principal goal of a clinically useful pharmacotherapeutic strategy. When a pharmaceutic is administered systemically, only a small fraction of the drug may actually reach the target tissue, with the necessity of large total doses to achieve effective local concentrations. Hence, systemic toxicity is usually the dose-limiting factor (Groothius 2000). Regional pharmacotherapeutic delivery has distinct advantages, which include increased concentrations at the specific tissue site and decreased toxicities (Eccleston et al. 1996). Direct delivery of a drug to the target organ results in a high ratio of local to systemic bioavailability, with the result of a decreased required total dose. As such, specific delivery may result in increased tolerable local concentrations of the drug. There is increasing interest in regional drug delivery. In stroke, the high concentrations of recombinant tissue plasminogen activator (rt-PA) required systemically to dissolve thrombi creates the potential of disastrous sequelae (large intracerebral hemorrhage) if given at a non therapeutic part of the stroke process. A targeted carrier that could maximize site delivery while providing the ability to react with ultrasound to optimize regional delivery is very attractive.

Carriers used for the local delivery of drugs may be classified as nonbiodegradable, such as polymethylmethacrylate (PMMA) beads, or biodegradable, such as polylactate polymers and liposomes (Kanellakopoulou and Giamarellos-Bourboulis 2000). Liposomes have further advantages in that they can be manipulated to interact with and entrap biological structures. The multilamellar vesicles may also act as microreservoirs, prolonging regional release of active ingredients (Grayson et al. 1993; Kim et al. 1987). Additional benefits of liposomes are that lipids are small molecular structures and the liposome/lipid complexes can made smaller by filtering or sonication techniques. Proteins and delivery agents made of proteins tend to break if they are manipulated to make them smaller. The difference lies in the rigidity of the proteins, which have covalent bonds, versus the lipids, which are small molecules held together by hydrophobic interactions [an example would be the rigidity of mayonnaise (a lipid formulation) vs. a hard boiled egg (a protein formulation)]. In collaboration with Dr. McPherson, the laboratory of Dr. Robert C. MacDonald has been able to alter flexibility and rigidity of these liposomal formulations, further improving the ability of liposomes to be modified for clinical delivery of anti-thrombotic agents (Huang et al. 2001, 2002a).

The use of liposomes as a drug delivery agent is increasingly being explored. Liposomes are ideal targeted delivery systems as they are nontoxic and can carry either hydrophilic or hydrophobic compounds either in the aqueous compartment or within the phospholipid bilayers and can be targeted to specific tissues (see above). Hence, the development of a liposome-drug delivery mechanism that can be manipulated for site-specific tissue targeting may provide improved specificity of drug delivery and more efficient and enduring effects at the target site.

Exciting work in the field of therapeutics demonstrates enhanced cell delivery/transfection with the use of low-level ultrasonography (Kim et al. 1996; Huber and Pfisterer 2000). It has been suggested that this increased uptake is due to cavitation effects by ultrasound (Koch et al. 2000), a theory supported by the finding that inclusion of Albunex (an imaging contrast agent, precursor to Optison®) as a cavitation nucleation agent enhances ultrasound-induced delivery/transfection (Greenleaf et al. 1998).

Extending this concept, we have demonstrated that the interaction of ultrasound and our echogenic immunoliposomes can likewise enhance drug delivery to target pathological sites. Although air-containing contrast agents and cationic lipids have been used in conjunction with ultrasound for enhanced transfection, we have demonstrated further enhancement of transfection using our echogenic immunoliposomes (in conjunction with low-level ultrasonography) compared with nonacoustic cationic lipids (Huang et al. 2002b,c). This invention utilizes the effect of ultrasound as it interacts with echogenic liposomes for drug delivery to thrombus and ischemic stroke. These formulations provide an entirely new approach to targeted therapeutic delivery.

Recent clinical studies have demonstrated improved thrombolysis with the concomitant use of focused ultrasound and a thrombolytic agent for stroke and acute myocardial infarction (Alexandrov et al. 2004; Cohen et al. 2003; Eggers et al. 2003). Suggested mechanisms include rectified diffusion which promotes transport of drugs into the thrombus, reformation and opening of the fibrin matrix which enhances drug diffusion, cleaving of fibrin polymers to extend the surface for drug interaction, and direct effects on binding of the agent to fibrin (Daffertshofer 2003). Ultrasound waves generate cavitation effects, which allow large molecules and particles to penetrate cells (sonoporation) (Koch et al. 2000; Miller et al. 1996), and this property is actively being investigated for drug and gene delivery (Saad and Hahn 1992; Kim et al. 1996; Bao et al. 1997; Tachibana and Tachibana 2001). Addition of a contrast agent as a nucleation agent can lower the threshold for these ultrasound bioeffects (Miller et al. 1996; Birnbaum et al. 1998; Greenleaf et al. 1998; Ward et al. 1999).

The concept of a liposome-encapsulated tPA retaining its fibrin-targeting ability and thrombolytic capacity, or being able to release free tPA upon sonication is non-obvious, since tPA is a hydrophobic protein. As such, it would be expected to be sequestered in the liposomal phospholipid bilayer. Contrary to this expectation, we have demonstrated that tPA behaves like a cellular transmembrane protein with fibrin-binding and catalytic sites fully exposed and active (Klegerman et al. 2006). The thrombolytic activity of the formulation is significantly enhanced by therapeutic sonication (Tiukinhoy-Laing et al. 2007).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Echogenic Liposomes Using a Lyophilization Methodology

This procedure describes methods and reagents required to make acoustically reflective, oligolamellar liposomes using a composition and method conducive to the production of antibody targeted vesicles. Freeze-drying is lyophilization.

Reagents:
1) Phosphatidylcholine, from egg yolk (PC) as an alcoholic solution
2) Cholesterol (Chol)
3) Phosphatidylethanolamine, dipalmitoyl (PE)

4) Deionized water
5) Cryoprotectant sugar (e.g. mannitol)
6) Tris HCl
7) Sodium Phosphate (dibasic)
8) Sodium Chloride Equipment:

1) Rotary evaporator with external cooling, vacuum and heating.
2) Probe sonicator and ear protection.
3) Submicron particle size analyzer (e.g. NICOMP (Pacific Scientific) Malvern) and tubes.
4) Volumetric flasks, graduated cylinders, syringes, hypodermic needles, repipets/pipets and liquid scintillation vials (25 & 10 mL).
5) Stirrer/heating plate and stir bars.
6) Electronic balance (accurate to 0.1 or 0.01 mg).
7) pH meter and calibration standards.
8) Ring stand and clamps.
9) NUCLEPORE (Costar Co.) filters and membranes in steps from 2 to 0.22 microns.
10) Bottle lyophilizer and associated equipment.
11) CVIS intravascular catheter system and 20 MHz imaging catheter.

Procedure:

1) Warm vials of phosphatidylcholine to room temperature.
2) Weigh (according to electronic scale instructions) 25 mg of cholesterol.
3) Dissolve cholesterol in 2.5 mL of dry chloroform and phosphatidylethanolamine in 2.0 ml of dry chloroform using sufficient warming to facilitate dissolution but avoiding excess heat.
4) Combine in a 250 mL rotoevaporator flask: 73 mg of phosphatidylcholine, 11 mg phosphatidylethanolamine and 16 mg of cholesterol. Adjust as required for scale-up.
5) Attach flask to pre-cooled (0 degrees Centigrade) rotary evaporator with a 50 degree Centigrade warming bath.
6) Rotate flask rapidly (approximately 210 rpm) and dry under vacuum.
7) After the film is dry, remove flask from rotoevaporator and place in desiccator under vacuum and cover desiccator with a dark cloth.
8) Continue to dry film under vacuum for 2 days.
9) Prepare 100 mM mannitol solution in deionized water.
10) Add 10 mL of mannitol solution per 100 mg of lipid.
11) Without significant agitation, place flask on rotoevaporator without coolant circulating, flood atmosphere with nitrogen and rotate the flask (approximately 210 rpm) to resuspend lipid film.
12) When lipid film is resuspended, add one or two drops of liposome suspension to NICOMP (Pacific Scientific) tube and dilute with 100 mM mannitol solution, sufficiently for analysis.
13) Analyze particle size with NICOMP (Pacific Scientific) according to manufacturer's instructions.
14) Transfer liposomes from round bottomed flask to 25 mL liquid scintillation vial with a pipet and cap.
15) Secure vial to ring stand and submerge vial approximately two-thirds into a cool tap-water bath to dissipate excess heat during sonication.
16) Remove cap and position sonicator probe into the vial being sure not to leave the probe in contact with the glass and maintaining the tip of the probe about one quarter inch above the bottom.
17) Set the sonicator for 10% duty and 10% power and sonicate for 3 minutes.
18) Recheck particle size as before with NICOMP (Pacific Scientific). Continue to reduce particle size using 1 minute sonication bursts at same power and with increasing duty levels until vesicles are less than 400 mn. Increase power and repeat duty changes starting at 10% if additional sonication is required.
19) Transfer approximately 5 mL aliquots of liposome suspension into each of two 25 mL liquid scintillation vials, layer with nitrogen, and cap.
20) Either snap-freeze in acetone-alcohol-dry ice bath or freeze overnight in −70 Centigrade deep freezer.
21) Transfer vials from the freezer to the lyophilizer jars and freeze dry according to manufacturer's instructions for approximately 48 hours.
22) After 48 hours of lyophilization, remove vials from the freeze dryer, gently overlay contents with nitrogen, recap and seal vials with parafilm.
23) Store vials in refrigerator with desiccant up to 72 hours until use.
24) Prepare 0.10M Tris HCl+0.10M NaCl, pH 7.5 buffer.
25) To rehydrate, add 0.10 mM Tris HCl+0.10 mM NaCl, pH 7.5, buffer to each vial. A good starting volume is 2-3 mL of buffer/mL of the desired liposome lyophilized.
26) Size liposomes with the NICOMP (Pacific Scientific) submicron particle analyzer as previously discussed.
27) Transfer liposome suspension to an appropriately sized syringe and extrude liposomes to desired particle size through polycarbonate membranes according to manufacturer's instructions until desired size is attained. Excessive extrusion will significantly destroy liposome structure and diminish echogenicity. If initial particle size is more than 1-2 microns above desired range, repeat procedure using a greater post-lyophilization dilution factor to attain a smaller initial vesicle size. Be sure sample for size analysis dilution buffer is iso-osmotic with liposome solution (300 milliosmoles) to avoid artifactual swelling or contraction of vesicles and inaccurate size estimation.
28) Transfer liposomes into small (10 mL) liquid scintillation vials and image liposome suspension with 20 MHz cm CVIS intravascular imaging catheter system.

Reference:

New, R. R., 1990, Liposomes: A Practical Approach. Oxford University Press. (hereby incorporated by reference).

Example 2

A. SPDP Derivitization of Phosphatidylethanolamine

The following procedures described methods to produce an N-succinimidyl pyridyl dithiopropionate (SPDP) derivitization of IgG antibody and phosphatidylethanolamine and their incorporation into a process for producing acoustically reflective liposomes as described in Example 1. This procedure describes methods and reagents required to make N-succinimidyl pyridyl dithiopropionate derivatives of phosphatidylethanolamine for incorporation into liposomes for antibody coupling reaction.

Reagents:

1) L-a-phosphatidylethanolamine, dimyristoyl or dipalmitoyl, 99% purity (PE)
2) Triethylamine (TEA)
3) N-sucinimidyl pyridyl dithiopropionate
4) Nitrogen
5) Silicic Acid
6) Methanol
7) Chloroform
8) Dodecamolybdophosphoric acid 9) Silica thin layer chromatography (TLC) plates Equipment:
1) Liquid scintillation vial or test tube with cap
2) Stirrer/heating plate and stir bars
3) 20 cc plastic syringe barrel with glass fiber plug
4) Fraction collector or test tube rack
5) TLC developing tank with filter paper lining
6) Electronic balance (accurate to 0.1 or 0.01 mg)
7) Graduated cylinders, repipets/pipets
8) Ring stand and clamps
9) Atomizer sprayer and spray box
10) Rotary evaporator with external cooling, vacuum, heating and 250 mL flasks.
11) Hamilton microliter syringe with lock Procedure:
1) Weigh 15 mg of PE, 10 mg of SPDP, 2 g silicic acid, 3 g dodecamolybdophosphoric acid.
2) Dissolve PE in a liquid scintillation vial in approximately 2 mL chloroform using sufficient warming to facilitate dissolution but avoiding excess heat.
3) Dry PE under continuous nitrogen stream or with rotoevaporation.
4) Resuspend PE in 2.0 mL of chloroform.
5) Dissolve 200 microliters TEA in 25 mL methanol (2.9 mg/0.5 mL).
6) Dissolve 10 mg SPDP in 0.5 mL methanol with slight supplemental heating.
7) Add 0.5 mL TEA (2.9 mg) to PE in vial.
8) Add 0.5 mL SPDP (10 mg) to PE and TEA.
9) Add small stirring bar to vial.
10) Saturate atmosphere in vial with nitrogen and cap.
11) Stir mixture at room temperature for 2 hours.
12) In a 250 mL or greater flask add 130 mL of chloroform, 50 ml of methanol, and 10 ml of deionized water.
13) If solution is cloudy add 1-2 mL additional methanol to dry.
14) Add approximately half of the solution to the developing tank.
15) Cover tank and allow atmosphere and filter paper lining to saturate with solvents.
16) Slurry 2 g of silicic acid in 10-12 mL of chloroform.
17) Pour silicic acid slurry into syringe barrel supported on a ring stand.
18) Allow excess solvent to drain but do not allow column to dry.
19) Prepare phosphomolybdate spray by dissolving 3 g of dodecamolybdophosphoric acid in 10 mL of ethanol or reagent grade alcohol.
20) Place in sprayer and wrap sprayer in foil to blockout light until use.
21) After 2 hours check reaction by spotting (10 microliters) the reaction mixture and pure phosphatidylethanolamine standards with a Hamilton syringe onto the thin layer chromatography plate.
22) When the solvent line on TLC plate is approximately 1.0 cm from the top, remove the plate from the tank and air dry.
23) In a hood, spray dry plate with a light, even coat of phosphomolybdate spray.
24) Warm plate on a hot plate with low heat to develop black spots (100 degrees Centigrade). The test is qualitative. Derivatized phosphatidylethanolamine migrates faster than the pure standard lipid. The reaction is usually 100% complete. If the reaction is incomplete, add 1 mg of TEA and allow reaction to continue 30-60 minutes and recheck with thin layer chromatography.
25) When the reaction is complete, add mixture to silicic acid column and wash in with 4.0 mL chloroform.
26) Elute derivatized phosphatidylethanolamine in 2.0 mL fractions using 4.0 mL aliquots of the following chloroform:methanol solutions gradient: 4.0:0.25, 4.0:0.50 4.0:0.75, 4.0:1.0, 4.0:1.25, 4.0:1.5, 4.0:1.75, 4.0:2.0. Repeat 4.0:2.0 to ensure complete elution.
27) Layer each fraction with nitrogen after collection to inhibit oxidation.
28) Identify fractions with phosphatidylethanolamine derivative by thin layer chromatography as before.
29) Pool fractions containing derivative into a rotoevaporator flask.
30) Attach flask to rotoevaporator previously cooled with circulating cold water or coolant.
31) Dry derivative to a film and resuspend in 3.0 cc of chloroform.
32) With thin layer chromatography roughly quantitate phosphatidylethanolamine derivative concentration by comparing 15 .mu.L, 10 .mu.L, and 5 .mu.L spots of standard PE of known concentration to equal volumes of the derivative solution. Determine mg/mL of derivative.

B. N-succinimidyl Pyridyl Dithiopropionate Derivitization of IgG Antibody

This procedure describes the N-succinimidyl pyridyl dithiopropionate derivitization of IgG antibody for conjugation with similarly modified liposomes.

Reagents:
1) N-succinimidyl pyridyl dithiopropionate (SPDP)
2) Sodium citrate
3) Anhydrous sodium phosphate, dibasic
4) Sodium chloride
5) Sephadex G-50
6) Ethanol or reagent grade alcohol
7) IgG antibody
8) BCA protein binding dye concentrate (BCA)
9) Dithiothreitol
10) Deionized water
11) Sodium acetate
12) Nitrogen
13) Dilute hydrochloric acid (HCl)
14) Glacial acetic acid (17.4M)
15) Anhydrous potassium phosphate, monobasic Equipment:
1) UV/VIS Spectrophotometer
2) 100 mL Gel Chromatography column and tubing
3) Fraction collector
4) Micropipets
5) Hamilton syringe (5-10 .mu.L capacity)
6) Pasteur pipets
7) Beaker/flasks various sizes
8) Stirrer and stir bars
9) Analytical balance (accurate to 0.1 or 0.01 mg)
10) pH meter with micro and regular electrodes and appropriate standards
11) Ring stand and clamps
12) Amicon ultrafiltration system
13) Volumetric flasks Procedure:
1) Combine 19.7 g sodium citrate, 7.1 g anhydrous sodium phosphate, dibasic ($Na_2HOP_4$), and 2.9 g sodium chloride per liter in a 1 or 2 liter beaker and fill 75% with highly purified, deionized water. Usually prepare 2 L of buffer.
2) Adjust pH to 7.0 using dilute hydrochloric acid.

3) Transfer pH 7.0 buffer to volumetric flask with three washes of the beaker and fill to the mark with deionized water.

4) Weight 7.5 g of SEPHADEX G-50 (Pharmacial Co.) and transfer to a 125 mL beaker.

5) Add 100 mL of citrate/phosphate buffer (step 1) to the beaker, cover and allow gel to swell at least 3 hours, preferably overnight.

6) After swelling, decant excess citrate/phosphate buffer and fines and resuspend gel in 100 mL of fresh buffer.

7) Assemble gel chromatography system.

8) Place 10 mL of citrate/phosphate buffer in base of column.

9) Load gel slurry into column as a continuous pour while draining excess buffer out of the column.

10) After column is poured, allow gel to settle.

11) Pass 10 bed volumes (approximately 750 mL) of citrate/phosphate buffer through the column and seal for use the next day. (Add 0.01% sodium azide to elution buffer if storing the column for more than 24 hrs).

12) The next day, drain excess buffer from the top of the column, leaving 5 mL above gel.

13) Prepare 0.1M phosphate buffer, pH 7.5, by mixing 1.361 g anhydrous potassium phosphate, monobasic ($KH_2PO_4$), in 90 mL of deionized water, titrate to pH 7.5, transfer to a 100 mL volumetric flask and fill to the mark with deionized water.

14) Prepare 0.5M acetic acid by diluting 2.0 mL of concentrated acetic acid (17.4M) with 67.6 mL deionized water.

15) Prepare 6 mg N-succinimidyl pyridyl dithiopropionate in 1.0 mL 30% ethanol.

16) Weigh 165 mg sodium acetate, combine with 10 mL deionized water and titrate to pH 5.5.

17) Weigh 95 mg dithiothreitol and dissolve in 250 microliters of sodium acetate buffer in a microcentrifuge tube.

18) Dissolve IgG antibody (e.g. 25 mg) in 0.1M phosphate buffer (pH 7.5) at a concentration of 5 mg/mL.

19) Add 150 microliters of N-succinimidyl pyridyl dithiopropionate in 30% ethanol while stirring slowly, and continue stirring for 30 minutes.

20) Slowly decrease the pH (dropwise) of the antibody solution to pH 5.5 with 0.5M acetic acid.

21) Add 50 microliters of dithiothreitol, cover solution with nitrogen and allow to stand 1 hour.

22) Drop the buffer level over SEPHADEX (Pharmacia) column to top of column and slowly add IgG mixture.

23) Run IgG into column and wash in with 2-3 mL citrate/phosphate buffer.

24) Fill column to top with buffer previously purged of oxygen with nitrogen, careful not to disturb column, and attach buffer reservoir layered with nitrogen or argon or continuously bubble nitrogen through the elution buffer.

25) Elute column at 0.5 to 1.0 mL/min.

26) Layer each fraction with nitrogen or argon to avoid oxidation of sulfhydryl groups.

27) Assay fraction on spectrophotometer at 280 nm and note protein peaks. Usually, two peaks are detected but the first protein peak is used. The second peak is probably immunoglobulin fragments, though no confirmatory electrophoresis has been performed.

28) Combine fractions of high optical density and conduct a BCA protein assay according to manufacturer's instructions to estimate protein concentration.

29) If the protein concentration is too dilute, to concentrate antibody under nitrogen or argon with Amicon ultrafiltration system according to the manufacturer's instructions.

30) Combine antibody with liposomes as previously discussed and proceed with conjugation.

C. Production of Echogenic Antibody-conjugated Liposomes Using a Freeze-drying Methodology This procedure describes methods and reagents required to make acoustically reflective, oligovesicular liposomes conjugated to IgG antibodies through a disulfide bridge using N-succinimidyl pyridyl dithiopropionate derivatives of phosphatidylethanolamine and antibody.

Reagents:
1) SPDP derivatized L-a-phosphatidylethanolamine (PE-PDP)
2) Phosphatidylcholine (PC)
3) Cholesterol (Chol)
4) Phosphotidylglycerol (PG)
5) Deionized water
6) Mannitol
7) Sodium citrate
8) Sodium phosphate (dibasic)
9) Sodium chloride
10) Reagent grade alcohol
11) Biogel A-5M (100-200 Mesh)

Equipment:
1) Rotary evaporator with external cooling, vacuum and heating
2) Probe sonicator and ear protection
3) Submicron particle size analyzer (e.g. Malvern, Coulter) and tubes
4) Fraction collector or test tube rack
5) Volumetric flasks
6) Stirrer/heating plate and stir bars
7) Electronic balance (accurate to 0.1 or 0.01 mg)
8) Liquid scintilation vial or suitable substitute
9) Graduated cylinders10) Repipets/pipets
11) Ring stand and clamps
12) NUCLEPORE (Costar Co.) filters and membranes from 2 to 0.22 microns Procedure:
1) Warm vials of phosphatidylcholine to room temperature.
2) Weigh 25 mg of cholesterol.
3) Dissolve cholesterol in 2.5 mL of chloroform.
4) Transfer to a rotoevaporator by pipet 73 mg of phosphatidylcholine, 11 mg derivatized phosphatidylethanolamine, 16 mg cholesterol. Adjust as required for scale-up.
5) Attach flask to 0 degree centigrade pre-cooled rotoevaporator with 50 degree centigrade warming bath.
6) Dry lipid film under vacuum at rotational speed of approximately 210 rpm.
7) Remove flask from rotary evaporator and place in desiccator under vacuum and cover desiccator with a dark cloth.
8) Dry film for 2 days.
9) Prepare 100 mM mannitol solution in deionized water.
10) Add 10 mL of mannitol solution per 100 mg of lipid.
11) Rotate the flask at 210 rpm to resuspend lipid film.
12) When lipid film is resuspended, add one to two drops to NICOMP tube and dilute with 100 mM sugar water solution.
13) Analyze particle size.
14) Transfer liposomes from round bottomed flask to liquid scintillation vial.

15) Secure vial to ring stand and submerge vial approximately two-thirds into cool tap water flask to dissipate excess heat during sonication.

16) Position sonicator probe about one quarter inch above the flask bottom and not in contact with the glass vial.

17) Set the sonicator for 10% duty and 10% power and sonicate for 3 minutes.

18) Recheck particle size. Continue to reduce particle size using 1 minute sonication bursts at same power and with increasing duty levels until vesicles are less than 400 nm. Increase power and repeat duty changes starting at 10% if additional sonication is required.

19) Derivatize antibody as previously described.

20) To conjugate reduced antibody to liposomes, combine liposomes with reduced, derivatized protein to have a coupling ratio (.mu.g protein/.mu.mol lipid-0.6 mg protein/.mu.mol lipid) of 390-500 and a final protein concentration of approximately 0.5 mg/mL. Buffer associated with protein should provide sufficient buffering capacity to maintain pH at 7.0 at a minimal ionic strength.

21) Allow antibody conjugation to proceed for 12-18 hours.

22) Fill chromatography column with gel at a ratio of at least 10 mL of BIOGEL-A 5M (100-200 mesh) to 1 mL of liposome suspension. Put 10 mL of buffer in column before adding gel and then fill the column while slowly running out the excess buffer.

23) Elute Biogel-A-5m column with 10 bed volumes of 100 mM mannitol solution the day before use.

24) After antibody conjugation, pass liposomes through sequentially smaller (2 to 0.22 micron) NUCLEPORE (Costar Co.) polycarbonate filters as required to reduce particle size below 400 nm. Verify final particle size.

25) Drain excess buffer from column.

26) Gently and slowly load liposome suspension to top of column with a Pasteur pipet.

27) Slowly run liposomes into column, stopping the flow when the liposomes have just completely entered the top of the column. Do not allow the column to dry.

28) Wash liposomes off the sides of column with 2-3 mL of mannitol solution then run this into the column.

29) Slowly fill the column with 100 mM mannitol solution containing 0.01M potassium phosphate buffer, pH 7.0 being careful not to disturb the top of the gel column.

30) When the column is full of buffer, attach the buffer reservoir to the column with tubing.

31) Attach column to fraction collector with sufficient tubes to collect 3 bed volumes. Liposomes will come out in the void volume and unbound antibody will follow close behind.

32) Collect fractions at a rate of 0.5-1.0 mL/min for best resolution.

33) Analyze fractions for particles using the NICOMP at maximum photopulse to isolate liposomes and a spectrophotometer at 280 nm to isolate protein fractions.

34) Pool fractions containing both liposomes and protein.

35) Concentrate liposomes to approximately 10 mg of lipid per mL using an appropriately sized Amicon ultrafiltration system (300 KDa membranes) according to the manufacturer's instructions.

36) Transfer 5 mL aliquots of liposomes into 25 mL liquid scintillation vials, layer with nitrogen and cap.

37) Either snap-freeze in acetone-alcohol-dry ice bath or freeze overnight in −70 degree centigrade deep freezer.

38) Transfer vials from the freezer to the lyophilizer jars and freeze dry for 48 hours according to the manufacturer's instructions.

39) After 48 hours of lyophilization, remove vials from the freeze dryer, gently layer contents with nitrogen, recap and seal with parafilm.

40) Store vials in refrigerator with desiccant until use within 72 hours.

41) Prepare 0.10M Tris HCl+0.10M NaCl, pH 7.5, buffer.

42) To rehydrate, add 0.10 mM Tris HCl+0.10 mM NaCl, pH 7.5, buffer to each vial. The initial liposome size will vary inversely with the volume of buffer added. A good starting volume is 2-3 mL of buffer/mL lyophilized liposome containing sufficient amount of ions to make a solution of the same osmolarity/mL of liposome suspension lyophilized.

43) Size liposomes with submicron particle analyzer.

44) Transfer liposome suspension to an appropriately sized syringe and extrude liposomes to desired particle size through polycarbonate membranes according to manufacturer's instruction until desired size is attained. Note: Excessive extrusion will significantly destroy liposome structure and diminish echogenicity. Be sure sample dilution buffer size analysis is iso-osmotic with liposome solution to avoid artifactual swelling or contraction of vesicles and inaccurate size estimation.

45) Transfer liposomes into small 10 mL liquid scintillation vials and image liposome suspension with 20 MHz CVIS intravascular imaging catheter system.

Example 3

Liposomes of four different compositions were prepared in triplicate using the procedures outlined in Example 1 (without the optional addition of mannitol cryopotectant) and imaged with a 20 MHz intravascular catheter to identify echogenicity. Two replicates were ultrasonically analyzed pre and post extrusion and the results of an overall split-plot statistical analysis y=rep+composition+rep*composition+time+composition*time+residual, where rep*composition was used to test composition effects and residual error was used to test time effects (time equating to pre versus post polycarbonate extrusion). Least-square means for the composition effect for the above model are presented.

| Composition | Liposome Mean Gray Scale | Liposome Gray Scale Heterogeneity |
|---|---|---|
| PC | 3.31 | 3.34 |
| PC:CH | 9.82 | 8.33 |
| PC:PE | 21.68* | 11.94* |
| PC:PE:CH | 23.85* | 13.86* |

*PC vs other combination (p .ltoreq. 0.05)

In this study, change in solution acoustic reflectivity was quantitated as the increased pixel brightness (gray scale) of liposome clusters compared with background levels and the increase in pixel heterogeneity of the overall liposome/buffer image. Liposomes incorporating phosphatidylethanolamine were ultrasonically visible before and after extrusion to reduced particle sizes and this was reflected as a statistically significant increase in pixel gray scale and heterogeneity. Phosphatidylcholine: cholesterol vesicles were echogenic before but not after extrusion.

Example 4

Abstract

Introduction

Targeted delivery of thrombolytics to the site of occlusion is an attractive concept, with implications for the treatment of many thrombo-occlusive diseases. Ultrasound enhances thrombolysis, which can be augmented by the addition of a contrast agent. We have previously reported development of echogenic liposomes (ELIP) for targeted highlighting of structures with potential for drug and gene delivery. This study evaluated the potential of ELIP for thrombolytic loading, and the effect of ultrasound exposure of thrombolytic-loaded ELIP on thrombolytic efficacy.

Materials and Methods

Tissue-plasminogen activator (tPA) was loaded into ELIP. Echogenicity was assessed and reported as mean grayscale values. Whole porcine clots were treated with plasma, free tPA, tPA+Optison® (echocontrast agent), or tPA-loaded ELIP, with and without ultrasound (1 MHz, continuous wave, 2 W/cm$^2$, for 2 min). Clots were weighed before and after a 30-min treatment period, and results reported as percent clot mass loss.

Results tPA entrapment into ELIP was feasible with 50% entrapment, and retention of echogenicity. Treatment with tPA-loaded ELIP resulted in effective clot lysis with an effect similar to treatment with free tPA. Ultrasound exposure of tPA-loaded ELIP resulted in enhanced thrombolysis (49.5% relative improvement vs. no ultrasound). Much of the ultrasound effect appeared to be related to drug release from the tPA-ELIP complex.

Conclusions

We have demonstrated entrapment of tPA into ELIP with effective clot lysis and drug release using ultrasound. Our tPA-loaded ELIP has potential for specific highlighting of clots to confirm agent delivery and help focus ultrasound therapy for targeted ultrasound-facilitated thrombolysis.

The acute manifestations of myocardial infarction and stroke often relate to the rupture of an unstable plaque with platelet activation and thrombus formation [1]. The use of thrombolytic agents for the treatment of acute ischemic and neurologic events is limited in many patients by the potential nonspecific activation of plasminogen at sites other than the occluded vessel. Targeted delivery of a thrombolytic agent to the site of occlusion is an attractive concept, with implications for the treatment of many thrombo-occlusive diseases.

Recent clinical studies have demonstrated improved thrombolysis with the concomitant use of focused ultrasound and a thrombolytic agent for stroke and acute myocardial infarction [2], [3] and [4]. Suggested mechanisms include acoustic streaming which promotes transport of drugs into the thrombus, radiation force which might facilitate reformation and opening of the fibrin matrix enhancing drug diffusion, cleaving of fibrin polymers to extend the surface for drug interaction, and direct effects on binding of the agent to fibrin [5]. Ultrasound can also generate cavitation, which can cause large molecules and particles to penetrate cells (sonoporation) [6] and [7]; this property is actively being investigated for drug and gene delivery [8], [9], [10] and [11]. Addition of a contrast agent as a cavitation nucleation agent can lower the threshold for these ultrasound bioeffects [6], [12], [13] and [14].

We have previously reported development of echogenic liposomes (ELIP) for the targeted highlighting of structures [15] and [16] with potential for drug and gene delivery [17], [18] and [19]. This study aimed to explore the potential of ELIP for thrombolytic loading, and to evaluate the effect of directed ultrasound exposure of the thrombolytic-loaded ELIP on effecting drug release and promoting thrombolysis. Development of such methodology would represent a novel therapeutic strategy for the local delivery of thrombolytic agents for acute myocardial infarction and stroke.

Materials and Methods

Liposome Formulation

ELIP were prepared by the sonication-lyophilization-rehydration method as described previously [20]. Liposomal composition used was DPPC/DOPC/DPPG/Chol in a 46:24:24:6 molar ratio (DPPC=dipalmitoylphosphatidylcholine; DOPC=dioleoylphosphatidylcholine; DPPG=dipalmitoylphosphatidylglycerol; Chol=Cholesterol). The component lipids were dissolved in chloroform and the solvent was allowed to evaporate completely. The resulting lipid film was placed under vacuum for full removal of the solvent and then hydrated with distilled, deionized water. This dispersion was sonicated for 5 min. 0.2 M D-mannitol was added to the liposome suspension and the sample was frozen at −70° C. The samples were lyophilized for 48 h and resuspended with 0.1 M phosphate-buffered saline (PBS). The final concentration used for dilution was 10 mg lipid/ml PBS.

Drug Incorporation

Recombinant tissue-plasminogen activator (tPA) (Activase®, Genentech Inc., San Francisco, Calif.) was used as the thrombolytic agent. For the drug-loaded ELIP preparation, 1 mg/ml tPA solution was used for the initial rehydration of the lipid film. Entrapped tPA was separated from the free tPA by centrifugation at 16,000 rpm for 10 min at 37° C. As used by Heeremans et al. [21], "entrapped" tPA in this study refers to both the tPA associated with the lipid bilayer, as well as full encapsulation of the drug within the liposomal aqueous phase. A tPA chromogenic substrate (Sigma, St. Louis, Mo.) was used to evaluate tPA activity and quantitate drug loading into the ELIP. Briefly, 10 µl of resuspended ELIP were added to 970 µl assay buffer containing 30 mM Tris-HCl (pH 8.4) and 130 nM NaCl, in a cuvette. 50 µl of 4 mM chromogenic substrate solution (Sigma, St. Louis, Mo.) was then added to the ELIP-assay buffer mixture. Absorbance at 405 nm was measured using a spectrophotometer within 5 min of adding the substrate. Thrombolytic activity was measured before centrifugation ($F_c$), as well as before ($F_b$) and after ($F_a$) the addition of Triton X-100 (a detergent). Total percent tPA entrapment is defined as $F_a/F_c \times 100\%$, and percent tPA encapsulation is defined as $(F_a-F_b)/F_a \times 100\%$.

Echogenicity Analysis

The liposomes were imaged with a 20 MHz intravascular ultrasound catheter (SciMed, Inc., Sunnyvale, Calif.) in a 10-mm inner diameter glass vial, and a 3.5 MHz harmonic transthoracic probe (Acuson, Mountain View, Calif.) in an anechoic imaging well. Relative echogenicity (apparent brightness) of the liposome formulations was objectively assessed using computer-assisted videodensitometry. This process involves image acquisition, digitization, and grayscale quantification. All image processing and analyses were performed with Image Pro Plus Software (Ver. 1.0, Media Cybernetics, Silver Spring, Md.). Images were digitized to 640×480-pixel spatial resolution (approximately 0.045 mm/pixel) and 8-bit (256 level) amplitude resolution. Data are reported as mean grayscale values.

In Vitro Clot Formation

Whole porcine blood clots were used to evaluate thrombolysis [22]. Blood was obtained from non-heparinized Yucatan miniswine. The miniswine were 6-8 weeks old and weighed 28.5±6.5 lb. Baseline blood analysis data, including complete blood count, prothrombin time, activated partial thromboplastin time, D-dimer, and fibrinogen were obtained to ensure normal clotting parameters. Whole blood clots were made by aliquoting 1.5 ml fresh porcine blood into 1.3-cm inner diameter vacutainer tubes; the tubes were incubated in a 37° C. water bath for 3 h. The clots were then stored at 4° C. until use, which ensured complete clot maturation and retraction. This type of clot is fairly similar to physiologic venous clots. Most miniswine used in this study were slightly anemic (hematocrit of 27.8 ±3.0%). Only donors with values of <250 ng/ml for the D-dimer test, <15 s for prothrombin time, <18 s for activated partial thromboplastin time, and <300 mg/dl fibrinogen concentration were considered acceptable. The resulting clots were dark red, cylindrical, and weighed 0.47 ±0.11 g. All unused clots were discarded after 2 weeks.

Thrombolysis Studies

Whole porcine blood clots were blotted gently and weighed using an analytical balance. Each clot was placed in an acoustically transparent finger cot from a latex rubber glove containing 10 ml of freshly frozen porcine plasma (Animal Technologies, Inc., Tyler, Tex.), and placed in a holder within a 37° C. water bath. Ten units of human plasminogen (EMD Biosciences, Inc., La Jolla, Calif.) were added to each clot holder. Clots were treated with plasma alone (control), FLIP, tPA, or tPA-loaded ELIP. After 30 min, clots were taken out of the holder, blotted gently, and re-weighed. Triton X-100 was added to clots treated with tPA-loaded ELIP to investigate the effect of liposome destruction and total drug release from the tPA-ELIP complex. An echocontrast agent, Optison° (Mallinckrodt Inc., St. Louis, Mo.), which has been approved for clinical use in echocardiography, was also used to compare the effect of a different contrast agent on ultrasound-facilitated thrombolysis. Data are reported as percent clot mass loss (defined as the difference between the two clot weights obtained divided by the baseline clot weight).

Ultrasound Treatment

Porcine clots were treated with 1 MHz continuous wave (CW) ultrasound with an intensity of 2 W/cm$^2$, for 2 min (Sonitron 1000; Rich-Mar). The calculated peak negative acoustic pressure output was 0.12 MPa. Ultrasound was delivered in a water bath from a planar, non-focused, 1 MHz transducer (with an aperture of 1 cm), placed directly next to the finger cot sample holder.

Statistics

Results are reported as mean±S.D. (n=5). Multiple groups were compared using the analysis of variance (ANOVA) with pairwise multiple comparison performed using the Student-Newman-Keuls method. A p-value of less than 0.05 was considered significant. All analyses were performed using Sigma Stat software.

Results

Entrapment of tPA into ELIP was feasible. A maximum of 200±16 μg of tPA could be loaded per 8.2±0.6 mg of liposomal lipid. Entrapment efficiency was 50%. Of the 50% total tPA entrapped, 15% are fully encapsulated within the ELIP, whereas 35% are associated with the lipid bilayer. The tPA-loaded ELIP were echogenic, with a mean grayscale value of 155±27 (p<0.001 vs. PBS). However, echogenicity was lower when compared to unloaded ELIP (p<0.01). Nevertheless, these tPA-ELIP preparations are highly echogenic on ultrasound imaging, both at 20 MHz and 3.5 MHz (not shown).

The dose-response curve for the amount of free tPA used and the clot mass loss obtained showed increasing tPA dose resulted in increasing thrombolysis (not shown). For all subsequent experiments, 200 μg of tPA per clot experiment was chosen as the benchmark dose.

For each clot experiment, a total of 200 μg of tPA, 8.2 mg of liposomal lipid, and 1 ml of diluted Optison® were used. The tPA-ELIP complex resulted in effective thrombolysis, with an effect that is similar to treatment with free tPA (p>0.05). There was no significant thrombolysis when unloaded ELIP or Optison® were used without tPA (p>0.05 vs. Control). There was enhanced thrombolysis when a 2-min exposure to 1 MHz CW ultrasound was added to the 30-min treatment protocol, but only when tPA-loaded ELIP were present (p=0.02 vs. no ultrasound). There was no significant augmentation of thrombolysis when clots were exposed to ultrasound with free tPA or even when Optison® was added to free tPA (p>0.05 vs. no ultrasound). There was a 49.5% relative improvement in tPA-loaded ELIP thrombolytic effect when ultrasound exposure was added to the treatment protocol.

Much of the improvement in ultrasound-facilitated thrombolytic effect seen with the tPA-loaded ELIP appears to be related to drug release from the ELIP. The resultant thrombolysis measured when the detergent Triton X-100 was added to tPA-loaded ELIP treatment (to effect liposome destruction and hence, drug release) was lower although not statistically different from the treatment using tPA-loaded ELIP plus 2-min ultrasound exposure (p=0.211 vs. tPA-ELIP plus ultrasound).

Discussion

This study demonstrates ultrasound-facilitated thrombolysis using a novel thrombolytic-contrast agent complex. The novel concept presented involves entrapment of the thrombolytic drug in an acoustically-active agent with demonstration of drug release and enhanced drug effect by ultrasound treatment. This enhanced thrombolytic effect, in the presence of tPA-loaded ELIP, was seen even after only a brief 2-min exposure to 1 MHz CW ultrasound.

Ultrasound has been demonstrated to enhance thrombolysis when used in conjunction with a thrombolytic agent both in vitro and in vivo [23], [24], [25], [26] and [27]. Ultrasound delivered intravascularly through miniaturized transducers attached to a catheter has demonstrated effective and safe thrombolysis [28]. However, limitations include size of the device such that only proximal vessels can be treated, concern for distal embolization of large thrombus fragments, augmented permeability of distal ischemic vessels that may permit blood extravasation following recanalization in ischemic strokes, and the need for specialized facilities for selective arterial catheterization.

The noninvasive use of ultrasound to facilitate clot lysis with tPA was first demonstrated by Kudo and co-workers in 1989 [30]. In a canine model, they demonstrated that application of transcutaneous ultrasound near the site of an occluded femoral artery, when used in conjunction with tPA infusion, resulted in an 80% decrease in time for recanalization [30]. Similarly, in canine models of acute coronary occlusions, transcutaneous ultrasound augmented the efficacy of tPA-facilitated thrombolysis, regardless of whether the anterior or posterior coronary circulations were involved [31] and [32]. For the clinical application of noninvasive ultrasound therapy, it may be advantageous to determine the exact location-of the clot in order to selectively insonify the area of interest, thus limiting potential harmful bioeffects to surrounding tissues.

We have reported a novel technique to generate echogenic liposomes, which can be targeted to specific atheroma components [33]. We have demonstrated specific highlighting of atheroma with intraarterial injection of anti-intercellular adhesion molecule-1-conjugated ELIP [15], as well as targeted highlighting of a left ventricular thrombus with intravenous injection of anti-fibrinogen-conjugated ELIP [16]. We have also reported entrapment of an antibiotic and of reporter genes into these FLIP with demonstration of microbial growth inhibition and gene transfection, respectively, in cultured cells [17] and [18]. We have reported enhanced gene uptake and transfection with the addition of ultrasound treatment to the gene-bearing ELIP [19]. This study represents our first report of ultrasound-facilitated drug effect using our novel drug-loaded ELIP complex.

Ultrasound-triggered microbubble destruction has been investigated for targeted protein and gene delivery by other investigators [34] and [35]. The novel concept introduced in this study is the addition of another component to this technique, i.e., the use of a contrast agent as the drug delivery vehicle, with potential for highlighting the target site during drug delivery. Our novel tPA-loaded ELIP area echogenic, and can serve as both a contrast agent to highlight the clot and an ultrasound-releasable thrombolytic delivery agent. Hence, potentially, diagnostic ultrasound can be used to monitor and confirm attachment of the tPA-loaded ELIP to the clot, followed by therapeutic ultrasound pulses to trigger drug delivery.

Ultrasound-mediated thrombolysis may be enhanced by the addition of a contrast agent as cavitation nuclei [36], [37] and [38]. Though not to be bound by theory, we currently understand that the contrast agent adheres to the clot with resultant shearing effect during bubble destruction [13]. This mechanical erosion of the clot allows more fibrin to be exposed to the lytic agent [13]. The ultrasound-mediated effect improves with longer insonification times and/or use of fresh clots [25] and [39]. In this study, we chose to use older clots and shorter treatment times to provide more rigorous conditions to demonstrate lytic effect and proof-of-principle regarding the potential of these tPA-loaded ELIP as an ultrasound-releasable drug-delivery/contrast agent. Under these conditions (and the ultrasound parameters chosen), there was no significant enhancement in clot lysis by ultrasound either tPA alone or tPA plus Optison was used.

Though not to be bound by theory, we currently understand that much of the ultrasound effect observed in this study was probably due to release of the tPA from the liposomes. However, clot lysis with the use of Triton X-100 to effect liposome destruction was lower (albeit not statistically different) than the clot lysis observed with ultrasound plus tPA-loaded ELIP. This suggests that there may be other ultrasound bioeffects, which could have contributed to the additional clot lysis seen. Devcic-Kuhar et al. showed that ultrasound promoted the penetration of tPA into thrombi hence broadening the zone of lysis [40], while Braaten et al. showed that ultrasound exposure causes reversible disaggregation of uncrosslinked fibrin fibers which may create additional binding sites for thrombolysis [41]. Perhaps, longer insonification times, or the use of fresh clots would have resulted in even greater ultrasound-mediated thrombolysis through these other bioeffects. Nevertheless, the ultrasound treatment used in this study appeared to be sufficient to effect drug release from the tPA-ELIP complex.

Other investigators have demonstrated good correlation of fibrin-degradation products and percent clot mass loss as outcome endpoints to quantify the amount of thrombolysis [42].

In summary, we have demonstrated entrapment of tPA into a novel contrast agent (i.e., ELIP), with effective clot lysis and drug release using relatively short ultrasound treatment times. Our tPA-loaded ELIP are echogenic, with potential for specific highlighting of the clot to confirm agent delivery and focus ultrasound therapy.

Acknowledgment

We would like to acknowledge the invaluable help of Dr. Robert MacDonald for his expertise in liposome development; Bonnie Kane and Janet Martinez for blood draws from our animal models; and Devang Parikh and Kyle Buchanan for imaging of the liposomes. We would also like to acknowledge Sampada Vaidya at the University of Cincinnati for assistance with developing the whole blood porcine clot model.

REFERENCES

1. E. Falk, Unstable angina with fatal outcome: dynamic coronary thrombosis leading to infarction and/or sudden death, *Circulation* 71(1985), pp. 669-708.
2. A. V. Alexandrov, C. A. Molina, J. C. Grotta, Z. Garami, S. R. Ford, J. Alvarez-Sabin et al. and CLOTBUST Investigators, Ultrasound-enhanced systemic thrombolysis for acute ischemic stroke, *N Engl J Med* 351 (2004), pp. 2170-2178.
3. J. Eggers, B. Koch, K. Meyer, I. Konig and G. Seidel, Effect of ultrasound on thrombolysis of middle cerebral artery occlusion, *Ann Neurol* 53 (2003), pp. 797-800.
4. M. G. Cohen, E. Tuero, J. Bluguermann, R. Kevorkian, D. H. Berrocal and O. Carlevaro et al., Transcutaneous ultrasound-facilitated coronary thrombolysis during acute myocardial infarction, *Am J Cardiol* 92 (2003), pp. 454-457.
5. M. Daffertshofer and M. Hennerici, Ultrasound in the treatment of ischaemic stroke, *Lancet Neurol* 2 (2003) (5), pp. 283-290.
6. M. W. Miller, D. L. Miller and A. A. Brayman, A review of in vitro bioeffects of inertial ultrasonic from a mechanistic perspective, *Ultrasound Med Biol* 22 (1996), pp. 1131-1154.
7. S. Koch, P. Phol, U. Cobet and N. G. Rainov, Ultrasound enhancement of liposomemediated cell transfection is caused by cavitation effects, *Ultrasound Med Biol* 26 (2000), pp. 897-903.
8. H. J. Kim, J. F. Greenleaf, R. R. Kinnick, J. T. Bronk and M. E. Bolander, Ultrasoundmediated transfection of mammalian cells, *Hum Gene Ther* 7 (1996), pp. 1339-1346.
9. S. Bao, B. D. Thrall and D. L. Miller, Transfection of a reporter plasmid into cultured cells by sonoporation in vitro, *Ultrasound Med Biol* 23 (1997), pp. 953-959.
10. K. Tachibana and S. Tachibana, The use of ultrasound for drug delivery, *Echocardiography* 18 (2001), pp. 323-328.
11. A. H. Saad and G. M. Hahn, Ultrasound-enhanced effects of adriamycin against murine tumors, *Ultrasound Med Biol* 18 (1992), pp. 715-723.
12. W. J. Greenleaf, M. E. Bolander, G. Sarkar, M. B. Goldring and J. F. Greenleaf, Artificial cavitation nuclei significantly enhance acoustically induced cell transfection, *UltrasoundMed Biol* 24 (1998), pp. 587-595.
13. Y. Birnbaum, H. Luo, T. Nagai, M. C. Fishbein, T. M. Peterson and S. Li et al., Noninvasive in vivo clot dissolution without a thrombolytic drug: recanalization of thrombosed iliofemoral arteries by transcutaneous ultrasound combined with intravenous infusion of microbubbles, *Circulation* 97 (1998), pp. 130-134.
14. M. Ward, J. Wu and J. F. Chiu, Ultrasound-induced cell lysis and sonoporation enhanced by contrast agents, *JAcoust Soc Am* 105 (1999), pp. 2951-2957.
15. S. M. Demos, H. Alkan-Onyuksel, B. J. Kane, K. Ramani, A. Nagaraj and R. Greene et al., In-vivo targeting of acoustically reflective liposomes for intravascular ultrasonic enhancement, *JAm Coll Cardiol* 33 (1999), pp. 867-875.
16. Hamilton, S. L. Huang, D. Warrick, A. Stein, M. Rabbat and T. Madhav et al., Left ventricular thrombus enhancement following intravenous injection of echogenic immunoliposomes: studies in a new experimental model, *Circulation* 105 (2002), pp. 2772-2778.
17. S. Tiukinhoy, A. Khan, S. Huang, M. Klegerman, R. MacDonald and D. McPherson, Novel echogenic drug-immunoliposomes for drug delivery, *Invest Radiol*/39 (2004), pp. 104-110.
18. S. Tiukinhoy, M. Mahowald, V. Shively, A. Nagaraj, B. Kane and M. Klegerman et al., Development of echogenic, plasmid-incorporated, tissue-targeted cationic liposomes that can be used for directed gene delivery, *Invest Radiol*/12 (2000), pp. 732-738.
19. S. L. Huang, D. D. McPherson and R. C. MacDonald, Ultrasound in conjunction with an ultrasonic-reflective transfection agent enhances gene delivery to cells [abstr], *JAm Coll Cardiol* 39 (2002), p. 228A.
20. S. L. Huang, A. J. Hamilton, A. Nagaraj, S. D. Tiukinhoy, M. E. Klegerman and D. D. McPherson et al., Improving ultrasonic reflectivity and stability of echogenic liposomal dispersions for use as targeted ultrasound contrast agents, *J Pharm Sci* 90 (2001) (12), pp. 1917-1926.
21. J. L. Heeremans, H. R. Gerritsen, S. P. Meusen, F. W. Mijnheer, R. S. Gangaram Panday and R. Prevost et al., The preparation of tissue-type plasminogen activator (tPA) containing liposomes: entrapment efficiency and ultracentrifugation damage, *J Drug Target* 3 (1995), pp. 301-310.
22. C. K. Holland, S. S. Vaidya, C. C. Coussios and G. J. Shaw, Thrombolytic effects of 120 kHz and 1 MHz ultrasound and tissue plasminogen activator on porcine whole blood clots, *JAcoust Soc Am* 112 (2002), p. 2370.
23. K. Tachibana, Enhancement of thrombolysis with ultrasound energy, *J Vasc Intery Radiol* 3 (1992), pp. 299-303.
24. S. Behrens, K. Spengos, M. Daffertshofer, H. Schroeck, C. E. Dempfle and M. Hennerici, Transcranial ultrasound-improved thrombolysis: diagnostic vs. therapeutic ultrasound, *Ultrasound Med Biol* 27 (2001), pp. 1683-1689.
25. C. G. Lauer, R. Burge, D. B. Tang, B. G. Bass, E. R. Gomez and B. M. Alving, Effect of ultrasound on tissue-type plasminogen activator-induced thrombolysis, *Circulation* 86 (1992), pp. 1257-1264.
26. S. B. Olsson, B. Johansson, A. M. Nilsson, C. Olsson and A. Rouer, Enhancement of thrombolysis by ultrasound, *Ultrasound Med Biol* 20 (1994), pp. 375-382.
27. H. Luo, T. Nishioka, M. C. Fishbein, B. Cercek, J. S. Forrester and C. J. Kim et al., Myocardial ischemia/infarction/thrombolysis: transcutaneous ultrasound augments lysis of arterial thrombi in vivo, *Circulation* 94 (1996), pp. 775-778.
28. C. W. Hamm, W. Steffen, W. Terres, I. de Scheerder, J. Reimers and D. Cumberland et al., Intravascular therapeutic ultrasound thrombolysis in acute myocardial infarctions, *Circulation* 80 (1997), pp. 200-204.
29. [29] B. R. Mahon, G. M. Nesbit, S. L. Barnwell, W. Clark, T. R. Marotta and A. Weill et al. North American clinical experience with the EKOS MicroLysUS infusion catheter for ti e treatment of embolic stroke, *Am J Neuroradiol* 24 (2003), pp. 534-538.
30. S. Kudo, H. Furuhata, M. Hara, K. Maie, K. Hamano and T. Okamura, Noninvasive thrombolysis with ultrasound [abstr], *Circulation* 80 (1989) (Suppl. I), p. 1-345.
31. R. J. Siegel, S. Atar, M. C. Fishbein, A. V. Brasch, T. M. Peterson and T. Nagai et al., Noninvasive, transthoracic, low-frequency ultrasound augments thrombolysis in a canine model of acute myocardial infarction, *Circulation* 101 (2000) (17), pp. 2026-2029.
32. D. S. Jeon, H. Luo, M. C. Fishbein, T. Miyamoto, M. Horzewski and T. Iwami et al., Noninvasive transcutaneous ultrasound augments thrombolysis in the left circumflex artery—an in vivo canine study, *Thromb Res* 110 (2003), pp. 149-158.
33. H. Alkan-Onyuksel, S. E. Murer, G. M. Lanza, M. J. Vonesh, M. E. Klegerman and D. D. McPherson, Development of inherently echogenic liposomes as an ultrasonic contrast agent, *J Pharm Sci* 85 (1996), pp. 486-490.
34. R. Bekeredjian, S. Chen, P. A. Grayburn and R. V. Shohet, Augmentation of cardiac protein delivery using ultrasound targeted microbubble destruction, *Ultrasound Med Biol* 31 (2005) (5), pp. 687-691.
35. S. V. Pislaru, C. Pislaru, R. R. Kinnick, R. Singh, R. Gulati and J. F. Greenleaf et al., Optimization of ultrasound-mediated gene transfer: comparison of contrast agents and ultrasound modalities, *Eur Heart J* 24 (2003), pp. 1690-1698.
36. K. Tachibana and S. Tachibana, Albumin microbubble echo-contrast material as an enhancer for ultrasound accelerated thrombolysis, *Circulation* 92 (1995), pp. 1148-1150.
37. T. R. Porter, R. F. Le Veen, R. Fox, A. Kricsfeld and F. Xie, Thrombolytic enhancement with perfluorocarbon-exposed sonicated dextrose albumin microbubbles, *Am Heart J* 132 (1996), pp. 964-968.
38. T. Nishioka, H. Luo, M. C. Fishbein, B. Cercek, J. S. Forrester and C. J. Kim et al., Dissolution of thrombotic arterial occlusion by high intensity, low frequency ultrasound and dodecafluoropentane emulsion: an in vitro and in vivo study, *JAm Coll Cardiol* 30 (1997) (2), pp. 561-568.
39. H. Luo, W. Steffen, B. Cercek, S. Arunasalam, G. Maurer and R. J. Siegel, Enhancement of thrombolysis by external ultrasound, *Am Heart J* 125 (1993) (6), pp. 1564-1569.
40. B. Devcic-Kuhar, S. Pfaffenberger, L. Gherardini, C. Mayer, M. Groschl and C. Kaun et al., Ultrasound affects distribution of plasminogen and tissue-type plasminogen activator in whole blood clots in vitro, *Thromb Haemost* 92 (2004) (5), pp. 980-985.
41. J. V. Braaten, R. A. Goss and C. W. Francis, Ultrasound reversibly disaggregates fibrin fibers, *Thromb Haemost* 78 (1997) (3), pp. 1063-1068.
42. M. Kimura, S. Iijima, K. Kobayashi and H. Furuhata, Evaluation of the thrombolytic effect of tissue type plasminogen activator with ultrasonic irradiation: in vitro experiment involving assay of the fibrin degradation products from the clot, *Biol Pharm Bull* 17 (1994) (1), pp. 126-130.

Example 5

Abstract

We recently reported entrapment of tissue-plasminogen activator (tPA) into echogenic liposomes (ELIP) with retention of echogenicity and thrombolytic effect. Integral to the potential of this agent for ultrasound-detectable local drug delivery is the specific binding of tPA-ELIP to clots. tPA contains fibrin-binding sites; though not to be bound by theory, we currently understand that tPA when associated with ELIP, will maintain fibrin binding properties, rendering further manipulation for targeting of the tPA-ELIP unnecessary. We demonstrated strong fibrin binding of the ELIP-associated tPA. Fibrin binding for ELIP-associated tPA was twice that of free tPA. This strong affinity for fibrin was confirmed using echogenicity analysis of porcine clots in vitro. Both objective (mean gray scale analysis) and subjective (visual estimation by two experienced echocardiographers) evaluation of the clots showed enhanced highlighting of clots treated with tPA-ELIP when compared to control. The findings in this study represent new approaches for fibrin-targeted, ultrasound-directed and enhanced local delivery of a thrombolytic agent.

Introduction

Regional drug delivery has advantages over systemic therapy, including increased drug concentrations at the target sites and decreased toxicity (Eccleston et al. 1996). Liposomal carriers for the local delivery of drugs are actively being investigated and have been used successfully in clinical settings. Liposomes are closed concentric lipid bilayers alternating with internal aqueous compartments (Bangharn et al. 1965). We have previously reported development of echogenic liposomes (ELIP) as an ultrasound contrast agent for the targeted highlighting of structures (Demos et al. 1999; Hamilton et al. 2002). The echogenic property of our ELIP relates to spontaneous entrapment of air within the lipid bilayer (Huang at al. 2001). We have also previously reported the potential of our novel ELIP for drug and gene delivery (Tiukinhoy at al, 2000; Tiukinhoy et ai. 2004); by manipulation of size, structure and lipid composition, these ELIP can be loaded with drugs or genes with retention of echogenic properties.

Recently, we reported on the potential of our ELIP as an agent for ultrasound-releasable directed thrombolytic therapy (Tiukinhoy-Laing at al. 2006). We have demonstrated entrapment of a thrombolytic, tissue-plasminogen activator (tPA) into our ELIP with retention of ELIP echogenicity, as well as effective tPA lytic activity in an in vitro clot model. We also demonstrated that a short (2 min) duration of low frequency (1 MHz) continuous wave ultrasound treatment facilitated thrombolysis with most of the effect likely related to release of the tPA from the ELIP. Ultrasound probably breaks open the liposomal structure, exposing the entrapped tPA to the fibrin clot. The novel concept of our tPA-loaded ELIP complex is that the delivery agent itself is echogenic, a property that could be harnessed to identify delivery or attachment of the agent to the clot site and temporally direct ultrasound application for tPA release. Conceivably, targeted delivery of the tPA-ELIP to the clot site will render the clot "visible" by diagnostic ultrasound and pinpoint the exact location and timing for therapeutic ultrasound treatment. However, integral to this thrombolytic treatment approach is the specific delivery of the tPA-loaded ELIP to the clot site.

It has been known since the 1970s that plasminogen activators found in certain tissues are strongly bound to fibrin, which logically explains the fibrin specificity of physiologic thrombolysis (Gurewich 2000). Recombinant tPA was engineered to potentiate this fibrin specificity by a positive feedback mechanism whereby binding of the tPA to fibrin results in an increased uncovering of the tPA binding site (the αC domain). Tsurupa and Medved (2001) demonstrated that tPA binds to the fibrinogen αC domains with high affinity, with a Kd value reported as 33±5 nM. Though not to be bound by theory, we currently understand that tPA even when associated with our ELIP will maintain its fibrin binding properties. This will render the tPA-loaded ELIP fibrin-specific providing a self-targeted agent without requirement for further manipulation of the ELIP. This study aimed to investigate the intrinsic fibrin binding properties of our novel EPA-ELIP complex.

Materials and Methods

Liposomal Formulation

ELIP were prepared by the sonication-lyophilization-rehydration method as described previously (Huang et al. 2001). The liposomal composition used was DPPC:DOPC:DPPG:ChoI in a 46:24:24:6 molar ratio (DPPC, dipalmitoyiphosphatidylcholine; DOPC, dioleoylphosphatidylcholine; DPPG, dipalmitoylphosphatidylglycerol; Chol, cholesterol). The component lipids were dissolved in chloroform and the solvent was allowed to evaporate completely. The resulting lipid film was placed under vacuum for full removal of the solvent and then hydrated with distilled, deionized water. This dispersion was sonicated for 5 min to achieve a mean size of 500 nm. 0.2 M D-mannitol was added to the liposome suspension and the sample was frozen at −70° C. The samples were lyophilized for 48 h and resuspended with 0.1 M phosphate-buffered saline (PBS), pH 7.4. The final concentration used for dilution was 10 mg lipid/m] PBS.

Drug Incorporation

Recombinant tPA (Activase®, Genentech Inc., San Francisco, Calif.) was used as the thrombolytic agent. For the drug-loaded ELIP preparation, 1 mg/ml tPA solution was used for the initial rehydration of the lipid film. Entrapped tPA was separated from the free tPA by centrifugation before lyophilization at 16,000 rpm for 10 min at 37° C. (Heeremans et al. 1995). By entrapped tPA, we include both the tPA associated with the lipid bilayer, as well as full encapsulation of the drug within the liposomal aqueous phase (Heeremans et al. 1995). This method resulted in 70% of the tPA being associated with the lipid bilayer, whereas 30% appear to be truly encapsulated within the liposomal core (Tiukinhoy-Laing et al. 2006).

Echogenicity Analysis

The liposomes were imaged with a 20 MHz intravascular ultrasound catheter (SciMed, Inc., Sunnyvale, Calif.) in a glass vial and a 3.5 MHz harmonic transthoracic probe (Acuson, Mountainview, Calif.) in an anechoic imaging well. Relative echogenicity (apparent brightness) of the liposome formulations was objectively assessed using computer-assisted videodensitometry. This process involves image acquisition, pre-processing and gray scale quantification. All image processing and analyses were performed with Image Pro Plus Software (Ver. 1.0, Media Cybernetics, Silver Spring, Md.). Images were digitized to 640×480-pixel spatial resolution (approximately 0.045 mm/pixel) and 8-bit (256 level) amplitude resolution. Data are reported as mean gray scale values.

In-Vitro Clot Formation

Whole porcine blood clots were used to evaluate thrombolysis (Holland et al. 2002). Blood was obtained from non-heparinized Yucatan miniswine. The miniswine were 6-8 weeks old and weighed 28.5±6.5 lbs. Baseline blood analysis data, including complete blood count, prothrombin time, n-dieter and fibrinogen were obtained to ensure normal clotting parameters. Whole blood clots were made by aliqouting 1.5 ml fresh porcine blood into 1.3-cm inner diameter Vacutainer tubes; the tubes were incubated in a 37° C. water bath for 3 h. The clots were then placed in 4° C. until use; this ensured complete clot maturation and retraction. The resulting clots were dark red in color, cylindrical in shape and weighed 0.47±0.11 g. All unused clots were discarded after 2 weeks.

Thrombolysis Studies

Whole porcine blood clots were blotted gently and weighed using an analytical balance. Each clot was placed in an acoustically transparent finger cot from a latex rubber glove containing 10 ml of fresh-frozen porcine plasma (Animal Technologies, Inc., Tyler, Tex.), and placed in a holder within a 37° C. water bath. About 10 units of human plasminogen (EMD Biosciences, Inc., La Jolla, Calif.) were added to each clot holder. Clots were treated with plasma alone (control), free tPA, unconjugated tPA-loaded ELIP, or IgG-conjugated tPA-loaded ELIP. About 1 MHz continuous wave (CW) ultrasound with an intensity of 2 W/cm2 was applied for 2 min (Sonitron 1000; Rich-Mar). The calculated peak negative acoustic pressure output was 0.12 MPa. Ultrasound was delivered in a water bath from a planar, non-focused, 1 MHz transducer (with an aperture of I cm), placed directly next to the finger cot sample holder. After 30 min, clots were taken out of the holder, blotted gently, and re-weighed. Data are reported as percent clot mass loss (defined as the difference between the two clot weights obtained divided by the baseline clot weight).

Assessment of tPA-Fibrin Binding tPA-binding to fibrin was tested using a modification of the solid-phase fibrin-tPA activity assay (SOFIAtPA) developed by Angles-Cano (1986). This method combines a quantitative enzyme-linked immunosorbent assay (ELISA) technique, which enables calculation of ligand binding affinities, with a chromogenic measurement of enzyme specific activity. The latter provides quantitation of tPA bound to fibrin in the microtiter well, which permits the determination of binding affinities and immobilized fibrin concentration by classic Scatchard analysis.

Nunc Maxisorb microtiter plates were coated overnight at 4° C. with human fibrinogen (Calbiochem; 2.5 .tg in 50 p.l 0.05 M sodium bicarbonate, pH 9.6, per well). Background wells were left uncoated. The fibrinogen solution was then aspirated from test wells and all assay wells were blocked with 1% BSA in 0.05 M Tris, pH 8.0 and 0.02% sodium azide, for 1 h at 37° C. Following three washes with PBS-T (0.05% Tween-20 in 0.02M PBS, pH 7.4), adsorbed fibrinogen was converted to fibrin with human thrombin (Sigma-Aldrich; 1 NIH unit+50 MU bovine aprotinin per ml PBS-T) for 20 min at 37° C. The wells were then aspirated and washed as above. Various concentrations of free tPA (1.8-7.4 nM in PBS-T) or tPA-loaded ELIP (4.0-39.7 nM in PBS) were then added to wells for 2 h at 37° C.; all incubation volumes were 50 µl/well. The wells were then similarly aspirated and washed. The last wash before and the first two washes after incubation with tPA-loaded ELIP used PBS instead of PBS-T.

About 200 µl of substrate-zymogen reagent (0.33 µM plasminogen+0.33 mM D-Val-Leu-Lys-p-nitroanilide in 0.02 M PBS, pH 7.3, with 0.1 M sodium chloride) was added to each sample well and to 12 additional wells (standard wells). About 20 µl of tPA diluent (0.1% Triton X-100 in pH 7.3 PBS) was then added to the sample wells while 20 µl of tPA standards (62.5-1000 ng/tnl tPA diluent) were added to the standard wells. The plates were allowed to stand for 10 min at room temperature, after which 2 µl of fibrin monomer solution was added to each well. After an additional 30 min at room temperature, the enzymic reaction was stopped by adding 20 µl of 4 M sodium acetate, pH 3.8, per well. The plates were then read at 405 nm in a Coulter microplate reader. Based on the response of the standards and the net OD of samples corrected for background absorbance in albumin-coated wells, concentrations of bound active tPA were calculated; Scatchard analyses were then performed and binding affinities determined.

Assessment of Highlighting of Clot

Clots were made as described above. Clots were placed in a 24 well plate and treated with buffer, unloaded ELIP or tPA-loaded ELIP for 5 min. After washing twice with PBS, clots were then placed in an anechoic imaging well and imaged using a 3.5 MHz transthoracic probe (Acuson, Mountainview, Calif.). Relative echogenicity (apparent brightness) of the clots were objectively assessed using computer-assisted videodensitometry as described above. Data are reported as mean gray scale values.

Two blinded experienced echocardiographers were also asked to evaluate the clots with regards to brightness in comparison to a control clot image. Brightness was rated on a scale of 1--5, with 1, no difference when compared to the reference control clot; and 5, highly significant highlighting of the clot when compared to the reference control clot.

Statistics

Multiple groups were compared using the analysis of variance (ANOVA) with pairwise multiple comparison performed using the Tukey test. Kruskal-Wallis ANOVA on tanks was used for categorical variables. Spearman rank order correlation coefficient was used to assess variability between the two blinded reviewers with regards to the qualitative assessment of clot highlighting. A p value of <0.05 was considered significant. Analyses were performed using the Sigma Stat software.

Results

The tPA-loaded ELIP are echogenic, with mean gray scale values similar to that of unloaded ELIP (p >0.05). This complex also retained lytic activity as reflected by effective clot lysis similar to that of free tPA (p>0.05 vs. free tPA).

The SOFIA-tPA demonstrated strong fibrin binding of both free tPA and ELIP-associated tPA. Fibrin binding for ELIP-associated tPA appeared to be about twice that for free tPA. Scatchard analysis of the fibrin binding indicated a $K_D$ of 2.61 nM for free tPA and 2.81 nM for tPA-ELIP, which are within the range (1.4±2 nM) reported by Angles-Caro (1986).

This strong fibrin binding by tPA-loaded ELIP was reflected in the clot highlighting experiments performed. Both objective (mean gray scale analysis) and subjective (visual estimation by experienced echocardiographers; Table I) evaluation of the clots showed enhanced highlighting of the clots treated with the tPA-loaded ELIP as compared to the untreated control clot. There was a high correlation for clot echogenicity between the two blinded reviewers with r=0.70 (p<0.05).

Discussion

The efficient and safe delivery of drugs to target sites is the goal of any clinically useful pharmacotherapeutic strategy. This is particularly relevant when dealing with drugs with small therapeutic windows or those with severe or life threatening adverse effects. Systemic delivery of tPA for acute thrombo-occlusive diseases, although life-saving, is limited by the potential for significant bleeding. There is also concern of effective concentrations reaching the desired site for plasminogen activation. Hence, development of second and third generation thrombolytic agents with increased fibrin specificity, resistance to plasminogen-activator inhibition, or plasma half-lives are actively being investigated (Van de Werf 1999; North and Bode 2003).

Another area of active investigation involves application of ultrasound to mediate enhanced thrombolysis. Recent clinical studies have demonstrated improved thrombolysis with the concomitant use of focused ultrasound and a thrombolytic agent for stroke and acute myocardial infarction (Cohen et al. 2003; Alexandrov et al. 2004). Suggested mechanisms include rectified diffusion which promotes transport of drugs into the thrombus, reformation and opening of the fibrin matrix which enhances drug diffusion, cleaving of fibrin polymers to extend the surface for drug interaction, and direct effects on binding of the agent to fibrin (Eccleston et al. 1996). For the clinical application of noninvasive ultrasound therapy, however, it may be advantageous to visualize the clot in order to selectively insonify the area of interest, thus limiting potential harmful bioeffects to surrounding tissues.

We have reported a novel technique to generate echogenic liposomes, which can be targeted to specific atheroma components (Demos et al. 1999; Huang et al. 2001). We have demonstrated effective targeting of ELIP conjugated to polyclonal and monoclonal antibodies to fibrin and ICAM-1 in vitro (Demos et al. 1997, 1998) and in vivo (Demos et al. 1999; Hamilton et al. 2002). More recently, we reported entrapment of tPA into ELIP with demonstration of effective thrombolysis in vitro (Tiukinhoy-Laing et al. 2006). As the tPA-loaded ELIP are echogenic, local drug delivery can potentially be achieved by using directed ultrasound (at diagnostic ultrasound frequencies) to facilitate drug release (at therapeutic ultrasound frequencies) from the ELIP. However, integral to this thrombolytic approach is the specific delivery of the tPA-loaded ELIP to the clot site.

Of the total tPA entrapped in our novel tPA-loaded ELIP, 30% are fully encapsulated within the ELIP, whereas 70% are associated with the lipid bilayer (Tiukinhoy-Laing et al. 2006). tPA itself contains fibrin-binding domains (Nesheim et al. 1990; Tsurupa and Medved 2001), which logically explains the fibrin specificity of the enzyme in physiologic thrombolysis. In this study, we confirmed the previously reported high-affinity association of tPA with fibrin (Angles-Cano 1986) and demonstrated that this binding affinity was fully retained by the tPA-loaded ELIP. In fact, the specific activity of tPA-ELIP in the SOFIA-tPA was about twice that observed for tPA alone. Affinities of ~$5 \times 10^8$ $M^{-1}$ (2 nM) for this interaction are in the range of the highest values previously observed for ELIP targeted using polyclonal anti-fibrin antibodies (Klegerman et al. 2002b).

This ability of the tPA-loaded ELIP to bind to fibrin was also confirmed in an in-vitro clot model. Clots were highlighted verifying attachment of the contrast agent to the clot; this enhanced echogenicity can be visually appreciated with good interobserver agreement between two blinded experienced echocardiographers. Hence, tPA-loaded ELIP delivery to the thrombus site can potentially be verified in real time in vivo using ultrasound imaging. Visualization of the highlighted clot may then allow for directed drug release and focused therapeutic ultrasound therapy.

In summary, this study demonstrates specific fibrin binding of tPA-loaded ELIP. The unique characteristics of tPA as a drug for specific targeting seems to render further manipulation of the tPA-loaded ELIP agent (such as ligand conjugation to the lipid surface) unnecessary. The targeted delivery of a thrombolytic agent to the site of occlusion with decreased systemic plasminogen activation is a desirable clinical strategy and has implications for the treatment of many thrombo-occlusive diseases. tPA itself has been shown to have specific binding to fibrin, and its association with ELIP allows retention of and even seems to improve upon, this fibrin-binding property. We were further able to demonstrate confirmation of binding of tPA-loaded ELIP to fibrin using an in vitro clot model.

TABLE I

Qualitative echogenicity assessment using rank scale (1, no difference when compared to reference control clot; 5, highly significant highlighting of the clot when compared to reference control clot).

| N = 3 | Control clot | Clot treated with unloaded ELIP | Clot treated with tPA | P value |
|---|---|---|---|---|
| Echogenicity rank | 1.8 ± 0.8 | 2.5 ± 1.2 | 4.2 ± 0.8 | 0.003 |

*p = 0.025 vs. clot treated with unloaded ELIP.

Acknowledgements

This study is supported in part by the National Institutes of Health R01 EL-74002, and the Feinberg Cardiovascular Research Institute, Chicago, Ill.

REFERENCES

Aiexandrov A V, Molina C A, Grotto J C, Garami Z, Ford S R, Alvarez-Sabin J, Montaner J, Saqqur M, Demchuk A M, Moye L A, Hill M D, Wojner A W CLOTBUST Investigators. 2004, Ultrasound-enhanced systemic thrombolysis for acute ischemie stroke. N Engl J Med 351(21); 2170-2178.

Angles-Caro E, 1986. A apectrophotometric solid-phase Maintissue plasminogen activator activity assay (SOFIA-tPA) for high-fibrin-affinity tissue plasminogen activators. Anal Bloch=153:201-210.

Bangham A D, Standish M M, Watkins J C. 1965. Diffusion of univalent ions across the lamellae of swollen phospholipids. j Mol Biol 13:238-252.

Cohen M G, Tuero E, Bluguermann J, Kevorldan R, Berrocal D1-I, Carlevaro 0, Picabea E, Hudson M P, Siegel 1, Douthat L, Greenbaum A B, Bcht D, Weaver W D, Grinfeld L R. 2003. Transcuteneous ultrasound facilitated coronary dram bulysis during acute myocardial infarction. Am J Cordial 92:454-457.

Demos S M, Onyuksel H, Gilbert J, Roth S I, Kane B, Jungblut P, Pinto J V, McPherson D D, Klegerman M E. 1997. In vim, targeting of antibody-conjugated echogenic liposomes for sitespecific ultrasonic image enhancement. j Pharm Sci 86: 167-171.

Demos S M, Dagar S, Klegerman M, Nagarai A, McPherson D D, Onyuksel H. 1998. In vitro targeting of acoustically reflective immunoliposames to fibrin under various flow conditions. J Drug Target 5:507-518.

Demos S M, Mian-Onyuksel H, Kane B J, Raman' K, Naganii A, Greene R Klegerman M, McPherson D D. 1999, In-vivo targeting of acoustically reflective liposomes for intravascular ultrasonic enhancement. J Am Coll Cardiol 33(3); 867-875.

Eccleston D S, Horrigan M C, Ellis S G. 1996, Rationale for local drug delivery. Semin Intern Card 1(1):8-16.

Gurewich V 2000, Thrombolysis: An unfinished agenda. Blood Coagul Thrombolysis 11:401-408.

Hamilton A, Huang S L, Warnick D, Stein A, Rabbat M, Madhav T, Kane B, Nagaraj A, Klegerman M, MacDonald R, McPherson D. 2002. Left ventricular thrombus enhancement following intravenous injection of echogenic immunoliposomes: Studies in a new experimental model. Circulation 105(23):2772-2778.

HeeremansGerritsen H R, Meusen S P, Mijnheer F W, Gangaram Panday R S, Prevost R, Kiuft C, Crommelin D J. 1995. The preparation of tissue-type plasminogen activator (tPA) containing liposornes: Entrapment efficiency and ultracentrifugation damage. j Drug Target 3:301-310.

Holland C K, Vaidya S S, Coussios C C, Shaw G J. 2002. Thrombolytic effects of 120 kHz and 1 MHz ultrasound and tissue plasminogen activator on porcine whole blood clots. J Acou®t Soc Am 112:2370.

Huang S L, Hamilton A J, Nageraj A, Tiukinhoy S D, Klegerman M E, McPherson D D, Macdonald R C. 2001. Improving ultrasound reflectivity and stability of echogenic liposomal dispersions for use as targeted ultrasound contrast agents. J Pharm Sri 90(12):1917-1926.

Klegerman M E, Hamilton A J, Huang S L, Tiukinhoy S D, Khan A A, MacDonald R C, McPherson D D. 2002a. Quantitative immunoblat assay for assessment of liposomal antibody conjugation 02 efficiency, Anal Biochem 300:46-52.

Klegerman M E, Hamilton A J, Tiukinhoy S D, Khan A A, Huang S L, MacDonald R C, McPherson D D. 2002b. Fibrin association characteristics of atheroma-targeted echogenic intmunolipasomea. Thromb Vasc Bin] 22(5): 214, Nesheim M, Fredenburgh J C, Larsen G R. 1990. The dissociation constants and stoichiometriea of the interactions of lysplasminogen and chloromethyl ketone derivatives of tissue plasminogen activator and the variant (FEIX with intact fibrin, J Biol Chem 265; 21541-21548.

Nordt T K, Bode C. 2003. Thromholysis: Newer thrombolytir agents and their role in clinical medicine. Heart 89:1358-1362. Ranby M, Wallen P. 1981. A sensitive parabolic rate assay for the issue plasminogen activator. Prog Fibrinol 5:233-235.

Scopes R K. 1982. Protein purification: Principles and practice. New York: Springer. p 265-266.

Tiukinhoy-Laing S D, Huang S, Klegerman M, Holland C, MacDonald R C, McPherson D D. 2006. Ultrasound-facilitated thrombolysis using tissue-plasminogen activator-loaded echogenic tiposnmes. Thromb Res, In Press.

Tiukinhoy 5, Mahowald M, Shively V, Nagarai A, Kane B, Klegerman M, MacDonald R, McPherson D, Matsumura J2000, Development of echogenic, plasmid-incorporated, tissue-targeted cationic liposomes that can be used for directed gene delivery. Investig Radio] 12:732-738.

Tiukinhoy S, Khan A, Huang S, Kiegerman M, MacDonald R, McPherson D. 2004. Now] echogenic drug-immunoliposomes for drug delivery, lnvestig Radio! 39:104-110.

Tsurupa G, Medved L. 2001. Fibrinogen (C domains contain cryptic plasminogen and tPA binding sites. Ann NY Aced Sci 936:328-330.

Van de Weef F J. 1999. The ideal fibrinolytic: Can drug design improve clinical results? Eur Heart J 20:1452-1458.

Example 6

Targeting of Tissue Plasminogen Activator-Loaded Echogenic Liposomes for Site-Specific Thrombolysis Background:

We have previously reported development of tissue plasminogen activator-loaded echogenic liposomes (tPA-ELIP). The purpose of this study was to determine the feasibility of antibody conjugation to this novel formulation, while assessing retention of echogenicity and tPA activity.

Methods:

ELIP were prepared by dehydration-rehydration-lyophilization; tPA was added prior to lyophilization. Rabbit IgG was conjugated to tPA-ELIP (325±58 µg tPA/15 mg lipid) via a thioether linkage. Echogenicity was assessed with a 20 MHz intravascular ultrasound catheter and reported as mean gray scale values. IgG conjugation efficiency (CE) was determined with a quantitative immunoblot assay and total ELIP-associated protein by Lowry assay. Whole blood porcine clots were treated with plasma only (control), liposomes only, free IPA, unconjugated WA-ELIP, and IgG-conjugated tPA-ELIP. Ultrasound was applied at 2 W/sq cm for 2 min. to effect drug release. tPA activity was determined using clot mass loss after a 30 min. treatment.

Results:

IgG conjugation to tPA-ELIP was feasible with a CE of 14.4±4.9 µg IgG/mg lipid. Echogenicity of IgG-conjugated-IPA-ELIP was similar to unconjugated tPA-ELIP (p=0.975). Throughout the conjugation process, more than 70% of the IPA protein remained associated with the ELIP, but tPA activity decreased. However, % clot mass loss remained significantly higher than control or unloaded ELIP (p<0.05), with retention of at least 46% lytic activity.

Conclusion:

Antibody conjugation to tPA-ELIP for controlled, directed delivery of tPA to the thrombus site is feasible. This methodology results in retention tPA-ELIP echocenicity and of substantial lytic effect. In vivo targeting of the drug-liposomal agent may more than offset any IPA activity loss compared to systemic tPA administration, while also providing safer and more specific drug delivery.

Example 7

Background

We have previously reported development of echogenic liposomes (ELIP) for the targeted highlighting of structures with potential for drug and gene delivery.

Targeting of these agents was achieved through direct conjugation of the ELIP with an antibody using a thioether linkage.

Recently, we studied the potential of ELIP as an agent for ultrasound-releasable directed thrombolytic therapy and demonstrated effective thrombolysis using tissue plasminogen activator (tPA)-loaded ELIP in an in vitro clot model.

Development of a fibrin-targeted, ultrasound-releasable lytic complex represents a novel therapeutic strategy for the local delivery of a thrombolytic agent.

Methods

Liposomal Formulation

ELIP were prepared by the sonication-lyophilization-rehydration method (Huang et al. J. Pharm Sci 90:1917, 2001) in a 46:24:24:6 molar ratio of DPPC:DOPC:DPPG:Chol (DPPC=dipalmitoylphosphatidylcholine: DOPC=dioleoylphosphatidylcholine: DPPG=dipalmitoylphosphatidylglycerol: Chol=Cholesterol). For antibody conjugation, 8 mole % of 1,2-dipalmitoyl-en-glycero-3-phosphoethanol-amine-N-[-4-p-maleimidophenyl)butyrate] (MPB-PE) was added, with concomitant decrease in DPPC:DPPG:Chol proportions.

Drug Incorporation

Recombinant tPA (Activase®, Genentech Inc., San Francisco, Calif.; 1 mg/ml) was used for the initial rehydration of the lipid film instead of water. Entrapped tPA was separated from the free tPA by centrifugation at 16,000 rpm for 10 minutes at 37° C.

Liposome Conjugation

Rabbit IgG was conjugated to tPA-ELIP via a thioether linkage as previously described for ELIP (Klegerman et al., Anal Biochem 300:46, 2002). Protein recoveries in the concentrated SPDP-IgG and thiolated IgG fractions were measured with the Lowry assay, while thiolation efficiency of the IgG was assessed from the $A_{345}$ of thiopyridone released during reduction. Conjugation efficiency of IgG-conjugated tPA-loaded ELIP was determined by a quantitative immunoblot assay for liposomal rabbit IgG. The tPA content of tPA-loaded ELIP was measured by Lowry assay relative to tPA standards containing 50 µg ELIP lipid per µg tPA. The relative contribution of IgG to the assay was assessed from the tPA-loaded ELIP/thiolated IgG reaction mixture, containing a known amount of IgG.

The IgG contribution (determined by immunoblot assay) to the dialyzed IgG-conjugated tPA-loaded ELIP product was then subtracted from the Lowry assay response, yielding the tPA content of the product. The enzymatic activity of tPA was measured by a colorimetric paranitroanilide-substrate method (Ranby and Wallen, Prog Fibrol 8:233, 1961).

Thrombolysis Studies

Whole porcine blood clots were blotted gently and weighed using an analytical balance. Each clot was placed in an accoustically transparent finger cot from a latex rubber glove containing 10 mil of fresh-frozen porcine plasma and placed in a holder with a 37° C. water bath. 10 unites of human plasminogen wee added to each clot holder. Clots were treated with plasma alone (control), free tPA unconjugated tPA-loaded ELIP, or 1 gG-conjugated tPA-loaded ELIP. 1 MHz continuous wave (CW) ultrasound with an intensity of 2 Watts/cm2 was applied for 2 minutes (Sonitron 1000; Rich-Mar). The calculated peak negative acoustic pressure output was 0.12 PPz. Ultrasound was delivered in a water bath from a planar, non-fOcused, 1 MHz transducer (with an aperture of 1 cm), placed directly next to the finger cot sample holder. After 30 minutes, clots were taken out of the holder, blotted gently, and re-weighed.

Results

Recoveries of SPDP-IgG and thiolated IgG (68±35% and 41±22%, respectively), as well as the thiolation efficiency (4.7 thiols/molecule) were within the range of values usually obtained during IgG-ELIP conjugation procedures in our laboratory.

The IgG conjugation efficiency (14.4±4.9 µg/mg lipid) also compared favorably with previous conjugated ELIP preparations.

The IgG-conjugated tPA-loaded ELIP were echogenic, with mean gray scale values similar to that of unconjugated tPA-loaded ELIP (p=0.734).

Although >70% of the tPA protein remained associated with the ELIP throughout the conjugation process, there were large decreases in tPA activity at every stage of the conjugation procedure, resulting in a net activity recovery of only 11.3±1.5% in the reconstituted product.

The decreased tPA activity is reflected in a decrease in clot lysis effect (p<0.001 vs. unconjugated tPA-loaded ELIP.

The loss in enzyme activity was not improved when we attempted to protect the enzyme active site by performing a sham conjugation procedure in the presence of 0.1 M L-arginine.

The unconjugated tPA-loaded ELIP showed as good if not slightly greater clot lysis effect as free tPA (p>0.05).

Conclusions

Antibody conjugation of tPA-ELIP is feasible. Major parameters (conjugation efficiency, echogenecity and tPA protein retention) are presented. tPA activity loss may be compensated by targeting, may be decreased by gel filtration purification of conjugated tPA-ELIP, may be avoided by intrinsic tPA-ELIP targeting (based on tPA affinity for fibrin).

Example 8

To determine proportions of human recombinant tissue plasminogen activator (tPA; Activase®) adsorbed to the surface of echogenic liposomes (ELIP), integrally incorporated into the ELIP bilayer and encapsulated within the vesicles. ELIP were prepared by dehydration-rehydration-lyophilization; tPA was added to the dried lipid film prior to lyophlization. To determine free and total ELIP-associated tPA, including loosely adsorbed tPA, tPA-ELIP samples were dialyzed to equilibrium in cellulose ester dialysis units (300 kDa MWCO) vs. 50 volumes of phosphate-buffered saline (PBS) for 4 hours at 4° C. Protein in the tPA-ELIP samples and the dialysis retentates were assessed by Lowry assay. Enzyme activity in tPA-ELIP, retentates and dialyzates was measured with a colorimetric paranitroanilide-substrate method (Ranby and Wallen: Prog Fibrinol 5:233, 1981). The tPA immunoreactivity of these fractions was quantitated with a sandwich ELISA utilizing a monoclonal capture antibody (Ab) and a polyclonal detection Ab. To assess tightly associated tPA under sink conditions, including encapsulated protein, complete dialysis was carried out for at least 24 hours with two buffer changes. Exposed immonoreactive tPA was determined by ELISA of the retentate in PBS not containing Tween 20 relative to tPA standards in PBS. The entire procedure was repeated twice (n=3). 21.0±7.5% tPA protein was not retained during equilibrium dialysis, while 33.4±4,6% was determined to be loosely associated with ELIP, calculated as the difference between retained protein in equilibrium and complete dialyses. One-third (34.3±1.1%) tPA (Ab-binding epitopes exposed) was tightly associated with ELIP (corrected for a 35% loss of immunoreactivity during dialysis). The remaining 12.4±1.1% was inaccessible and presumed to be encapsulated. Free tPA (3.3±0.9% total enzyme activity) exhibited an appreciably lower specific activity than ELIP-associated tPA. 73% of tPA expected to remain associated with tPA-ELIP after clinical administration would be exposed to the environment. These and previous data indicate that tPA catalytic and fibrin-binding sites are similarly exposed. The appreciable hydrophobic character of tPA suggests that the tightly associated, exposed protein may be integrally incorporated across the lipid bilayer of ELIP, allowing both targeting and therapeutic properties.

Example 9

Abstract

Purpose:

To determine proportions of human recombinant tissue plasminogen activator tPa adsorbed to the surface of echogenic liposomes (ELIP), integrally incorporated into the ELIP bilayer and encapsulated within the vesicles.

Methods:

ELIP were prepared by dehydration-rehydration-lyophilization. tPA was added to the dried lipid film prior to lyophilization. To determine free and total ELIP-asociated tPA, including loosely adosorbed tPA, tPA-ELIP samples were dialyzed to equilibrium in cellulose under dialysis units (3000 Da MWCO) vs. 50 volumes of phosphate-buffered saline (PBS) for 4 hours at 4° C. Protein in the tPA-ELIP samples and the dialysis retentates were assessed by Lowry assay. Enzyme activity in tPA-ELIP, retentates and dialyzates were measured with a colorimetric paranitroanilide-substrate method (Ranby and Wallen: Prog Fibrinol 5:233, 1981). The tPA immunoreactivity of these fractions was quantitated with a sandwich ELISA utilizing a monoclonal capture antibody (Ab) and a polyclonal detection Ab. To assess associated tPA under sink conditions, including encapsulated protein, complete dialysis was carried out for at least 24 hours with two buffer changes. Exposed immunoreactive tPA was determined by ELISA of the retentate in PBS and containing Tween 20 relative to tPA standards in PBS. The entire procedure was repeated twice (n=3).

Background

We have previously demonstrated that tPA-loaded echogenic liposomes (tPA-ELIP) retain full echogenicity and thrombolytic activity. We have confirmed a clinically relevant tPA fibrin-binding capacity and have shown that tPA-ELIP targets fibrin with an affinity comparable to free tPA. We have demonstrated a practical clot-targeting capability for tPA-ELIP in vitro. In vivo studies are in progress.

Methods

Liposomal Formulation

ELIP were prepared by the sonication-lyophilization-rehydration method (Huang et al. J. Pharm Sci 90:1917, 2001) in a 46:24:24:6 molar ratio of DPPC:DOPC:DPPG:Chol (DPPC=dipalmitoylphosphatidylcholine:DOPC=dioleoylphosphatidylcholine:DPPG=dipalmitoylphosphatidylglycerol:Chol=Cholesterol). For antibody conjugation, 8 mole % of 1,2-dipalmitoyl-en-glycero-3-phosphoethanol-amine-N-[-4-p-maleimidophenyl)butyrate] (MPB-PE) was added, with concomitant decrease in DPPC:DPPG:Chol proportions.

Drug Incorporation

Recombinant tPA (Activase®, Genentech Inc., San Francisco, Calif.; 1 mg/ml) was used for the initial rehydration of the lipid film instead of water. Entrapped tPA was separated from the free tPA by centrifugation at 16,000 rpm for 10 minutes at 4° C.

Dialysis and Analyses

To determine free and total ELIP-associated tPA, including loosely adsorbed tPA, tPA-ELIP samples were dialyzed to equilibruim in cellulose ester dialysis units (3000 kDA MWCO) vs. 50 volumes of phosphate-buffered saline (PBS) for 4 hours at 4° C. To assess tightly associated tPA under sink conditions, including encapsulated protein, complete dialysis was carried out for at least 24 hours with two buffer charges. Protein in the tPA-ELIP samples and the dialysis retentates were assessed by Lowry assay. Enzyme activity in tPA-ELIP, retentates and dialyzates was measured with a colorimetric paranitroanilide-substrate method (Ranby and Wallen: Prog Fibrinol 8:233, 1981).

ELISA

Nunc MaxiSorp microtiter plates were coated with 5 µg/ml of a monoclonal anti-tPA capture Ab (Abcam, Inc., Cambridge, Mass.) in 0.05M sodium bicarbonate, pH 9.5, overnight at 4° C. All incubation volumes were 50 µl/well. One-half of wells were left uncoated for determination of nonspecific binding. After aspirating well contents, all wells were blocked with conjugate buffer (1% bovine serum albumin in 0.05M Tris buffer, pH 8.0, with 0.02% sodium azide) for 1 hour. From this point, all incubations were at 37° C. Each incubation was followed by aspiration of well contents and washes (3×) with PBS-T (0.02M phosphate buffered saline, pH 7.4, with 0.05% Tween 20). For assay of intact tPA-ELIP, wells were washed with PBS after blocking and the first wash after the ELIP incubation was also with PBS.

Various dilutions of tPA or tPA-ELIP were incubated for 2 hours. All wells were then incubated with 10 µg/ml of a secondary polyclonal sheep anti tPA detection Ab in 0.1% BSA/PBS-T diluent for 1 hour, followed by a 1-hour incubation with 1:3.000 donkey anti-sheep IgG-alkaline phosphatase in conjugate buffer. The substrate incubation consisted of 50 µl of substrate buffer (0.05M glycine buffer, pH 10.5 with 1.5 mM magnesium chloride)+50 µl nitrophenyl phosphate in substrate buffer per well for 15 minutes. The reaction was stopped with 50 µl 1M sodium hydroxide per well. The optical absorbance of each well at 405 nm ($A_{405}$) was measured with a SpectraMax M5 microplate reader. Net $A_{405}$ was determined by subtracting the absorbance of background wells from that of capture Ab-coated wells. tPA concentrations of samples were calculated relative to tPA standards in the corresponding diluent.

Results

79% of IPA protein remained associated with ELIP during equilibrium dialysis. A significantly higher proportion of tPA activity was found in the retentate, mainly due to the lower specific activity of free tPA.

Total tPA-ELIP (PBS-T) ELISA values show good correspondence with tPA protein (100.2±23.5% immunoreactivity), but lose about one-third immunoreactivity during complete dialysis.

About one-third of tPA was calculated to be loosely associated with tPA-ELIP, while another third was tightly associated and exposed; a remaining one-eighth was not exposed and presumed to be encapsulated.

Example 10

Introduction

The efficient and safe delivery of drugs to target sites is the goal of any clinically useful pharmacotherapeutic strategy. This is particularly relevant when dealing with drugs with small therapeutic windows or those with severe or life threatening adverse effects. Systemic delivery of tPA for acute thrombo-occlusive diseases, although life-saving, is limited by the potential for significant bleeding. There is also concern of effective concentrations reaching the desired site for plasminogen activation. Hence, development of second and third generation fibrinolytic agents with increased fibrin specificity, resistance to plasminogen-activator inhibition, or plasma half-lives are actively being investigated (Van de Werf 1999; Nordt and Bode 2003).

Another area of active investigation involves application of ultrasound to mediate enhanced thrombolysis. Recent clinical studies have demonstrated improved thrombolysis with the concomitant use of focused ultrasound and a thrombolytic agent for stroke and acute myocardial infarction (Cohen et al. 2003; Alexandrov et al. 2004). Suggested mechanisms include rectified diffusion which promotes transport of drugs into the thrombus, reformation and opening of the fibrin matrix which enhances drug diffusion, cleaving of fibrin polymers to extend the surface for drug interaction, and direct effects on binding of the agent to fibrin (Eccleston et al. 1996). For the clinical application of noninvasive ultrasound therapy, however, it may be advantageous to visualize the clot in order to selectively insonify the area of interest, thus limiting potential harmful bioeffects to surrounding tissues.

We have reported a novel technique to generate echogenic liposomes, which can be targeted to specific atheroma components (Demos et al. 1999; Huang et al. 2001). We have demonstrated effective targeting of ELIP conjugated to polyclonal and monoclonal antibodies to fibrin and ICAM-1 in vitro (Demos et al. 1997, 1998) and in vivo (Demos et al. 1999; Hamilton et al. 2002). More recently, we reported entrapment of tPA into ELIP with demonstration of effective thrombolysis in vitro (Tiukinhoy-Laing et al. 2006). As the tPA-loaded ELIP are echogenic, local drug delivery can potentially be achieved by using directed ultrasound (at diagnostic ultrasound frequencies) to facilitate drug release (at therapeutic ultrasound frequencies) from the ELIP. However, integral to this thrombolytic approach is the specific delivery of the tPA-loaded ELIP to the clot site.

Background:

We have developed echogenic immunoliposomes (ELIP) that can incorporate drugs for targeted delivery. We have recently reported encapsulation of tissue plasminogen activator (tPA) into ELIP. tPA has been shown to bind to the fibrinogen aC domain with high affinity. The aim of this study was to evaluate the specific highlighting of blood clots and to show efficient drug localization using tPA-encapsulated ELIP.

Methods:

tPA was incorporated into the ELIP during development. Whole porcine blood clots were incubated with PBS (control), 5 mg of ELIP, or 5 mg of tPA-ELIP in a 24-well plate for 5 mins. Clots were then washed and imaged using a 3.5 MHz transvascular ultrasound probe. Echogenicity was quantified using computer-assisted videodensitometry. Data are reported as mean gray scale values (MGS). Two blinded echocardiographers also ranked the differences in brightness (scale of 1-5) of the treated clots as compared to control.

Results:

tPA-encapsulated ELIP effectively highlighted clots (Picture). The MGS of the control, the ELIP, and the tPA-ELIP were $14.2\pm0.7$, $21\pm9.0$, and $32.3\pm2.4$, respectively (n=3, $p<0.05$). Visualization of the thrombus was also improved qualitatively, as the mean echogenicity rank of tPA-ELIP was $4.2\pm0.8$, compared to ELIP rank of $2.5\pm1.2$, and a control rank of $1.8\pm0.8$ (n=3).

Conclusion:

We have demonstrated highlighting of whole blood clots using tPA-encapsulated ELIP. This agent has potential for site-specific drug delivery with highlighting of the target site.

Example 11

Targeted delivery of a thrombolytic agent is an attractive concept, with implications for the treatment of many thrombo-occlusive diseases. Recent clinical studies have demonstrated improved thrombolysis with the concomitant use of focused ultrasound and a thrombolytic agent for stroke and acute myocardial infarction. Real-time visualization of the thrombus during therapy can assist with the temporal and spatial delivery of therapeutic ultrasound to assist with clot lysis.

We have previously demonstrated entrapment of tissue plasminogen activator (tPA) into echogenic liposomes (ELIP) with effective clot lysis and drug release using ultrasound in vitro. We have also demonstrated retention of the intrinsic strong fibrin binding of tPA when associated with ELIP with significant clot highlighting in vitro. This study aimed to evaluate whether tPA-ELIP can enhance the ultrasonographic visualization of a left ventricular thrombus in an animal model.

Methods:

Liposome Formulation

ELIP were prepared by the dehydration-lyophilization-rehydration method as described previously (20). Liposomal composition used was DPPC:DPPE:DPPG:Chol in a 42:24:24:10 molar ratio (DPPC=dipalmitoylphosphatidylcholine; DOPC=dioleoylphosphatidylcholine; DPPG=dipalmitoylphosphatidylglycerol; Choi=Cholesterol). The component lipids were dissolved in chloroform and the solvent was allowed to completely evaporate. The resulting lipid film was placed under vacuum for full drying and then rehydrated with distilled, deionized water. This dispersion was sonicated until a desired mean size (500 nm) was obtained. 0.2 M D-Mannitol was added to the liposome suspension and the sample was frozen at $-70°$ C. The samples were lyophilized for 48 hours and resuspended with 0.1 M phosphate-buffered saline (PBS). The final concentration used for dilution was 10 mg lipid/ml buffer.

Drug Incorporation

Recombinant tissue-plasminogen activator (tPA) (Activase®, Genentech Inc., San Francisco, Calif.) was used as the thrombolytic agent. For the drug-liposome preparation, 1 mg/ml tPA solution was used for the initial rehydration of the lipid film. Free tPA was separated from the entrapped ELIP by centrifugation at 15,777 g for 10 minutes at $37°$ C. As described previously, a maximum of 400 gg of tPA could be loaded per 10 mg of liposomal lipid. Entrapment efficiency was 50%.

Thrombus Formation

Coronary arteries supplying the left ventricular apex in Mongrel dogs (n=2) were ligated. Two mL Hemaseal (Tisseal) was injected (intracardiac) to stimulate thrombus formation.

Thrombus Highlighting tPA-ELIP (200 ug tPA/5 mg lipid) were prepared and injected into the left atrial appendage. Epicardial echocardiography was performed at baseline, after thrombus formation, and at different time points after tPA-ELIP injection.

Acoustic Analysis

The left ventricular thrombus was imaged using a 3.5 MHz transvascular probe (Acuson, Mountainview, Calif.) placed epicardially. Relative echogenicity (apparent brightness) of the thrombus was objectively assessed using computer-assisted videodensitometry. This process involves image acquisition, pre-processing, and gray scale quantification. All image processing and analyses are performed with Image Pro Plus Software (Ver. 1.0, Media Cybernetics, Silver Spring, Md.) running on a dedicated computer (486 CPU, 66 MHz). Images were digitized to 640×480-pixel spatial resolution (approximately 0.175 mm/pixel) and 8-bit (256 level) amplitude resolution. Data are reported as mean gray scale values (MGSV).

Two blinded experienced echocardiographers also reviewed randomized images of the clots and ranked clot echogenicity compared to a reference control clot (Rank scale 1-5; 1=similar to reference clot, 5=very high echogenicity compared to reference clot).

Thrombolysis Analysis

The left ventricular thrombus was similarly imaged using a 3.5 MHz transvascular probe (Acuson, Mountainview, Calif.) placed epicardially. Images were similarly digitized and analyzed off-line. Left ventricular thrombus was manually outlined using a distinct boundary of contrast (thrombus to blood) with respect to background. The thrombus volume (per mm depth) was measured at 15 minute intervals for the entire course of the experiment following initial left atrial administration of tPA-ELIP.

Figure 2:
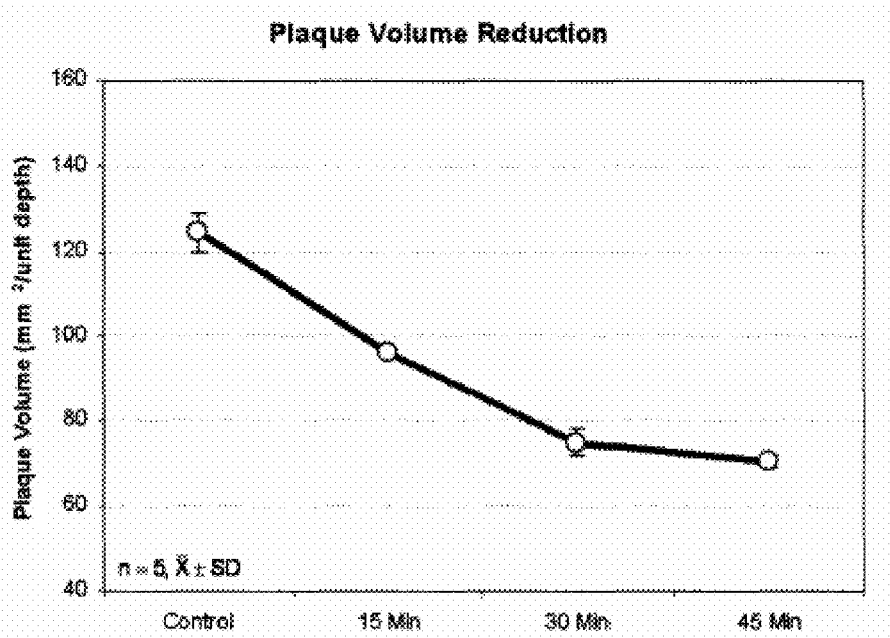
FIG. 2 shows a result from Example 11, the baseline therapeutic efficacy of thrombolysis

Results:

tPA-ELIP effectively highlighted the left ventricular apical thrombus, with a MGSV that is different from control ($p<0.001$). Clot highlighting by tPA-ELIP was stable for at least 15 minutes in vivo (FIG. 1). The second experiment confirmed the targeting efficiency demonstrated by the first experiment and established baseline therapeutic efficacy of thrombolysis (FIG. 2). There was a significant difference in the subjective echogenicity ranking of tPA-ELIP treated clots compared to controls ($p<0.001$), with a high correlation between the two blinded reviewers ($r=0.54$; $p<0.001$).

Conclusions:

Our novel tPA-ELIP can enhance left ventricular thrombus in vivo. Both quantitative and qualitative evaluation of clot echogenicity showed enhanced highlighting of clots treated with tPA-ELIP. tPA-ELIP has the potential to deliver a thrombolytic agent with real time clot imaging during therapy. The thrombolytic efficacy observed, in which the clot volume decreased by nearly half in 45 minutes, appears to be analogous to a previously demonstrated in vitro thrombolytic capacity of tPA-ELIP that was nearly equal to free tPA. It is expected, therefore, that administration of therapeutic ultrasound will significantly enhance tPA-ELIP thrombolytic efficacy in vivo, as it did in vitro. This is an exciting approach to thrombolysis with specific clot highlighting for the temporal and spatial guidance of ultrasound therapy for targeted drug release from the tPA-ELIP complex.

Example 12

Added 100 µl 0.2% BSA/PBS to each well and incubated at 37° C. for 1 hour. All subsequent incubations were also at 37° C. Aspirated the wells and washed the plate 3× with PBS-T. Added Activase dilutions (10, 5, 2.5, 1.25, and 0.625 µg/ml PBS-T) to replicate wells (1000/well). Incubated for 2 hours. Removed the contents of each well and pooled all samples within each dilution. Stored pooled samples at 4° C. For tPA-ELIP dilutions (in PBS), the third wash before adding the samples was with PBS. Stored the pooled tPA-ELIP samples in polypropylene tubes.

Added monoclonal anti-tPA capture antibody (Ab) (5 µg/ml coating buffer; 50 Owen) to rows B, C, E and G of a fresh microplate. Incubated in a humidified chamber at 4° C. overnight. All subsequent incubations were in humidified chambers at 37° C. at volumes of 50 µl/well, followed by aspiration of wells and 3× washes with PBS-T. Blocked all rows with conjugate buffer for 1 hour. Added tPA standards (50, 25, 12.5, 6.25 and 3.13 ng/ml) and pooled sample dilutions (in PBS-T) in duplicate to sample (B, C, E, G) and background (A, D, F, H) wells. Incubated for 2 hours. Added secondary detection Ab (10 µg sheep anti-tPA/m10.1% BSA in PBS-T) to all wells and incubated 1 hour, followed by a conjugate incubation (3,000× diluted with conjugate buffer; 1 hour). Added 50 µl of substrate buffer+500 of substrate (1 tablet/5 ml substrate buffer) to each well. Incubated at 37° for 15 minutes. Immediately quenched with 5 µl of 1M sodium hydroxide/well. Read the plate at 405 nm. Determined net absorbance ($A_{405}$) by subtracting background OD from sample OD (e.g., B4-A4 or E7-F7).

Calculated the undiluted tPA concentrations of each pooled sample from the standard curve. These represented the free fractions ([F]) of the sample dilutions after equilibrium incubation with fibrin. Obtained the bound concentrations ([B]) by subtracting the free values from the total tPA concentration of the starting dilutions. Prepared Scatchard plots by plotting [B] (x-axis) vs. B/F (y-axis). The slope=$-K_{assoc}$ and the y-intercept=$K_{assoc}[n]$, where [n] was the concentration of exposed tPA binding sites on the fibrin pads.

Results

Figure 3:
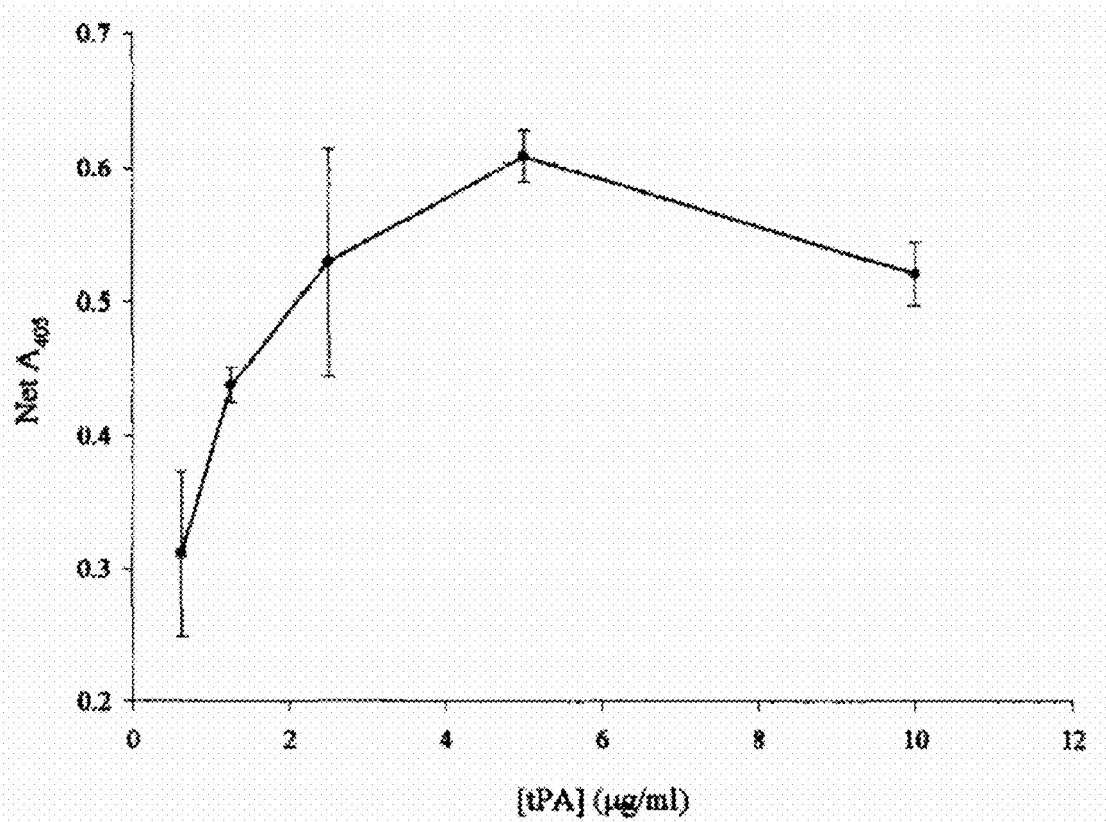
FIG. 3 shows an ELISA plot, exhibiting saturation binding behavior for free tPA, from a fibrin pad assay of 4 replicate samples per tPA concentration as described in Example 12.
Figure 4:
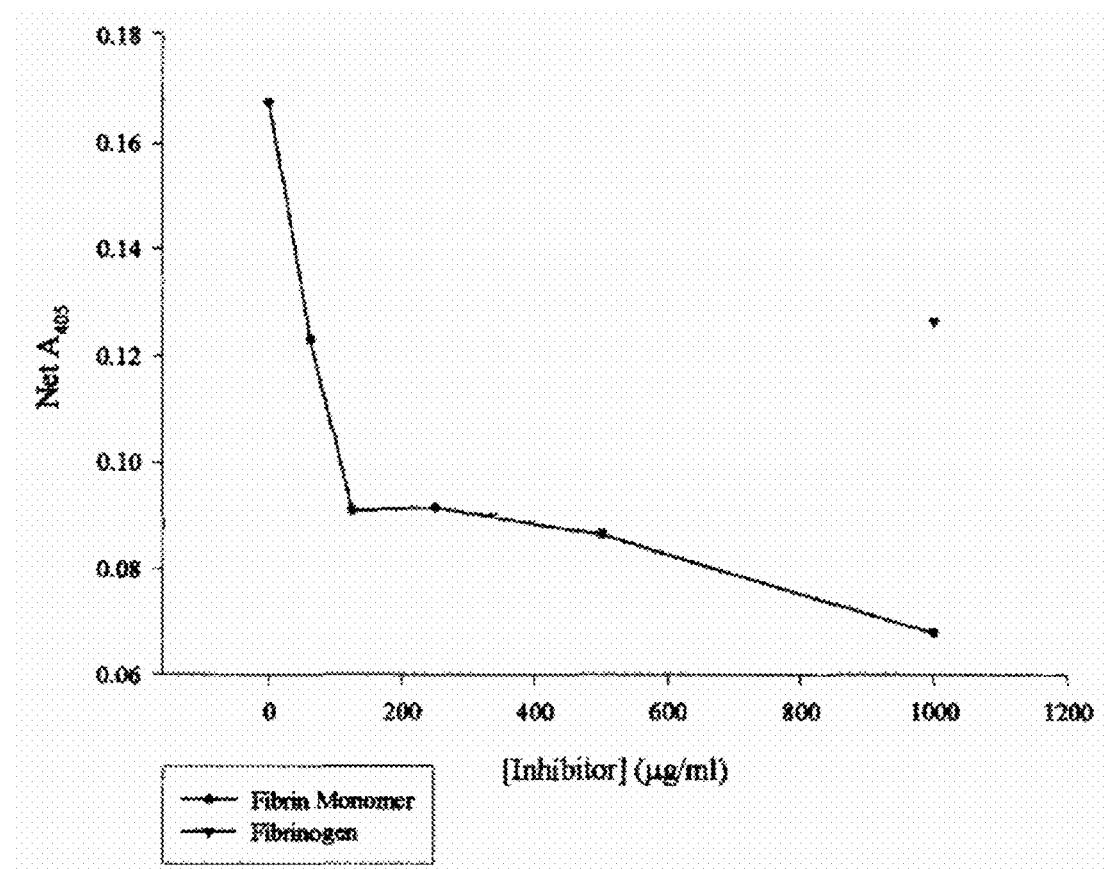
FIG. 4 shows a confirmation of the ELISA plot of FIG. 3 by adding various concentrations of fibrin monomer to the free tPA samples prior to the primary incubation, as described in Example 12.
Figure 5:
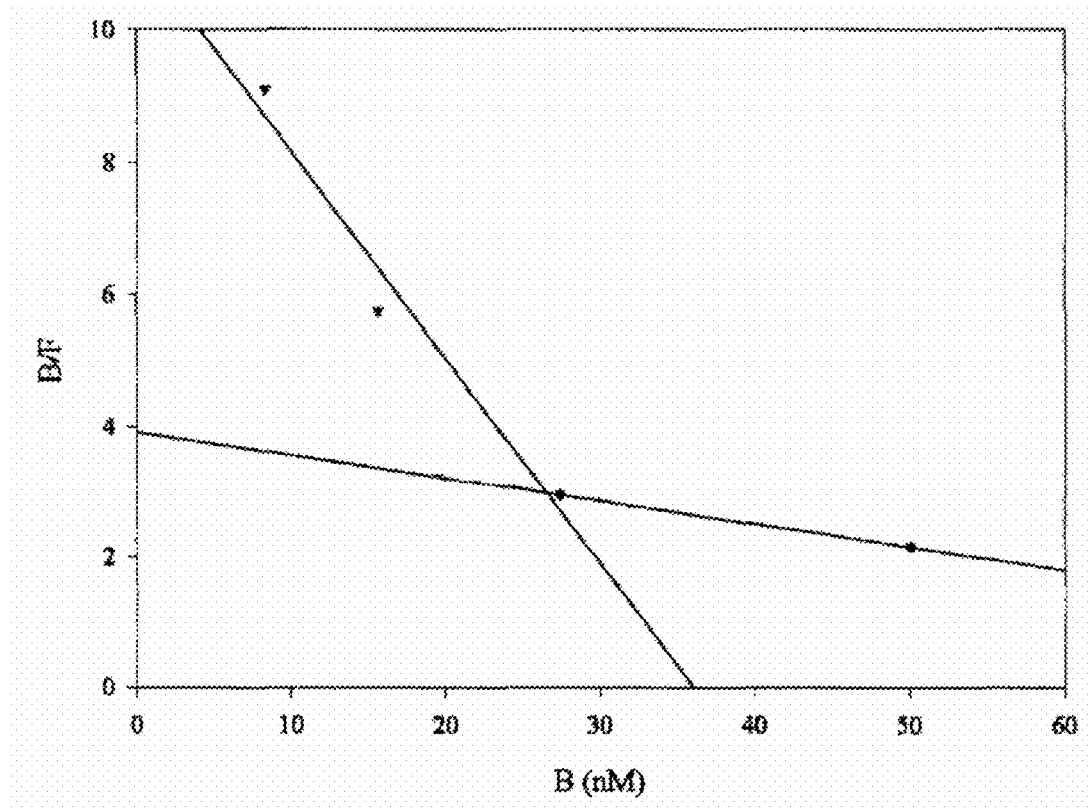
FIG. 5 is a Scatchard plot of free tPA affinity for fibrin, as described in Example 12.

An ELISA plot, exhibiting saturation binding behavior, from a fibrin pad assay that was developed with detection Ab, conjugate and substrate after removal of the free tPA fractions is shown in FIG. 3 (bars=SD, n=4). Fibrin-specificity of the ELISA was confirmed by adding various concentrations of fibrin monomer to the tPA samples prior to the primary incubation (FIG. 4). Fibrinogen exhibited only 5% cross-reactivity with fibrin in this assay. Two affinities (3.19 and 28.3 nM) were readily discernable on the Scatchard plot (FIG. 5; each point is the mean of 3 determinations).

Figure 6:
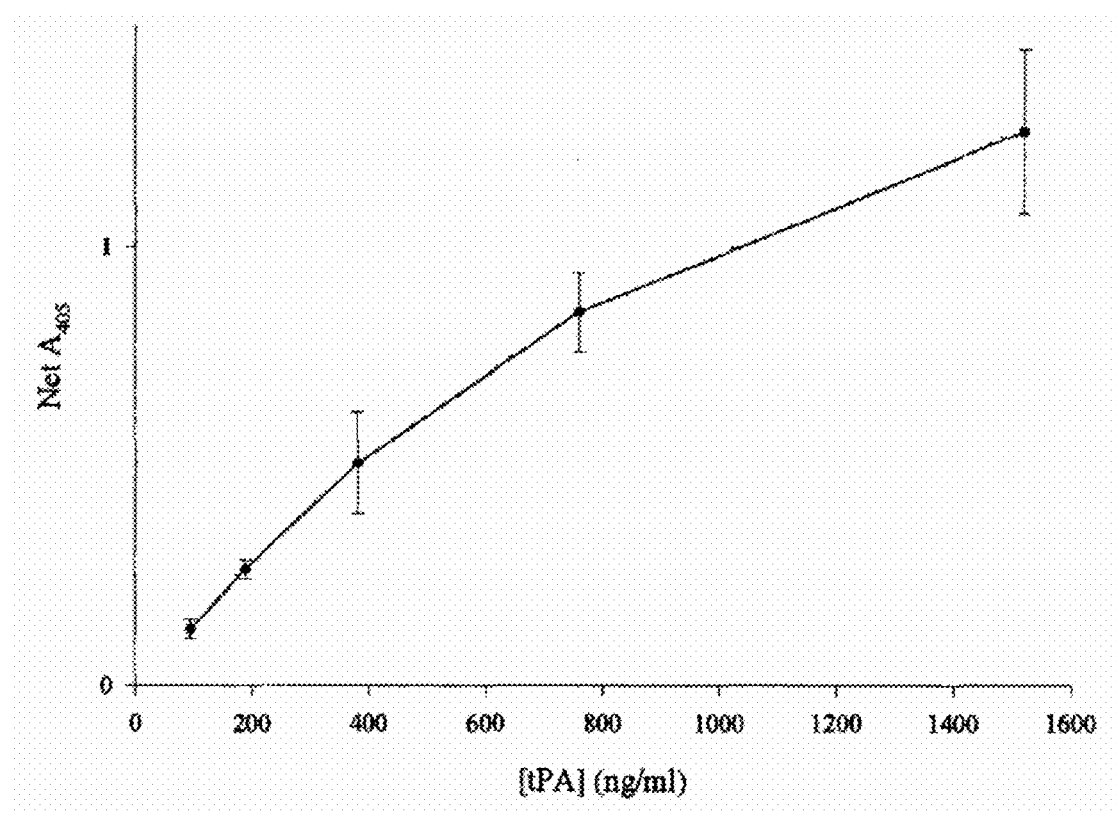
FIG. 6 shows an ELISA plot, exhibiting saturation binding behavior for tPA-loaded ELIP, from a fibrin pad assay as described in Example 12.
Figure 7:
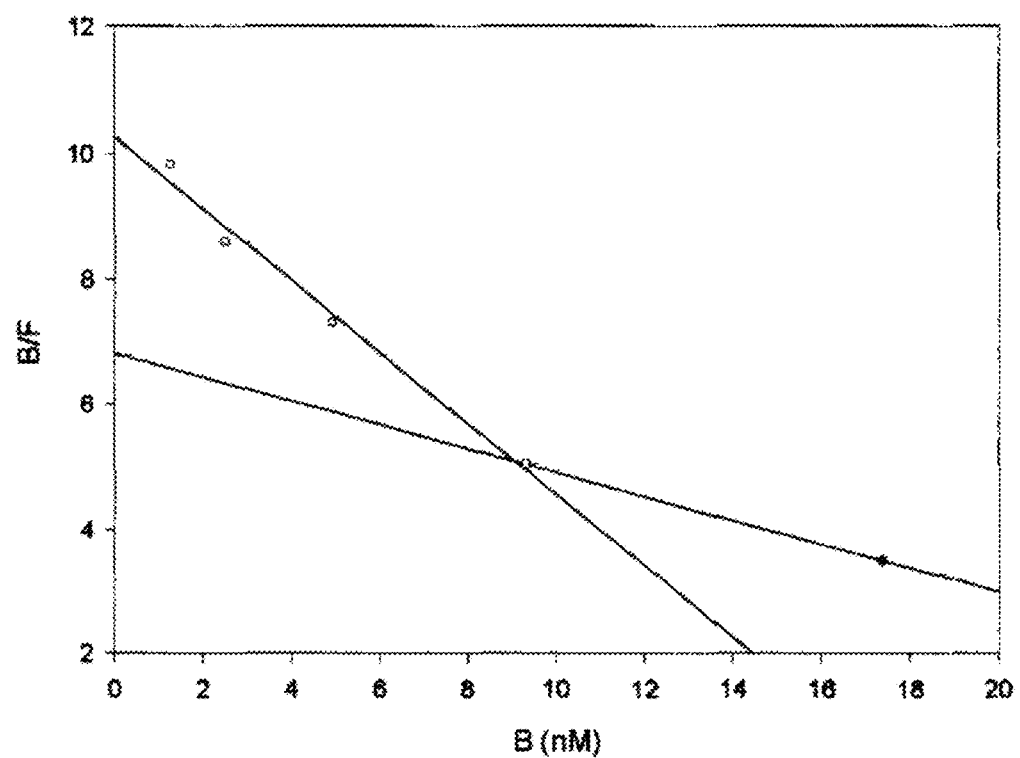
FIG. 7 is a Scatchard plot of tPA-loaded ELIP affinity for fibrin, as described in Example 12.

Tissue plasminogen activator-loaded ELIP also showed saturable binding in the fibrin pad ELISA (FIG. 6) and two affinities in the Scatchard plot (FIG. 7), which were higher than the corresponding affinities exhibited by free tPA (Table 1).

Conclusions

Two previously reported tPA fibrin-binding sites were confirmed with the two-stage ELISA protocol. The higher affinity putatively can be attributed to the finger domain site, and the lower affinity to the Kringle 2 site (2,3). The fibrin-specificity of the binding was also confirmed.

The fibrin-binding sites are fully maintained in tPA-loaded ELIP, with at least equal—perhaps enhanced—affinities for fibrin.

REFERENCES

1. T. Edgell, F. McEvoy, P. Webbon, P. J. Gaffney, Monoclonal antibodies to human fibrin: interaction with other animal fibrins, Thromb. Haemost. 75 (1996) 595-599.
2. J. H. Verheijen, M. P. M. Caspers, G. T. G. Chang, G. A. W. de Munk, P. H. Pouwels, B. E. Enger-Valk, Involvement of finger domain and kringle 2 domain of tissue-type plasminogen activator in fibrin binding and stimulation of activity by fibrin, EMBO J 5(1986) 3525-3530.
3. M. Nesheim, F. C. Fredenburgh, G. R. Larsen, The dissociation constants and stoichiometries of the interactions of lys-plasminogen and chloromethyl ketone derivatives of tissue plasminogen activator and the variant A1 EIX with intact fibrin, J Biol Chem 265(1990)21541-21548.

TABLE 1

Affinities of tPA Fibrin-Binding Sites

|  | Free tPA | tPA-ELIP |
|---|---|---|
| $K_{assoc\ 1}$ | $3.13 \times 10^8\ M^{-1}$ | $5.73 \times 10^8\ M^{-1}$ |
| $K_{assoc\ 2}$ | $3.53 \times 10^7\ M^{-1}$ | $1.93 \times 10^8\ M^{-1}$ |

Example 13

Abstract:

Background:

Ultrasound has been shown to enhance thrombolysis when used in conjunction with a thrombolytic agent. We have loaded echogenic liposomes (ELIP) with tissue plasminogen activator (tPA) and shown that mechanical nonimaging 1 MHz ultrasound can enhance thrombolysis in an in vitro clot model. This study aimed to evaluate the efficacy of clinical Doppler ultrasound to enhance the thrombolytic effect of our tPA-ELIP.

Materials and Methods:

A standard reproducible whole blood porcine clot model was used. Clots were blotted dry, weighed, and placed in 10 ml fresh frozen porcine plasma. Clots were treated with tPA-ELIP with and without Doppler ultrasound (pulsed wave ultrasound, 6.6 MHz, 2 minute-treatment time). After 30 minutes, clots were similarly weighed. Data are reported as percent clot mass loss. Samples of the plasma were assayed for D-dimer levels.

Figure 8:
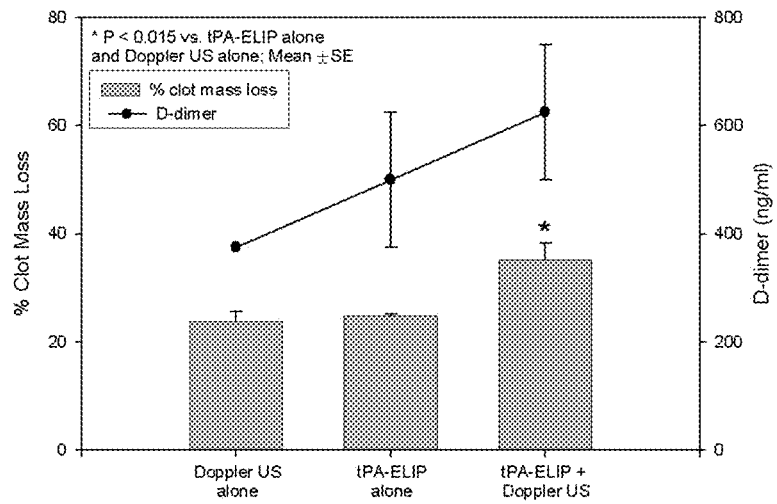
FIG. 8 shows that Exposure of tPA-ELIP to clinical Doppler ultrasound enhanced thrombolysis, as described in Example 13.
Figure 9:
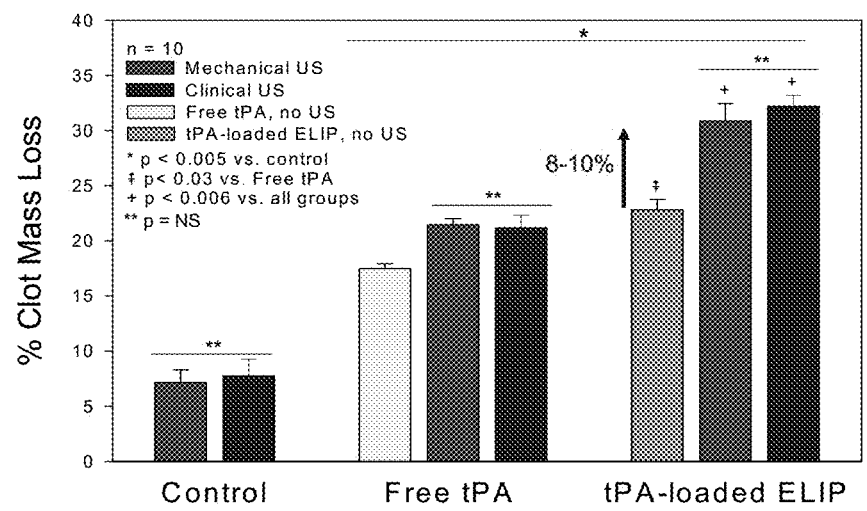
FIG. 9 shows clot mass loss seen in clots treated with tPA-ELIP+clinical Doppler ultrasound, as described in Example 13.
Figure 10:
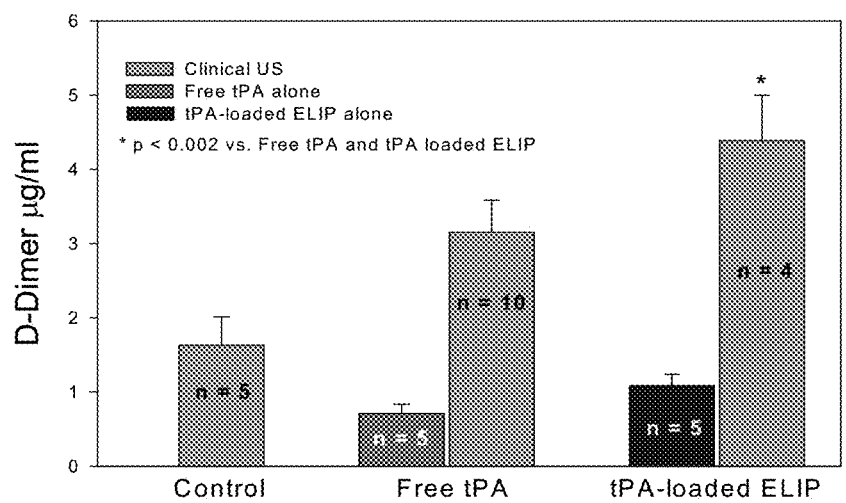
FIG. 10 shows D-dimer levels in clots treated with tPA-ELIP+clinical Doppler ultrasound, as described in Example 13
Figure 11:
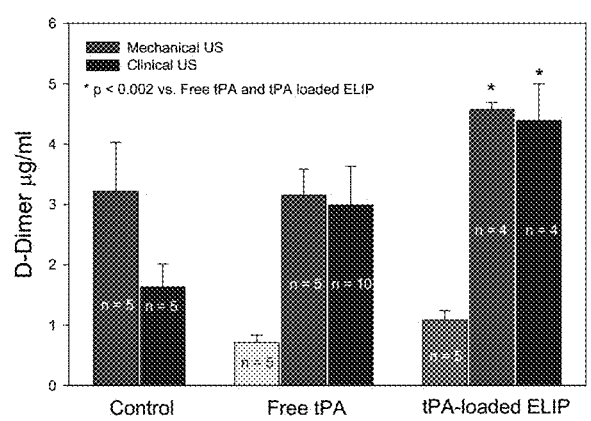
FIG. 11 shows D-dimer levels in clots treated with tPA-ELIP+clinical Doppler ultrasound, as described in Example 13.

Results:

Exposure of tPA-ELIP to clinical Doppler ultrasound enhanced thrombolysis (p<0.015 vs. tPA alone or Doppler ultrasound alone; FIG. 8). There was a trend towards higher D-dimer levels in the clots treated with tPA-ELIP+clinical Doppler ultrasound, corresponding to the higher percent clot mass loss seen in this treatment group (FIGS. 9-11).

Conclusions:

This study demonstrates the ability of clinical Doppler ultrasound to enhance the thrombolytic effect of our tPA-ELIP in an in vitro clot model. This demonstrates the potential to translate our novel thrombolytic technique of combining a thrombolytic-loaded contrast agent and ultrasound to patient care.

Example 14

In Vivo tPA-ELIP Efficacy
Methods:
Animal Model:

New Zealand rabbits (4-5 kg) were used for these studies. All procedures were performed in compliance with CLAMC approved protocols. After the procedure, the animal was sacrificed with a bolus of saturated KCl, and the thoracic and abdominal aortas were removed for histological analysis.

Ultrasound Imaging:

The abdominal aorta was imaged using a Vivid i clinical ultrasound machine with a 13 mMHz 8 L vascular probe (GE Healthcare, Milwaukee, Wis.). A section of the aorta which was most stable for imaging was chosen and external (skin) markers were placed. These markers were used to determine the area for endothelial denudation and thrombus formation. Baseline images were obtained and digitized, including color Doppler and pulse wave spectral Doppler to obtain flow velocities. After thrombus formation and treatment with empty ELIP or tPA-loaded ELIP, the aorta was similarly imaged and flow velocities obtained. Flow velocities distal to the thrombus were measured at baseline, after empty ELIP injection, and after tPA-loaded ELIP injection from time 0 up to 15 minutes.

Thrombus Formation:

A small cutdown incision was made in the right groin. The right femoral artery was exposed and a Cook needle was inserted into the artery. A guidewire was then advanced under fluoroscopic guidance. The Cook needle was removed and a very small (4 French) Fogarty embolectomy catheter (with a central lumen) was "tramlined" over the guidewire into the artery and advanced into the abdominal aorta. The balloon was filled with Visipaque and inflated under fluoroscopic visualization and the catheter moved back over a 5-8 cm area of the abdominal aorta to denude the endothelium; external markers were used to determine the area of denudation. Sodium ricinoleate (0.25 ml) plus fibrin (1.68 mg; 250 U) were mixed in a vial and injected retrogradely through the femoral catheter (with the balloon inflated to limit distal run-off). After 30 seconds following injection, the catheter balloon was deflated.

Treatment:

A small cutdown incision was made in the midline section of the neck. The right carotid artery was exposed and a Cook needle was inserted into the vessel. A guidewire was then advanced under fluoroscopic guidance to the abdominal aorta to the level of the external markers. The Cook needle was removed and a very small (4 French) catheter (with central lumen) was "tramlined" over the guidewire into the artery and advanced into the abdominal aorta. One injection of empty ELIP (nontargeted ELIP; 10 mg lipid) was given intraarterially as control. After 20 minutes, one injection of tPA-loaded ELIP (targeted ELIP; 200 ug/10 mg lipid) was also given intraarterially.

Image/Data Analysis:

Ultrasound images were stored in digital format and transferred to a PC for further quantitative image analyses. All image processing and analyses were performed with Image Pro Plus Software (Ver. 4.1, Media Cybernetics, Silver Spring, Md.). Clots were manually traced and mean gray scale values of the regions of interest were obtained at different time points. Flow velocities in the arterial lumen at different time points were also measured. Results are reported as mean±standard deviation. Groups were compared using the analysis of variance with pairwise multiple comparison performed using the Holm-Sidak method. A p-value of less than 0.05 was considered significant. All analyses were performed using Sigma Stat software (Ver. 3.5, Systat Software Inc, Point Richmond, Calif.).

Figure 12:
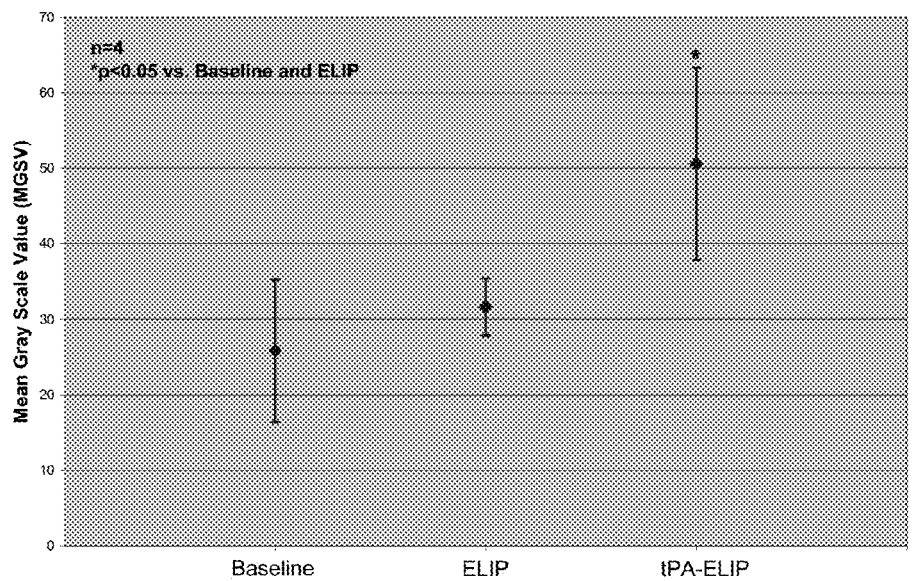
FIG. 12 shows highlighting of thrombus in rabbit aorta after intraarterial injection of tPA-ELIP vs. baseline and control (empty ELIP), as described in Example 14.

Results:

Thrombus formation was observed approximately 2 minutes after injection of the sodium ricinoleate/fibrin mixture. This was consistently produced using the technique described above.

tPA-loaded ELIP highlighted arterial thrombi in vivo (FIG. 12) with mean gray scale values significantly different from baseline and after empty ELIP injection (p=0.12). Qualitatively, following injection with tPA-loaded ELIP, visualization of the arterial thrombus was also improved.

Figure 13:
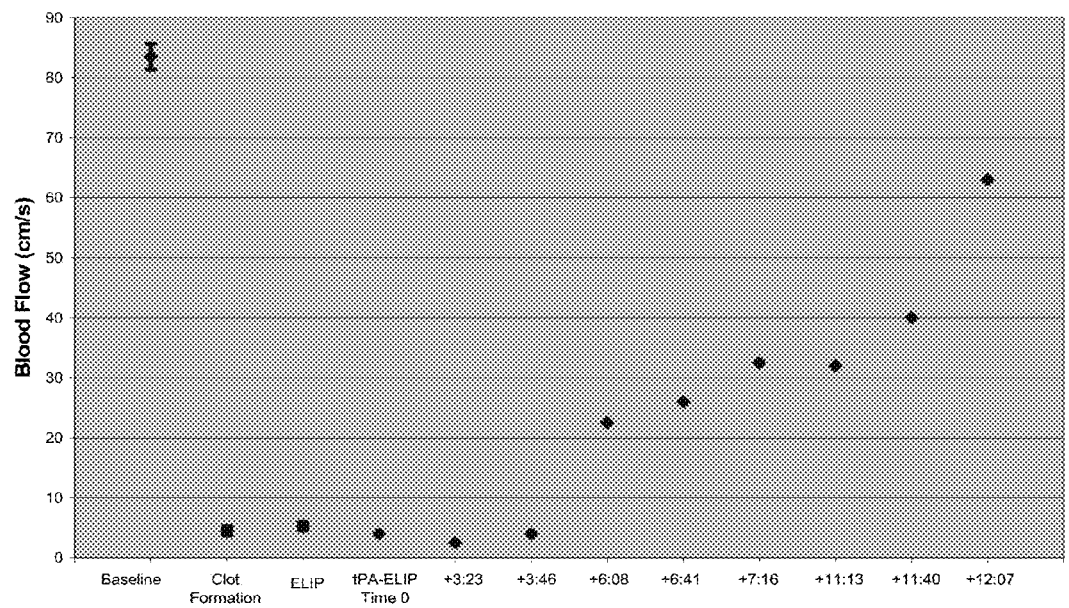
FIG. 13 shows pulse wave Doppler flow velocities in a rabbit aorta, at baseline, following clot formation, after empty ELIP injection, and after injection of tPA-loaded ELIP from time 0 up to 12-15 minutes (n=1), as described in Example 14.

Below is a representative flow velocity graph (FIG. 13) in the rabbit aorta at baseline, following thrombus formation, and treatment with empty ELIP or tPA-loaded BLIP. There was a significant decrease in flow velocities following thrombus formation. There was no change in flow velocities after treatment with empty ELIP. However, 12-15 minutes after injection of tPA-loaded ELIP, there was an increase in flow velocities up to 75% of baseline.

CONCLUSION: tPA-loaded BLIP effectively highlighted arterial thrombus in a rabbit animal model. Preliminary studies also suggest efficacy with regards to thrombolytic effect of the agent.

Example 15

Abstract

Fibrin-specific molecular targeting strategies are desirable for site-specific imaging and treatment of late-stage atheroma, but fibrin-specific antibodies are difficult to produce and present immunogenicity problems. Tissue plasminogen activator (tPA) is an endogenous protein that has been shown to bind fibrin with high affinity and may circumvent antibody difficulties. Use of tPA-derived proteins or peptides, however, requires that the plasminogen-activating proteolytic activity be neutralized or removed. As an initial step in determining the feasibility of this targeting strategy, human recombinant tPA (Activase®) was irreversibly inhibited with D-phe-L-pro-L-arg-chloromethyl ketone (PPACK) and conjugated to intrinsically echogenic liposomes (ELIP) by a thioether coupling protocol. Fibrin-binding affinities were assessed with a novel two-stage fibrin pad ELISA. We achieved 95-99% inactivation, while retaining both tPA fibrin-binding activities of $K_D$~2 nM and 33 nM. Thermodynamic analysis of the PPACK-inactivated tPA (tPA(P)) revealed highly exothermic interactions, indicative of ionic associations, especially for the higher affinity. The conjugation efficiency of tPA(P) to ELIP was within the range of that previously achieved for IgG and exhibited satisfactory fibrin targeting, characterized by striking increases of enthalpy and entropy increments. Evidence for coupling of noncovalent association energetics with the phosphatidylethanolamine major phase transition, observed in previous IgG antibody conjugations, was also evident in this case, but the nature of the transduction mechanism was different. These results demonstrate that tPA-derived components lacking proteolytic activity can be employed as fibrin-targeting agents for delivery of therapeutic and diagnostic formulations.

I. Introduction

Atherosclerosis is the predominant cause of catastrophic cardiovascular incidents, accounting for about 75 percent of all cardiovascular disease (Am. Heart Assoc., 2007). Recent research has established that 70 percent of fatal acute myocardial infarctions and/or sudden coronary deaths result from rupture of "vulnerable" atherosclerotic plaques (atheroma), with sudden formation of occlusive thrombi, rather than from stenotic atheroma (Naghavi et al., 2003). A similar proportion of ischemic stroke is caused by acute thrombolytic events (Eldrup et al., 2006). Much attention, therefore, is being directed toward development of clinical imaging methods for detection of these unstable atheroma and acute thrombi, which would allow prophylactic interventions, such as endarterectomy or aggressive drug therapy. Experimental imaging modalities that employ targeted contrast agents seek to identify target markers that are specific for vulnerable atheroma and acute thrombi. Specifically for vulnerable plaques, fibrin has been identified as a promising molecular marker that can be targeted by contrast agents conjugated to antibodies and other specific ligands (Flacke et al., 2001; Kolodgie et al., 2003). Fibrin is similarly a principal component of acute thrombus formation.

Clinically useful fibrin-binding agents are required to exhibit low cross-reactivity with fibrinogen, which circulates in plasma at a concentration of 30 mg/dl. Some monoclonal antibodies that have strict specificity for human fibrin have been produced (Nieuwenhuizen, 1992; Edgell et al., 1996; Raut and Gaffney, 1996) and utilized in the development of targeted contrast agents (Flacke et al., 2001). The immunogenicity of xenogeneic immunoglobulins, however, necessitates the additional expense of humanizing these reagents for development of clinical products. Fibrin-binding peptides, whether prospectively identified (Koerner et al., 2002; Sirol et al., 2005; Stracke et al., 2007) or recombinantly derived from known fibrin-binding proteins, such as fibronectin (Rosenthall and Leclerc, 1995; Taillefer, 2001), have also been employed as diagnostic targeting agents. These endogenous proteins have the advantage of avoiding immunogenicity drawbacks, while retaining maximal ligand-binding affinities. Human fibronectin is difficult to isolate in clinically useful quantities, however, and the recombinant fibrin-binding fibronectin fragment, as well as randomly generated fibrin-binding peptides, are proprietary formulations marketed for defined commercial applications. Thus, a need exists for identification and development of additional endogenous fibrin-binding entities.

Tissue plasminogen activator (tPA) is known to possess two fibrin-binding domains, a higher affinity site in the finger domain and a lower affinity site in the Kringle 2 (K2) domain, which is mainly responsible for fibrin potentiation of catalytic activity (Verheij en et al., 1986). Studies relying on tPA binding to fibrin clots reported relatively low affinities for both domains (Nesheim et al., 1990; Bringmann et al., 1995); being in the micromolar range, they were of questionable clinical utility. Other studies, relying on immunoassay methodology and surface plasmon resonance, however, reported much higher affinities, in the low nanomolar range (Angles-Cano, 1986; Tsurupa and Medved, 2001).

We have reproduced Angles-Cano's results for average tPA-fibrin affinity, using a modification of his SOFIA-tPA method (Tiukinhoy-Laing et al., 2007). More recently, we have been able to discriminate both binding affinities using an enzyme-linked immunosorbent assay (ELISA) protocol that can be adapted to thermodynamic analysis of the binding interactions (Klegerman and McPherson, 2007).

Others have utilized radiolabeled tPA, irreversibly inactivated with D-phe-L-pro-L-arg-chloromethyl ketone (PPACK), as a fibrin targeting agent for radiologic imaging of thrombi (Ord et al., 1992; Reno et al., 1993). In the present study, we have adapted this strategy as an initial attempt to demonstrate that tPA-derived species can serve as suitable fibrin targeting agents for intrinsically echogenic liposomes (ELIP), which we have developed for site-specific diagnostic and therapeutic applications. Previously, we demonstrated that ELIP conjugated to polyclonal and monoclonal anti-fibrin antibodies produced significant ultrasound highlighting of fibrin preparations and thrombi in vitro and in vivo (Demos et al, 1997; Demos et al., 1999; Hamilton et al., 2002; Hamilton et al., 2004). Demonstration of ELIP targeting to fibrin in the present study would permit inactivated tPA to be used as a sole targeting moiety on a vesicle that has the potential to highlight vulnerable plaque and acute thrombi, as well as to deliver therapeutic agents to these active sites.

II. Materials and Methods

A. Materials

Recombinant single-chain tPA (Cathflo Activase®) was manufactured in 2-mg quantities by Genentech (South San Francisco, Calif.). Human fibrinogen, PPACK·2HCl and glu-type human plasminogen were obtained from Calbiochem (EMD Biosciences, Inc., La Jolla, Calif.). D-val-L-leu-L-lys-p-nitroanilide·2HCl, 3-(2-pyridyldithio)propionic acid-N-hydroxysuccinimide ester (SPDP), thrombin, donkey anti-sheep IgG-alkaline phosphatase conjugate, p-nitrophenyl phosphate substrate, ε-aminocaproic acid (EACA), bovine serum albumin (BSA), Tween-20, sodium azide, cholesterol, Sephadex G-50 and Sepharose CL-4B were purchased from Sigma-Aldrich (St. Louis, Mo.). L-arginine, Nunc MaxiSorp microtiter plates and buffer salts were purchased from Fisher Scientific. Mouse monoclonal anti-tPA was obtained from Abcam, Inc. (Cambridge, Mass.), and sheep anti-tPA from AbD Serotec (MorphoSys, Oxford, UK). Phospholipids were from Avanti Polar Lipids (Alabaster, Ala.). Normal rabbit serum (NRS) was prepared by centrifugation of clotted whole blood, obtained by venipuncture of New Zealand White rabbits according to an approved UTHSC-H protocol, and was immediately stored in aliquots at −20° C.

B. Inactivation of tPA

Reconstituted tPA was incubated with a fivefold molar excess of PPACK in 0.2 M L-arginine in 0.05M phosphate buffer, pH 7.2, with 0.01% Tween 20 for 1 hour at room temperature, followed by dialysis against reaction buffer to remove unreacted PPACK. A control preparation was carried through the procedure without PPACK and all procedures involving PPACK were protected from light. Enzyme activity in PPACK-treated and control tPA preparations was measured with a colorimetric paranitroanilide-substrate method (Ranby and Wallen, 1981).

C. Two-Stage Fibrin Pad ELISA

Dilutions of untreated, sham-treated (control) and PPACK-treated (tPA(P)) tPA, as well as tPA(P) conjugated to ELIP (tPA(P)-ELIP), were incubated on replicate fibrin pads, prepared in microplate wells according to a modification of the method of Edgell et al. (1996). Human thrombin was added to a solution of 0.5 mg/ml of human fibrinogen in 0.02M phosphate-buffered saline, pH 7.4 (PBS), to a final concentration of 0.125 IU thrombin/ml; 100 µl of this solution was immediately added to each well and incubated at 37° C. for 45 minutes, followed by overnight drying of the plate at 45° C. After incubation with 100 µl/well of 0.2% BSA in PBS for 1 hour, samples (100 µl/well) were incubated for 2 hours at 37° C. For thermodynamic analyses, this incubation was performed at three temperatures (5, 24 and 37° C.). In order to determine the concentration of free tPA remaining in solution after incubation of tPA with fibrin, from which the concentration of bound tPA could be calculated for Scatchard analysis, the contents of duplicate wells were recovered, pooled and subsequently assayed for immunoreactive tPA in a standard quantitative sandwich ELISA.

Briefly, Nunc MaxiSorp microtiter plates were coated with 5 µg/ml of a monoclonal anti-tPA capture antibody (Ab) in 0.05M sodium bicarbonate, pH 9.6, overnight at 4° C. All incubation volumes were 50 µl/well. One-half of wells were left uncoated for determination of nonspecific binding. After aspirating well contents, all wells were blocked with conjugate buffer (1% BSA in 0.05M Tris buffer, pH 8.0, with 0.02% sodium azide) for 1 hour. From this point, all incubations were at 37° C. Each incubation was followed by aspiration of well contents and washes (3×) with PBS-T (PBS with 0.05% Tween 20).

Various dilutions of tPA, tPA(P) or tPA(P)-ELIP in PBS-T (2-3 replicates per dilution) were incubated for 2 hours. All wells were then incubated with 10 µg/ml of a secondary polyclonal sheep anti-tPA detection Ab in 0.1% BSA/PBS-T diluent for 1 hour, followed by a 1-hour incubation with 1:3,000 donkey anti-sheep IgG-alkaline phosphatase in conjugate buffer. The substrate incubation consisted of 50 µl of substrate buffer (0.05M glycine buffer, pH 10.5, with 1.5 mM magnesium chloride)+50 µl p-nitrophenyl phosphate (4 mg/ml) in substrate buffer per well for 15 minutes. The reaction was stopped with 50 µl 1M sodium hydroxide per well. The optical absorbance of each well at 405 nm ($A_{405}$) was measured with a Tecan Safire² microplate reader (Tecan U S, Research Triangle Park, N.C.). Net $A_{405}$ was determined by subtracting the absorbance of background wells from that of capture Ab-coated wells; tPA concentrations of samples were calculated relative to tPA standards in the corresponding diluent.

Binding affinities at each temperature were determined from Scatchard plots of bound tPA concentrations ([total tPA added to fibrin pad well]−[free tPA recovered]) vs. the ratio of bound tPA/free tPA. For thermodynamic analyses, the standard enthalpy change ($\Delta H°$) of the tPA-fibrin association was determined from van't Hoff plots of 1/T vs. log $K_{assoc}$; the standard Gibbs' free energy ($\Delta G°$) and entropy ($\Delta S°$) changes were calculated from equations of state. ELISA and affinity determinations were repeated for tPA(P) and tPA(P)-ELIP dilutions at 37° C. in undiluted normal rabbit serum (NRS). Ionic strength dependence of tPA-fibrin binding was studied by carrying out affinity determinations for Activase® in PBS-T containing various concentrations of added sodium chloride.

D. Preparation and Characterization of tPA(P)-ELIP

MPB-ELIP, consisting of egg L-α-phosphatidylcholine (PC), 1,2-dipalmitoyl-sn-glycero-3-phosphoethanolamine-N[4-(p-maleimidophenyl)butyrate] (MPB-PE), 1,2 dipalmitoyl-sn-glycero-3-phosphoglycerol (DPPG) and cholesterol (CH) in a 69:8:8:15 molar ratio, were prepared by a dehydration-rehydration method (Demos et al., 1997) and conjugated to tPA via a thioether linkage, in which a protein thiol adds to the unsaturated MPB-PE maleimido ring. Methylthiol groups were coupled to protein amino functions using SPDP (Torchilin et al., 2003). The conjugation procedure was carried out essentially as previously described for rabbit IgG (Klegerman et al., 2002), except that ELIP-conjugated tPA was separated from unconjugated tPA by chromatography on a 20-ml Sepharose CL-4B column by the method of Lasch et al. (2003). Alternatively, 0.01% Tween 20 was added to all buffers used for preparation of the thiolated protein in order to determine whether addition of detergent would improve the yield and integrity of conjugated tPA.

Protein yields during thiolation were measured with the Lowry protein assay (Scopes, 1982) relative to tPA standards. Conjugation efficiency was determined by an indirect immunoblot assay (IBA) in which tPA(P)-ELIP dilutions were spotted onto nitrocellulose membranes, followed by a 3% gelatin blocking incubation, as previously described for IgG-ELIP (Klegerman et al., 2002). A one-hour incubation with the monoclonal anti-human tPA (5 µg/ml 1% gelatin in 0.02M Tris-buffered saline with 0.05% Tween 20) used as capture Ab for the tPA sandwich ELISA was added prior to anti-mouse IgG-alkaline phosphatase conjugate incubation and colorimetric substrate staining. The concentration of anti-tPA Ab bound to liposomal tPA was determined relative to IgG-ELIP standards. IgG concentrations were converted to tPA concentrations by normalizing for differences in molecular weight and Ab:Ag valence, from 1:2 at low sample dilutions to 1:1 at high sample dilutions. The resultant tPA concentrations determined for the undiluted tPA(P)-ELIP preparation were consistent for all dilutions assayed. Enumeration and particle size distribution analysis of tPA(P)-ELIP were performed with a Beckmann-Coulter Multisizer 3 fitted with a 20 µm aperture tube, which enabled particle sizing down to 0.4 µm equivalent spherical diameter.

Dilutions of liposome preparations were imaged with a 20 MHz intravascular ultrasound (IVUS) catheter (SciMed, Inc., Sunnyvale, Calif.) in glass vials. Relative echogenicity (apparent brightness) of the samples were objectively assessed using computer-assisted videodensitometry. This process involved image acquisition, pre-processing, liposome identification, and gray scale quantification. All image processing and analyses were performed with Image Pro Plus Software (Ver. 1.0, Media Cybernetics, Silver Spring, Md.) running on a dedicated computer (486 CPU, 66 MHz). Images were digitized to 640×480-pixel spatial resolution (approximately 0.045 mm/pixel) and 8-bit (256 level) amplitude resolution. Data are reported as mean gray scale values (MGSV).

E. Statistics

Population variance was determined by normal parametric analysis. Scatchard (n=16-24) and van't Hoff (n=48–72) data were subjected to linear regression analysis of individual points. Free tPA values of samples recovered from fibrin pad wells were calculated from standard curves comprising a hyperbolic fit of ELISA data. All regression analyses were performed with Sigmaplot 2000 software. The standard errors of affinities in the ionic strength dependence study were calculated from the standard error of the slope ($S_b$) for the respective Scatchard regressions.

III. Results

A. Fibrin Pad ELISA-Derived Affinities

Figure 14:
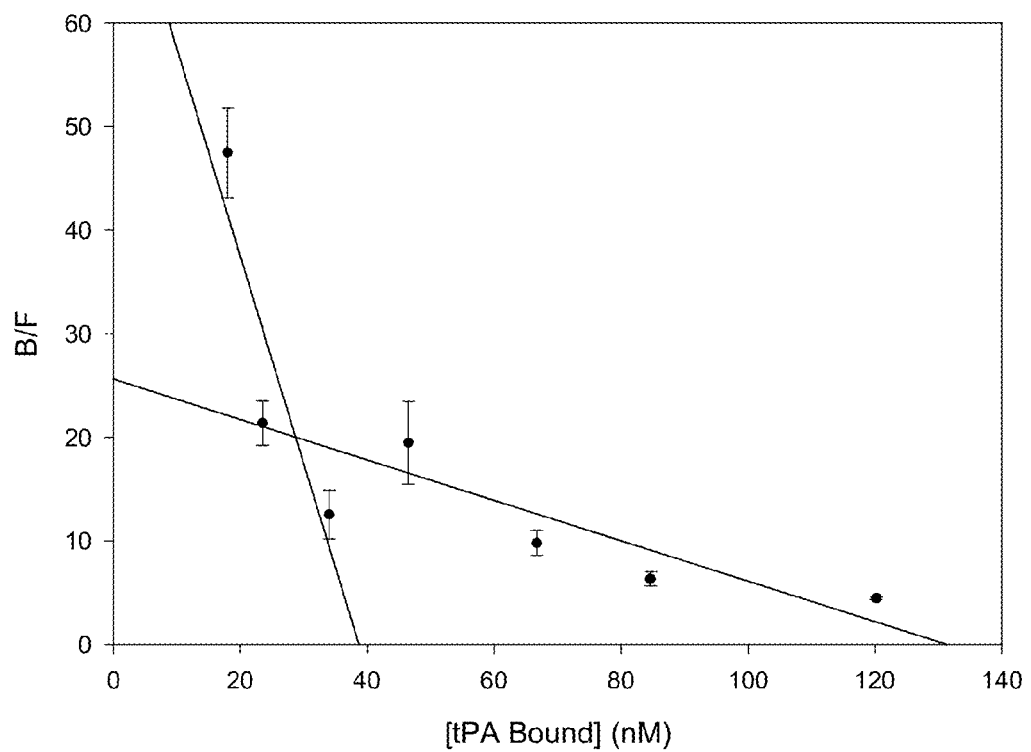
FIG. 14. Representative Scatchard plot of tPA (Activase®) fibrin pad binding in PBS-T at 37° C., as described in Example 15. Each point is the mean of 4 determinations; bars=S.D. High affinity=$2.00 \times 10^9$ $M^{-1}$ (r=0.883); low affinity=$1.95 \times 10^8$ $M^{-1}$ (r=0.904).

Two distinct affinities were readily discernable in Scatchard plots derived from tPA levels after incubation on fibrin pads at 37° C. (FIG. 14). High-affinity interaction dissociation constants ($K_D$) were 5.81±4.04 (SE, n=3) nM, which is comparable to that (1.4±2 nM) found by Angles-Cano (1986), using the SOFIA-tPA assay. Low-affinity interaction $K_D$'s were 30.4±14.7 nM, which is very similar to the 33±5 nM value reported by Tsurupa and Medved (2001) for the K2 site, which was completely inhibited by ε-aminocaproic acid (EACA).

B. Inactivation of tPA

The low-affinity interaction was not discernable in the control preparation, but the high-affinity fibrin-binding capacity was fully retained after PPACK inactivation, while the enzyme was more than 95 percent inactivated (Table 1). In the thermodynamic study of tPA(P)-fibrin binding, the low affinity value at 37° C. was essentially the same as previously found for tPA (Table 2).

C. tPA(P)-ELIP Preparation and Characterization

Approximately half of the tPA (2 mg) inactivated for ELIP conjugation was recovered after dialysis. The normal conjugation procedure, in which no detergent is added to buffers used for protein thiolation, resulted in yields of activated and thiolated protein that were about half of that normally obtained for IgG conjugations, while thiolation efficiency was in the optimal range (Table 3). Conjugation efficiency, expressed as a mass ratio, was also somewhat lower than previously measured values (even when adjusted for differences in ligand molecular weight), but the number of molecules coupled per liposome (912) approached the optimization threshold determined in previous studies of Ab ligands (Klegerman et al., 2007). Since high-affinity fibrin binding was fully retained by this preparation, ELIP avidity ($K_{assoc}$×no. ligand molecules/liposome) was consequently about one-fourth of the optimal value, corresponding to slightly more than half-maximal retention in a flow chamber under physiologic conditions (Demos et al., 1998).

Figure 15:
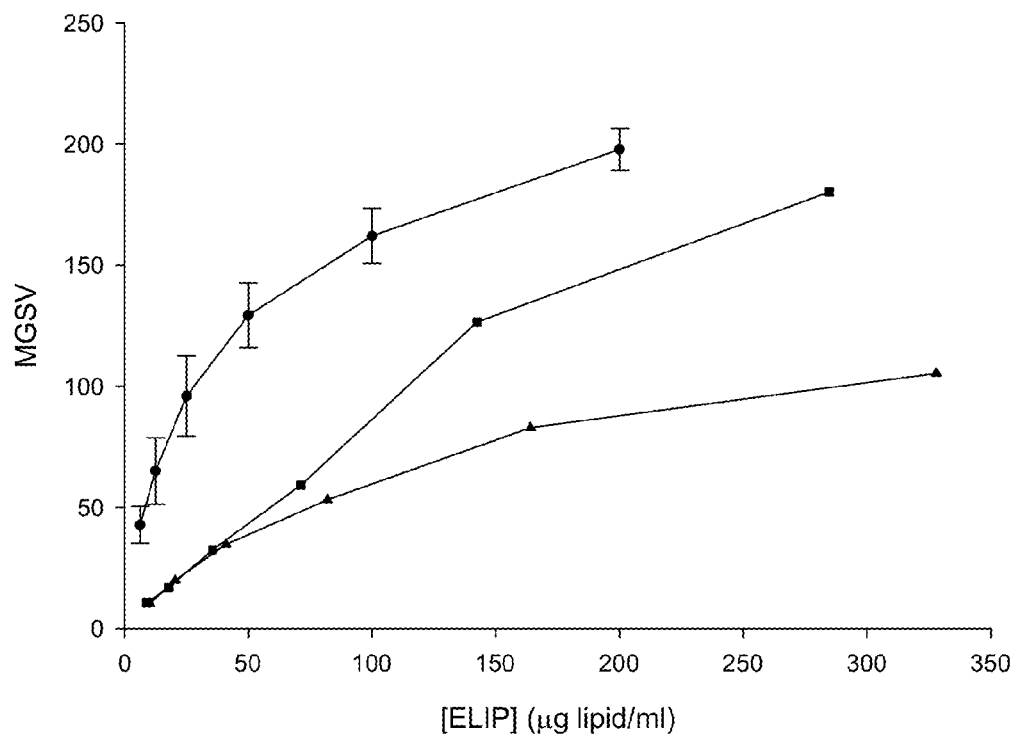
FIG. 15. Echogenicity of ELIP preparations: dose response. ELIP dilutions in glass vials were imaged with a 20 MHz IVUS catheter. Average sonogram field brightness was converted to mean gray scale values (MGSV) by digital image analysis, as described in Example 15. Circles: unconjugated ELIP (n=6-7, bars=SD); squares: tPA(P)-ELIP prepared without added detergent; triangles: tPA(P)-ELIP prepared with 0.01% Tween 20 added to tPA(P) thiolation buffers.

Addition of 0.01% Tween-20 to the buffers used for SPDP activation and DTT reduction of the PPACK-inactivated tPA did not improve measures of ELIP targeting efficiency (Table 3). The resultant ELIP avidity for fibrin was about one-third of that obtained with tPA(P) prepared in the absence of detergent. The echogenicity of the reconstituted final product was also poorer for this preparation, exhibiting a MGSV of 100 (out of 255 levels) at an ELIP concentration of 285 μg lipid/ml, compared to a value of 180 at the corresponding concentration of the other preparation, which is typically found for unconjugated ELIP at that concentration (FIG. 15). In both cases, Multisizer 3 analysis revealed a single broad peak below 1 μm, with a median equivalent spherical diameter ($d_{sn}$) of 695-730 nm. The liposome yield of tPA(P)-ELIP prepared without detergent was about twice that of the detergent-added batch, being $1.37 \times 10^{10}$/mg lipid, compared to $7.16 \times 10^9$/mg lipid.

Figure 16:
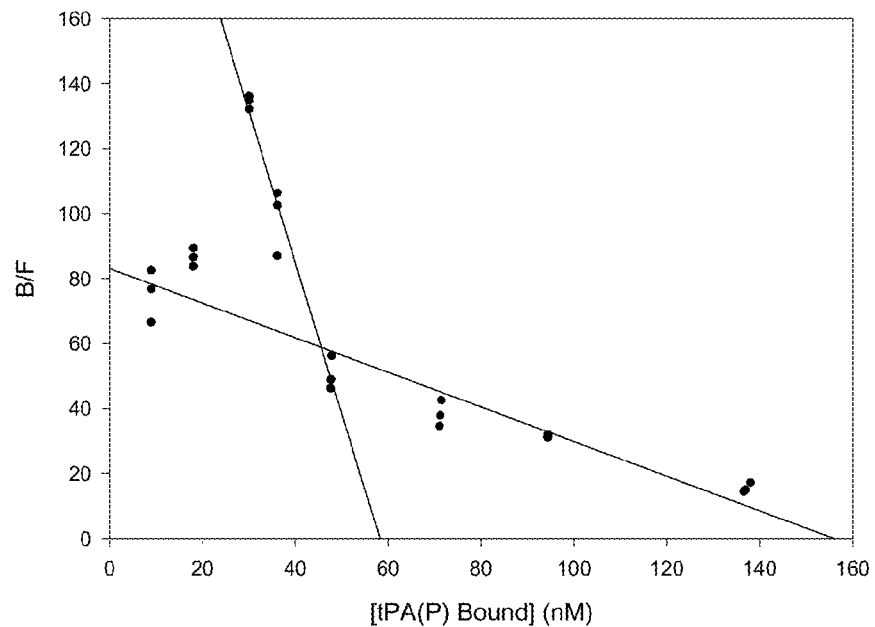
FIG. 16. A. Scatchard plot of tPA(PPACK) binding to fibrin pads at 5° C., as described in Example 15. B. tPA (PPACK) fibrin pad ELISA van't Hoff plots, as described in Example 15. Filled circles: low-affinity binding; open circles: high-affinity binding.
Figure 16:
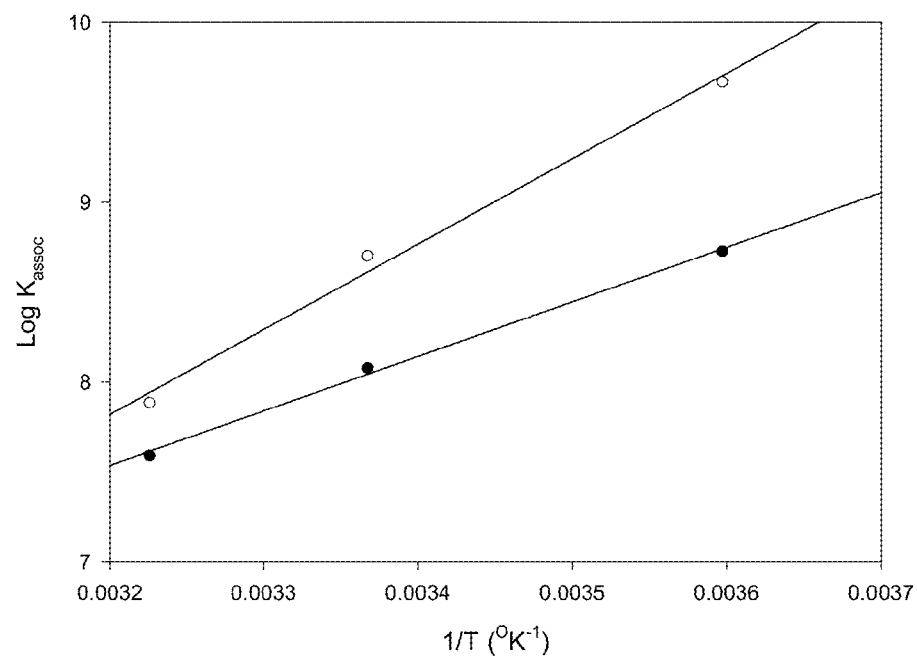
Figure 17:
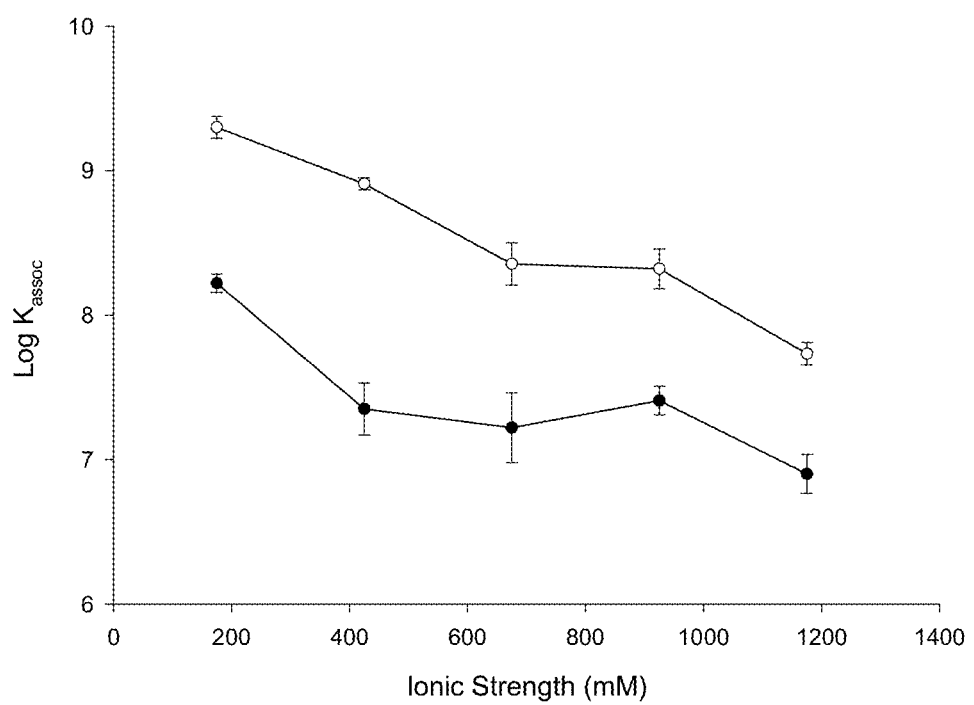
FIG. 17. Ionic strength dependence of tPA-fibrin binding affinities, as described in Example 15. Filled circles: low-affinity interactions; open circles: high-affinity interactions. Bars=S.E. (n=12-24); log $K_{assoc}$<7 signifies undetectable affinity (not significantly different from zero).
Figure 18:
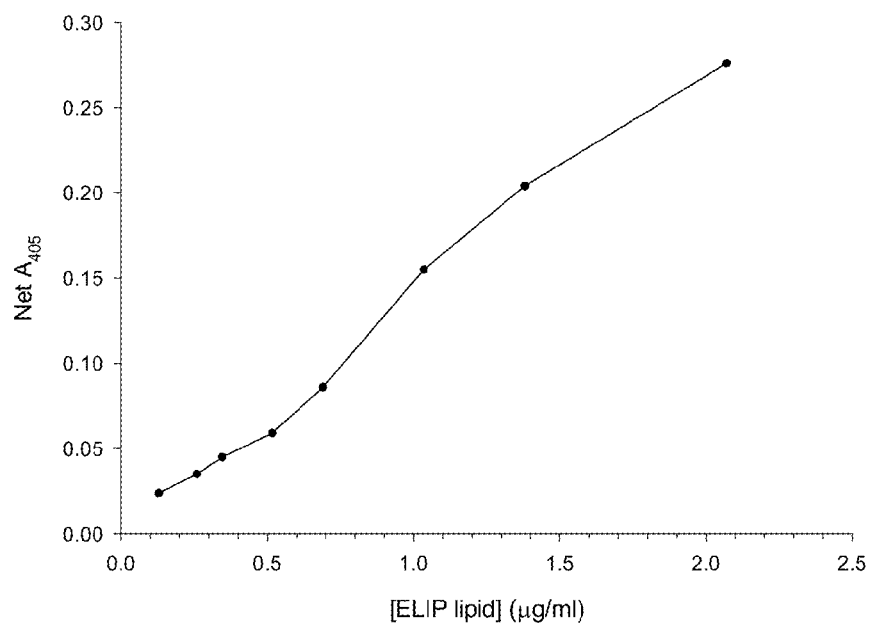
FIG. 18. A. Fibrin pad ELISA dose response curve for tPA(P)-ELIP in PBS at 24° C., as described in Example 15. Each point is the average of two determinations. Net $A_{405}$ is normalized for response in the presence of PBS alone. B. Scatchard plot of tPA(P)-ELIP binding to fibrin pads at 5° C., as described in Example 15.
Figure 18:
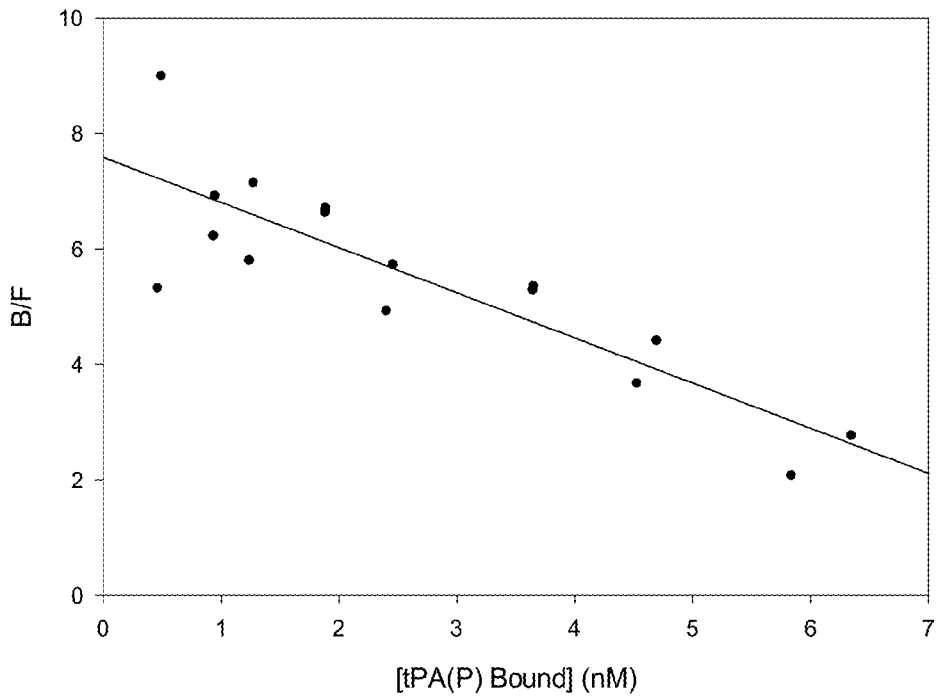

D. Thermodynamic Analysis of Unconjugated and ELIP-Conjugated tPA(P)-Fibrin Binding Bimodal binding of tPA(P) to fibrin pads was observed in the thermodynamic series (FIG. 16A). For both tPA fibrin binding sites, the affinity increased steeply with decreasing temperature, indicative of highly exothermic association kinetics (Table 2, FIG. 16B). Both fibrin-binding interactions were characterized by high negative standard enthalpy and entropy changes, consistent with ionic forces, the high-affinity association more purely so. Both binding affinities exhibited parallel inhibition with increasing ionic strength (analysis performed on intact tPA; FIG. 17), consistent with the ionic nature of the interactions. Specific binding of both tPA(P)-ELIP preparations to fibrin was clearly demonstrated in the ELISA (FIG. 18A), making either preparation suitable for thermodynamic analysis, which was performed on the detergent-treated preparation. In both cases, the low-affinity binding capacity was apparently abolished by the conjugation procedure, since unimodal association behavior was seen in all the Scatchard plots (e.g., FIG. 18B). The association constants found were similar to the high-affinity series of the unconjugated preparation (Table 4), except that the temperature dependence was less pronounced (resulting in a shallower slope of the van't Hoff plot regression line), reflecting a striking increase in both ΔH° and ΔS°. This has previously been observed for Ab-ELIP preparations (Klegerman et al., 2007).

Figure 19:
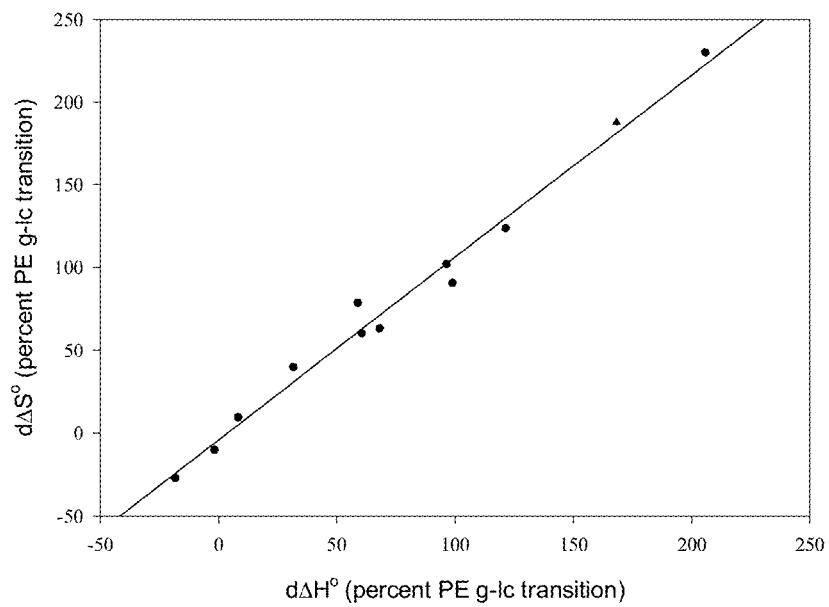
FIG. 19. A. Correlation of standard enthalpy and entropy increments upon protein-ELIP conjugation relative to corresponding values for the PE gel-liquid crystalline phase transition, as described in Example 15. Circles: previously obtained data for IgG whole Ab and IgG Fab conjugations (11 series); triangle: data for tPA(P)-ELIP obtained in the present study. B. Interaction dependence of PE major phase transition coupling of protein-ligand association energetics, as described in Example 15. Circles: X═H (kcal/mole), inverted triangles: X═S) (cal/mole°; filled symbols: previously obtained data for IgG whole Ab and IgG Fab conjugations, open symbols: data for tPA(P)-ELIP obtained in the present study.
Figure 19:
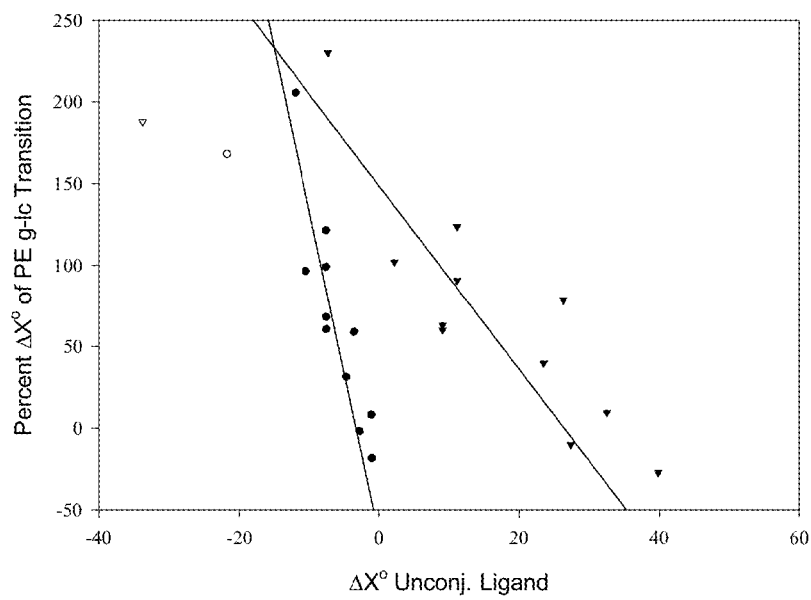

The present data were examined to determine whether the tPA-fibrin interaction relates to the major PE phase transition similarly to what we previously observed for Ab-ELIP (Klegerman et al., 2007). The tPA-ELIP data appear to belong to the same regression population as the Ab-targeted ELIP data regarding PE phase transition coupling (FIG. 19A), but not regarding the interaction dependence (FIG. 19B).

E. Confirmation of Binding Site Identities

In the presence of 50 mM EACA, one tPA fibrin-binding affinity decreased to a non-measurable level, while the other was found to be 32.9 nM (data not shown). Under the same conditions, tPA(P)-ELIP fibrin binding persisted and exhibited a $K_D$ of 6.41 nM, assigning the high-affinity fibrin association to the lysine-independent finger domain and suggesting that the high-affinity fibrin-binding function of intact tPA is partially inhibited by abrogation of the Kringle 2 fibrin-binding function.

F. tPA(P) Fibrin Binding in Serum

The ELISA dose-response behavior of unconjugated tPA (P) and tPA(P)-ELIP binding to fibrin pads in the presence of undiluted fresh-frozen rabbit serum was nearly identical to that in PBS. The binding affinities ($K_D$) at 37° C. were 9.52 and 3.91 nM, respectively.

IV. Discussion

The study described in this report aimed to evaluate irreversibly inactivated tPA as a fibrin-targeting agent for echogenic liposomes, thus providing the advantages of a high-affinity endogenous ligand to this application. In this initial study, we have succeeded in effectively eliminating more than 95 percent of the tPA enzymic activity with PPACK, while fully retaining both fibrin-binding functions. Utilizing our customary thioether conjugation protocol, we were able to achieve near-optimal coupling of the inactivated tPA to ELIP. Retention of the tPA(P)-ELIP high-affinity fibrin targeting capability allowed thermodynamic analysis of this molecular interaction. In this discussion, we will evaluate our findings in some detail, assess their implications and significance, and identify future directions of study.

In previous ELISA studies of tPA binding to fibrin monolayers, prepared as described for conjugation of anti-fibrin antibodies to ELIP (Klegerman et al., 2007), we noted a relatively high nonspecific binding. As tPA is a somewhat hydrophobic protein, requiring addition of detergent and L-arginine to prevent aggregation (Cheng et al., 1995), though not to be bound by theory, we currently understand that partial denaturation of fibrinogen adsorbed to plastic multiwell plates may promote nonspecific association of tPA hydrophobic residues with analogous residues exposed on the immobilized fibrinogen.

In order to ensure that the observed association kinetics were due to specific binding of tPA to fibrin, we adapted the fibrin pad ELISA method of Edgell et al. (1996) to a protocol in which the primary incubation solutions were recovered and assayed for immunoreactive tPA, providing free tPA levels for Scatchard analysis. The results agreed well with previous affinities found by us and Angles-Cano (1986), using a SOFIA-tPA assay that enables direct Scatchard analysis based on measurement of tPA enzyme activity. A lower affinity was also detected, however, with the two-stage fibrin pad ELISA, corresponding to that reported for the Kringle 2 site by Tsurupa and Medved (2001), which required assay of higher tPA concentrations than were included in the SOFIA-tPA study.

Both fibrin-binding functions were retained after PPACK inactivation, which eradicated 95-99 percent of the plasminogen-specific proteolytic activity. While the lower affinity binding appeared to be somewhat labile, being lost in a control preparation, in the presence of undiluted normal rabbit serum and during conjugation to ELIP, the high-affinity site is relatively robust. The thermodynamics of both tPA fibrin-binding functions, determined by multi-temperature ELISA as previously performed for Ab-antigen (Ag) interactions (Klegerman et al., 2007), indicated a predominance of ionic interactions, especially in the case of the high-affinity association, which has been attributed to the finger domain (Nesheim et al., 1990). In this study, we have confirmed that high-affinity fibrin binding by intact tPA and by tPA(P)-ELIP in our experimental system is lysine-independent, being relatively unaffected by EACA, therefore assigning it to the finger domain, while the observed low-affinity binding is a lysine-dependent function of the K2 domain.

Figure 20:
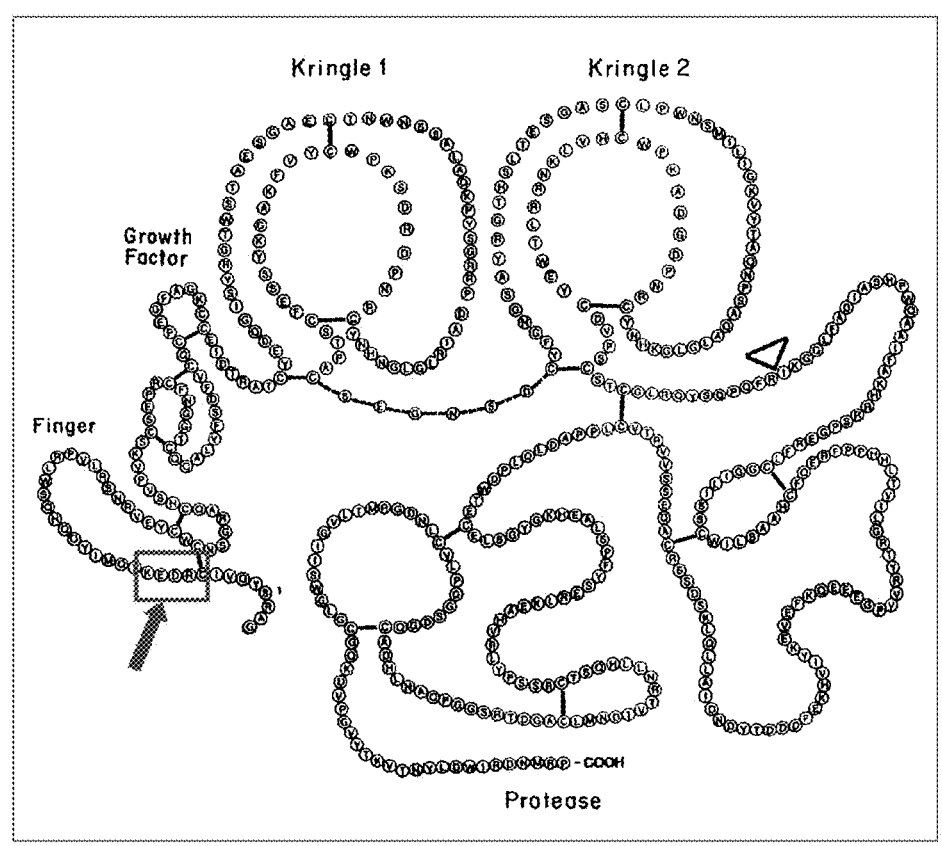
FIG. 20. Putative high-affinity fibrin-binding site in the tPA finger domain, based on the thermodynamics of tPA(P) binding to fibrin pads, as described in Example 15. Box and arrow indicate the 4 residues necessary for the binding characteristics.

Based on thermodynamic studies of zinc finger peptides (Blasie and Berg, 2002; 2004), the $\Delta H°$ and $\Delta S°$ obtained suggests the association of four basic/acidic residue pairs, comprising optimal hydrogen bonding and long-range electrostatic interactions. These 4 residues can be found in the finger domain near the N-terminus of the tPA A-chain (RDEK, FIG. 20). We have also identified a complementary site in the fibrinogen γ-chain, in the FCB-5 region implicated as a tPA-binding site that does not contribute to the fibrin-induced potentiation of tPA enzyme activity (Yonekawa et al., 1992), comprising the DKFE tetrapeptide, especially if the lys-338 is proximal to the phe-322.

When tPA thiolation was performed in the presence of 0.01% Tween 20 in order to reduce the likelihood of protein denaturation and aggregation, the tPA(P)-ELIP conjugation efficiency was not quite as great as that obtained with the standard conjugation procedure and less optimal relative to what we and others have achieved routinely for IgG Ab conjugations. Further improvements in fibrin targeting efficiency may be achieved by conjugating ELIP to smaller portions of the tPA molecule, especially since a candidate fibrin-binding site has been identified, provided that the fibrin-binding affinity is largely retained.

In this initial set of experiments, satisfactory targeting was observed in the two-stage fibrin pad ELISA procedure, and the thermodynamics of the high-affinity binding interaction were able to be determined for ELIP-conjugated tPA(P), which were related to the unconjugated PPACK-inactivated tPA. Full retention of binding affinities in the presence of serum, like we previously found for anti-fibrin(ogen) (Klegerman, et al., 2007), indicates clinical utility for the formulation.

In previous thermodynamic studies of whole Ab and Fab fragment ELIP conjugations, we discovered a very good correlation between the enthalpy and entropy changes of the noncovalent associations and the corresponding functions for the gel-liquid crystal phase transition of the phosphatidylethanolamine (PE) acyl chains to which the antibodies were covalently conjugated through the PE head groups (Klegerman et al., 2007). Consequently, though not to be bound by theory, we currently understand that the Ab-Ag association energetics are somehow coupled to the PE major phase transition and that the transduction efficiency is dependent on the ionic nature of the noncovalent interaction. The present data were examined to determine whether the tPA-fibrin interaction conforms to the same relation. Importantly, the tPA(P)-ELIP system has essentially the same kind of noncovalent interaction/PE major phase transition linkage as was previously established for Ab-Ag associations. Notably, the specific nature of the transduction mechanism is different from IgG systems. We expect that further studies of successive ELIP conjugations to tPA-derived proteins will define the nature of the interaction dependence.

The importance of these data is that we have demonstrated the use of an inactivated therapeutic that can be employed as a targeting agent. This would allow the same compound to be adapted for targeting a delivery agent and separately for unrelated therapeutics when released from the delivery agent. In these experiments, the delivery agent, echogenic liposomes, also is a molecular imaging agent. These methodologies can similarly be used for developing the targeting aspects of other therapeutics and would make unnecessary the addition of further antibodies or peptides to carriers for targeted delivery, targeted molecular imaging, and targeted drug delivery.

The evaluation methods employed in this study (i.e., measures of conjugation and targeting efficiency, ligand-target affinity and avidity, and interaction thermodynamics) have been effective in predicting the utility of Ab-ELIP targeting of fibrin in vivo.

ACKNOWLEDGEMENTS

This work was supported, in part, by research grants HL59586 and HL74002 from the National Institutes of Health.

REFERENCES

Am. Heart Asso. Statistics Comm. and Stroke Statistics Subcomm. (2007). Heart disease and stroke statistics-2007 update. *Circulation* 115:e69-e171.

Angles-Cano, E. (1986). A spectrophotometric solid-phase fibrin-tissue plasminogen activator activity assay (SOFIA-tPA) for high-fibrin-affinity tissue plasminogen activators. *Anal Biochem* 153: 201-210.

Blasie, C. A., Berg, J. M. (2002). Structure-based thermodynamic analysis of a coupled metal binding-protein folding reaction involving a zinc finger peptide. *Biochemistry* 41:15068-15073.

Blasie, C. A., Berg, J. M. (2004). Entropy-enthalpy compensation in ionic interactions probed in a zinc finger peptide. *Biochemistry* 43:10600-10604.

Bringmann, P., Gruber, D., Liese, A., Toschi, L., Kratzschmar, J., Schleuning, W. D., Donner, P. (1995). Structural features mediating fibrin selectivity of vampire bat plasminogen activators. *J Biol Chem* 270:25596-25603.

Cheng, X. F., Brohlin, M., Pohl, G. Back, O., Wallen, P. (1995). Binding of tissue plasminogen activator to endothelial cells. *Thromb Res* 77:149-164.

Demos, S. M., Onyuksel, H., Gilbert, J., Roth, S. I., Kane, B., Jungblut, P., Pinto, J. V., McPherson, D. D., Klegerman, M. E. (1997). In vitro targeting of Ab-conjugated echogenic liposomes for site-specific ultrasonic image enhancement. *J Pharm Sci* 86:167-171.

Demos, S. M., Dagar, S., Klegerman, M., Nagaraj, A., McPherson, D. D., Onyuksel, H. (1998). In vitro targeting of acoustically reflective liposomes to fibrin under various flow conditions. *J Drug Target* 5:507-518.

Demos, S. M., Alkan-Onyuksel, H., Kane, B. J., Ramani, K., Nagaraj, A., Green, R., Klegerman, M. E., McPherson, D. D. (1999). In vivo targeting of acoustically reflective liposomes for intravascular and transvascular ultrasonic enhancement *J Am Col Cardiol* 33:867-875.

Edgell, T., McEvoy, F. Webbon, P., Gaffney, P. J. (1996). Monoclonal antibodies to human fibrin: interaction with other animal fibrins. *Thromb Haemost* 75:595-599.

Eldrup, N., Gronholdt, M. L., Sillesen, H., Nordestgaard, B. G. (2006). Elevated matrix metalloproteinase-9 associated with stroke or cardiovascular death in patients with carotid stenosis. *Circulation* 114:1847-1854.

Flacke, S., Fischer, S., Scott, M. J., Fuhrhop, R. J., Allen J. S., McLean, M., Winter, P., Sicard, G. A., Gaffney, P. J., Wickline, S. A., Lanza, G. M. (2001). Novel MRI contrast agent for molecular imaging of fibrin: implications for detecting vulnerable plaques. *Circulation* 104:1280-1285.

Hamilton, A., Huang, S. L., Warnick, D., Stein, A., Rabbat, M., Madhav, T., Kane, B., Nagaraj, A., Klegerman, M., MacDonald, R., McPherson, D. (2002). Left ventricular thrombus enhancement following the intravenous injection of echogenic immunoliposomes: studies in a new experimental model. *Circulation* 105:2772-2778.

Hamilton, A. J., Huang, S. L., Warnick, D., Rabbat, M., Kane, B., Nagaraj, A., Klegerman, M., McPherson, D. D. (2004). Intravascular ultrasound molecular imaging of atheroma components in vivo. *J Am Coll Cardiol* 43:453-460.

Klegerman, M. E., Hamilton, A. J., Huang, S. L., Tiukinhoy, S. D., Khan, A. A., MacDonald, R. C., McPherson, D. D. (2002). Quantitative Immunoblot assay for assessment of liposomal Ab conjugation efficiency. *Anal Biochem* 300: 46-52.

Klegerman, M. E., McPherson, D. D. (2007). Molecular characteristics of inactivated human tissue plasminogen activator association with fibrin implicate the nature and sites of the binding interactions. *Arterioscl Thromb Vasc Biol* 27:e-108.

Klegerman, M. E., Huang, S., Parikh, D., Martinez, J., Demos, S. M., Onyuksel, H. A., McPherson, D. D. (2007). Lipid contribution to the affinity of Ag association with specific antibodies conjugated to liposomes. *Biochim Biophys Acta* 1768:1703-16.

Koerner, S. K., Kolodziej, A., McMurry, T. J., Nair, S., Nivorozhkin, A. L., Sun, W. C., Wang, X. (2002). Peptide-based multimeric targeted contrast agents. U.S. Pat. No. 6,991,775.

Kolodgie, F. D., Gold, H. K., Burke, A. P., Fowler, D. R., Kruth, H. S., Weber, D. K., Farb, A., Guerrero, L. J., Hayase, M., Kutys, R., Narula, J., Finn, A. V., Virmani, R. (2003). Intraplaque hemorrhage and progression of coronary atheroma. *N Eng J Med* 349:2316-2325.

Lasch, J., Weissig, V., Brandl, M. (2003): Preparation of liposomes. In Torchilin, V. P., Weissig, V. eds. *Liposomes*, $2^{nd}$ Ed. New York: Oxford University Press, pp 24-25.

Naghavi, M., Libby, P., Falk, E., et al. (2003). From vulnerable plaque to vulnerable patient: a call for new definitions and risk assessment strategies: Part I. *Circulation* 108:1664-1672.

Nesheim, M., Fredenburgh, J. C., Larsen, G. R. (1990). The dissociation constants and stoichiometries of the interactions of lys-plasminogen and chloromethyl ketone derivatives of tissue plasminogen activator and the variant AFEIX with intact fibrin. *J Biol Chem* 265:21541-21548.

Nieuwenhuizen, W. (1992). Antibodies against fibrin; immunogenic peptides suitable for preparing the antibodies, method for determining fibrin and pharmaceutical preparation based on the antibodies. U.S. Pat. No. 5,124,439.

Ord, J. M., Hasapes, J., Daugherty, A., Thorpe, S. R., Bergmann, S. R., Sobel, B. E. (1992). Imaging of thrombi with tissue-type plasminogen activator rendered enzymatically inactive and conjugated to a residualizing label. *Circulation* 85:288-297.

Ranby, M., Wallen, P. (1981). A sensitive parabolic rate assay for the tissue plasminogen activator. *Prog Fibrinol* 5:233-235.

Raut, S., Gaffney, P. (1996). Evaluation of fibrin binding profile of two antifibrin monoclonal antibodies. *Thromb Haemost* 76:56-64.

Reno, J. M., Hadley, Stephen W., Mohler, M. A. (1993) Method of diagnosing blood clots using fibrin-binding proteins. U.S. Pat. No. 5,217,705.

Rosenthall, L., Leclerc, J. (1995). A new thrombus imaging agent. Human recombinant fibrin binding domain labeled with In-111. *Clin Nucl Med* 20:398-402.

Scopes, R. K. (1982): *Protein Purification: Principles and Practice*. New York: Springer, pp 265-266.

Sirol, M., Fuster, V. Badimon, J. J., Fallon, J. T., Toussaint, J. F., Fayad, Z. A. (2005). Chronic thrombus detection with in vivo magnetic resonance imaging and a fibrin-targeted contrast agent. *Circulation* 112:1594-1600.

Stracke, C. P., Katoh, M., Wiethoff, A. J., Parsons, E. C., Spangenberg, P., Spuntrup, E. (2007). Molecular MRI of cerebral venous sinus thrombosis using a new fibrin-specific MR contrast agent. *Stroke* 38:1476-1481.

Taillefer, R. (2001). Radiolabeled peptides in the detection of deep venous thrombosis. *Semin Nucl Med* 31:102-123.

Tiukinhoy-Laing, S. D., Buchanan, K., Parikh, D., Huang, S., MacDonald, R. C., McPherson, D. D., Klegerman, M. E. (2007). Fibrin targeting of tissue plasminogen activator-loaded echogenic liposomes. *J Drug Target* 15:109-114.

Torchilin, V. P., Weissig, V., Martin, F. J., Heath, T. D., New, R. R. C. (2003): Surface modification of liposomes. In Torchilin, V. P., Weissig, V. eds. *Liposomes*, $2^{nd}$ Ed. New York: Oxford University Press, pp 193-229.

Tsurupa, G., Medved, L. (2001). Fibrinogen αC Domains Contain Cryptic Plasminogen and tPA Binding Sites. *Ann NY Acad Sci* 936: 328-330.

Verheij en, J. H., Caspers, M. P. M., Chang, G. T. G., de Munk, G. A. W., Pouwels, P. H., Enger-Valk, B. E. (1986). Involvement of finger domain and kringle 2 domain of tissue-type plasminogen activator in fibrin binding and stimulation of activity by fibrin. *EMBO J* 5:3525-3530.

ABBREVIATIONS

A405 optical absorbance at 405 nm
Ab antibody
Ag antigen
B/F ratio of bound/free ligand
BSA bovine serum albumin
CE conjugation efficiency
CH cholesterol
DPPG 1,2 dipalmitoyl-sn-glycero-3-phosphoglycerol
$d_{sn}$ median equivalent spherical diameter
DTT dithiothreitol
$E_{50}$ echogenicity (MGSV) of a 50 μg/ml ELIP suspension
EACA ε-aminocaproic acid
ELIP echogenic liposome(s)
ELISA enzyme-linked immunosorbent assay
$\Delta G°$ standard Gibbs' free energy change
$\Delta H°$ standard enthalpy change IBA immunoblot assay
IgG immunoglobulin G
IVUS intravascular ultrasound
K2 Kringle 2 domain
$K_{assoc}$ association constant (affinity)
$K_D$ dissociation constant
MGSV mean gray scale value
MPB 4-(p-maleimidophenyl)butyrate
NRS normal rabbit serum
PBS 0.02M phosphate-buffered saline, pH 7.4
PBS-T PBS with 0.05% Tween 20
PC phosphatidyl choline
PE phosphatidyl ethanol
PPACK D-phe-L-pro-L-arg-chloromethyl ketone
$\Delta S°$ standard entropy change
$S_b$ standard error of the slope
SD standard deviation
SE standard error
SOFIA-tPA solid-phase fibrin-tissue plasminogen activator activity assay
SPDP 3-(2-pyridyldithio)propionic acid-N-hydroxysuccinimide ester
tPA tissue plasminogen activator
tPA(P) PPACK-inactivated tPA

TABLE 1

Preservation of tPA fibrin-binding capacity after PPACK inactivation.

| Treatment | Percent Starting Activity | High-Affinity $K_D$ (nM) @ 37° C. |
|---|---|---|
| Sham (Control) | 99.8 | 5.92 |
| D-phe-L-pro-L-arg-chloromethyl ketone (PPACK) Inactivation | 4.7 ± 2.9*† | 10.4 ± 1.4*‡ |

*S.E.;
n = 3;
†p < 0.01 vs. control;
‡p > 0.2 vs. control

TABLE 2 tPA(PPACK) binding affinities and thermodynamics.

| Affinity | T (°K) | $K_{assoc}$ (M$^{-1}$) | $\Delta H°$ (kcal/mole) | $\Delta G°$ (kcal/mole) | $\Delta S°$ (cal/mole°) |
|---|---|---|---|---|---|
| High | 278 | 4.67 × 10$^9$ | −21.7 | −12.3 | −33.8 |
|  | 297 | 5.04 × 10$^8$ |  | −11.8 |  |
|  | 310 | 7.65 × 10$^7$ |  | −11.2 |  |
| Low | 278 | 5.33 × 10$^8$ | −13.9 | −11.1 | −9.93 |
|  | 297 | 1.20 × 10$^8$ |  | −11.0 |  |
|  | 310 | 3.91 × 10$^7$ |  | −10.8 |  |

TABLE 3

Comparative tPA(P)-ELIP conjugation characteristics.

| Buffer Composition | Init. tPA(P) (mg) | % Yield After Act. | % Yield After Red. | hiols er Mol. | pec. .E. (%) | Conj. Eff. g/mg ipid | ol./ IP | ID @ 37° C. (nM) | Avidity M$^{-1}$/ LIP × 10$^{-12}$ | 50 |
|---|---|---|---|---|---|---|---|---|---|---|
| No Detergent | 0.85 | 25.4 | 14.4 | .8 | 8.0 | .41 | 12 | 1.90 | 0.480 | 4.1 |
| +Tween 20 | 1.01 | 19.0 | 10.6 | .8 | 4.4 | .77 | .003 | 0.62 | 0.151 | 9.1 |

TABLE 4 tPA(P)-ELIP binding affinities and thermodynamics (high affinity only).

| T (°K) | $K_{assoc}$ (M$^{-1}$) | $\Delta H°$ (kcal/mole) | $\Delta G°$ (kcal/mole) | $\Delta S°$ (cal/mole°) |
|---|---|---|---|---|
| 278 | 5.83 × 10$^8$ | −7.08 | −11.1 | +14.7 |
| 297 | 3.01 × 10$^8$ |  | −11.5 |  |
| 310 | 1.51 × 10$^8$ |  | −11.6 |  |

Although the invention has been described primarily in connection with particular embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

REFERENCES

Alexandrov A V, Molina C A, Grotta J C, Garami Z, Ford S R, Alvarez-Sabin J, Montaner J, Saqqur M, Demchuk A M, Moye L A, Hill M D, Wojner A W; CLOTBUST Investigators. 2004. Ultrasound-enhanced systemic thrombolysis for acute ischemic stroke. N Engl J Med 351:2170-2178.

Alkan-Onyuksel H, Murer S E, Lanza G M, Vonesh M J, Klegerman M E, McPherson D D. 1996. Development of inherently echogenic liposomes as an ultrasonic contrast agent. J Pharm Sci 85:486-490.

Bangham A D, Standish M M, Watkins J C. 1965. Diffusion of univalent ions across the lamellae of swollen phospholipids. J Mol Biol 13:238-252.

Bao S, Thrall B D, Miller D L. 1997. Transfection of a reporter plasmid into cultured cells by sonoporation in vitro. Ultrasound Med Biol 23:953-959.

Barzilai B, Saffitz J E, Miller J G, Sobel B E. 1987. Quantitative ultrasonic characterization of the nature of atherosclerotic plaques in human aorta. Circ Res 60:459-463.

Birnbaum Y, Luo H, Nagai T, Fishbein M C, Peterson T M, Li S, Kricsfeld D, Porter T R, Siegel R J. 1998. Noninvasive in vivo clot dissolution without a thrombolytic drug: Recanalization of thrombosed iliofemoral arteries by transcutaneous ultrasound combined with intravenous infusion of microbubbles. Circulation 97:130-134.

Cohen M G, Tuero E, Bluguermann J, Kevorkian R, Berrocal D H, Carlevaro 0, Picabea E, Hudson M P, Siegel R J, Douthat L, Greenbaum A B, Echt D, Weaver W D, Grinfeld L R. 2003. Transcutaneous ultrasound-facilitated coronary thrombolysis during acute myocardial infarction. Am J Cardiol 92:454-457.

Daffertshofer M, Hennerici M. 2003. Ultrasound in the treatment of ischaemic stroke. Lancet Neurol 2(5):283-290.

Eccleston D S, Horrigan M C, Ellis S G. 1996. Rationale for local drug delivery. Sem Inter Cardiol 1:8-16.

Eggers J, Koch B, Meyer K, Konig I, Seidel G. 2003. Effect of ultrasound on thrombolysis of middle cerebral artery occlusion. Ann Neurol 53:797-800.

Grayson L S, Hansbrough J F, Zapata-Sirvent R L, Kim T, Kim S. 1993. Pharmacokinetics of DepoFoam gentamicin delivery system and effect on soft tissue infection. J Surg Res 55:559-564.

Greenleaf W J, Bolander M E, Sarkar G, Goldring M B, Greenleaf J F. 1998. Artificial cavitation nuclei significantly enhance acoustically induced cell transfection. Ultrasound Med Biol 24:587-595.

Groothius D R. 2000. The blood-brain and blood tumor barriers: a review of strategies for increasing drug delivery. Neuro-Oncology 2:45-59.

Gurewich V. 2000. Thrombolysis: an unfinished agenda. Blood Coagul Thrombolysis 11: 401-408.

Hamilton A J, Rabbat M, Jain P, Belkind N, Huang S L, Nagaraj A, Klegerman M E, MacDonald R C, McPherson D D. 2002. A physiologic flow chamber model to define to intravascular ultrasound enhancement of fibrin using echogenic liposomes. Invest Radiol 37:215-221.

Huang S, Hamilton A, Nagaraj A, Tiukinhoy S, Klegerman M, McPherson D, MacDonald R. 2001. Improving ultrasound reflectivity and stability of echogenic liposomal dispersions for use as targeted ultrasound contrast agents. J Pharm Sci 90:1917-1926.

Huang S L, Hamilton A J, Pozharski E, Nagaraj A, Klegerman M E, McPherson D D, MacDonald R C. 2002a. Physical correlates of the ultrasonic reflectivity of lipid dispersions suitable as diagnostic contrast agents. Ultrasound Med Biol 28:339-348.

Huang S, Tiukinhoy S, McPherson D, MacDonald R. 2002b. Combined use of ultrasound and acoustic cationic liposomes results in improved gene delivery into smooth muscle cells. Molecular Ther 5:S9.

Huang S L, McPherson D D, MacDonald R C. 2002c. Ultrasound in conjunction with an ultrasonic-reflective transfection agent enhances gene delivery to cells. J Am Coll Cardiol 39:228A.

Huber P E, Pfisterer P. 2000. In vitro and in vivo transfection of plasmid DNA in the Dunning prostate tumor R3327-AT1 is enhanced by focused ultrasound. Gene Ther 7:1516-1525.

Jones J P, Chandraratna P A, Tak T, Thompson M, Lohr C, Kaiser S, Tsai J, Yigiter E. 1989. Correlation of chemical components with acoustic properties in atherosclerotic plaque. Ultrasonic Imaging 11:137-138.

Kim H J, Greenleaf J F, Kinnick R R, Bronk J T, Bolander M E. 1996. Ultrasound-mediated transfection of mammalian cells. Hum Gene Ther 7:1339-1346.

Klegerman M, Parikh D, Tiukinhoy-Laing S, McPherson D. 2006. Ability of human tissue plasminogen activator to act as a targeting agent in tPA-loaded echogenic liposomes. AAPS J. 8(S2): Abstr. T2111.

Koch S, Polhl P, Cobet U, Rainov N G. 2000. Ultrasound enhancement of liposome-mediated cell transfection is caused by cavitation effects. Ultrasound Med Biol 26:897903.

Landini L, Sarnelli R, Picano E, Salvaduri M. 1986. Evaluation of frequency dependence of backscatter coefficient in normal and atherosclerotic aortic walls. Ultrasound Med Biol 12:397-401.

Leonetti J P, Machy P, Degols G, Lebleu B, Leserman L. 1990. Antibody-targeted liposomes containing oligodeoxyribonucleotides complementary to viral RNA selectively inhibit viral replication. Proc Natl Acad Sci USA 87:2448-2451.

Martin F J, Heath T D, New RRC. 1990. Covalent attachment of proteins to liposomes. In New RRC (Ed): Liposomes: a practical approach, IRL Press, New York.

Miller M W, Miller D L, Brayman A A. 1996. A review of in vitro bioeffects of inertial ultrasonic from a mechanistic perspective. Ultrasound Med Biol 22:1131-1154.

Ng K H, Vonesh M J, Garti J T, Morales R E, Roth S I, McPherson D D. 1993. Intravascular ultrasonic characterization of atherosclerotic plaques. Circulation 88:1-502.

Picano E, Landini L, Lattanzi F, Salvadori M, Benassi A, Abbate A. 1988. Time domain echo pattern evaluations from normal and atherosclerotic arterial walls: a study in-vitro. Circulation 77:654-659.

Saad A H, Hahn G M. 1992. Ultrasound-enhanced effects of adriamycin against murine tumors. Ultrasound Med Biol 18:715-723.

Tachibana K, Tachibana S. 2001. The use of ultrasound for drug delivery. Echocardiography 18:323-328.

Tiukinhoy-Laing S D, Huang S, Klegerman M E, Holland C., MacDonald R C, McPherson D D. 2007. Ultrasound-facilitated thrombolysis using tissue-plasminogen activator-loaded echogenic liposomes. Thromb Res. In Press.

Tsurupa G, Medved L. 2001. Fibrinogen aC domains contain cryptic plasminogen and tPA binding sites. Ann NY Acad Sci 936:328-330.

Ward M, Wu J, Chiu J F. 1999. Ultrasound-induced cell lysis and sonoporation enhanced by contrast agents. J Acoust Soc Am 105:2951-2957.

What is claimed is:

1. A composition, comprising:
   an echogenic liposome (ELIP) having an exterior surface, an interior surface, and at least one bilayer comprising at least one lipid selected from the group consisting of saturated phospholipids, unsaturated phospholipids, mixed phospholipids, and cholesterol,
   a thrombolytic compound trapped by the ELIP; and
   tissue plasminogen activator (tPA) exposed on the exterior surface of the ELIP, wherein the tPA is the only active targeting molecule exposed on the exterior surface of the ELIP, and the enzymatic activity of the tPA exposed on the exterior surface of the ELIP is inhibited.

2. The composition of claim 1, wherein the at least one bilayer of the echogenic liposome comprises at least one lipid selected from the group consisting of dipalmitoylphosphatidylcholine (DPPC), dioleoylphosphatidylcholine (DOPC), dipalmitoylphosphatidylglycerol (DPPG), dipalmitoylphosphatidylethanolamine (DPPE), egg phosphatidylcholine (PC), and cholesterol.

3. The composition of claim 2, wherein the ELIP comprises from about 0 mole parts to about 90 mole parts DPPC, from about 0 mole parts to about 50 mole parts DOPC, from about 10 mole parts to about 50 mole parts DPPG, from about 0 mole parts to about 20 mole parts DPPE, from about 0 mole parts to about 90 mole parts egg PC, and from about 2 mole parts to about 15 mole parts cholesterol, wherein the total amount of DPPC, DOPC, DPPG, DPPE, egg PC, and cholesterol is 100 mole parts.

4. The composition of claim 3, wherein the ELIP comprises about 46 mole parts DPPC, about 24 mole parts DOPC, about 24 mole parts DPPG, and about 6 mole parts cholesterol.

5. The composition of claim 1, wherein the ELIP is intrinsically echogenic.

6. The composition of claim 1, wherein the thrombolytic compound is human tissue plasminogen activator (tPA).

7. The composition of claim 6, wherein the composition comprises from about 1 µg to about 50 µg entrapped tPA per 1 mg ELIP.

8. The composition of claim 1, further comprising a glycoprotein (GP) IIb/IIIa inhibitor selected from the group consisting of abciximab, eptifibatide, and tirofiban.

9. The composition of claim 1, wherein the tPA exposed on the exterior surface of the ELIP is inhibited with D-phe-L-pro-L-arg-chloromethyl ketone (PPACK) and is conjugated to the ELIP by a thioether linkage.

10. The composition of claim 2, wherein the ELIP comprises about 38 mole parts DPPC, about 24 mole parts DOPC, about 24 mole parts DPPG, about 8 mole parts DPPE, and about 6 mole parts cholesterol.

11. A method of treating a medical condition in a patient characterized by a thrombus in the patient's vasculature, comprising:
    administering to the patient, in an amount effective to reduce the size of the thrombus, a composition comprising an echogenic liposome (ELIP) having an exterior surface, an interior surface, and at least one bilayer comprising at least one lipid selected from the group consisting of saturated phospholipids, unsaturated phospholipids, mixed phospholipids, and cholesterol, a thrombolytic compound trapped by the ELIP; and tissue plasminogen activator (tPA) exposed on the exterior surface of the ELIP, wherein the tPA is the only active targeting molecule exposed on the exterior surface of the ELIP, and the enzymatic activity of the tPA exposed on the exterior surface of the ELIP is inhibited.

12. The method of claim 11, wherein the ELIP comprises from about 0 mole parts to about 90 mole parts DPPC, from about 0 mole parts to about 50 mole parts DOPC, from about 10 mole parts to about 50 mole parts DPPG, from about 0 mole parts to about 20 mole parts DPPE, from about 0 mole parts to about 90 mole parts egg PC, and from about 2 mole parts to about 15 mole parts cholesterol, wherein the total amount of DPPC, DOPC, DPPG, DPPE, egg PC, and cholesterol is 100 mole parts.

13. The method of claim 12, wherein the ELIP comprises about 46 mole parts DPPC, about 24 mole parts DOPC, about 24 mole parts DPPG, and about 6 mole parts cholesterol.

14. The method of claim 11, wherein the thrombolytic compound is human tissue plasminogen activator (tPA).

15. The method of claim 14, wherein the composition further comprises a glycoprotein (GP) IIb/IIIa inhibitor selected from the group consisting of abciximab, eptifibatide, and tirofiban.

16. The method of claim 11, wherein administering delivers to the patient from about 1 µg of the thrombolytic compound per kg body weight to about 1 mg of the thrombolytic compound per kg body weight.

17. The method of claim 11, wherein the tPA exposed on the exterior surface of the ELIP is inhibited with D-phe-L-pro-L-arg-chloromethyl ketone (PPACK) and is conjugated to the ELIP by a thioether linkage.

18. The method of claim 11, further comprising ultrasonic imaging of the thrombus.

19. The method of claim 11, further comprising applying ultrasonic energy to the ELIP and thrombus to enhance thrombolysis.

* * * * *